United States Patent
Seko et al.

(10) Patent No.: US 7,427,634 B2
(45) Date of Patent: *Sep. 23, 2008

(54) AMINO ACID DERIVATIVES AND PHARMACEUTICAL COMPOSITION COMPRISING, AS ACTIVE INGREDIENTS, THEM

(75) Inventors: Takuya Seko, Osaka (JP); Masashi Kato, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 585 days.

This patent is subject to a terminal disclaimer.

(21) Appl. No.: 10/892,366

(22) Filed: Jul. 16, 2004

(65) Prior Publication Data

US 2005/0009890 A1    Jan. 13, 2005

Related U.S. Application Data

(62) Division of application No. 09/743,393, filed on Jan. 10, 2001, now Pat. No. 6,903,119.

(51) Int. Cl.
*A61K 31/425* (2006.01)
*C07D 277/04* (2006.01)

(52) U.S. Cl. ........................ 514/371; 548/200
(58) Field of Classification Search ............ 514/371; 548/200
See application file for complete search history.

(56) References Cited

U.S. PATENT DOCUMENTS

| | | | |
|---|---|---|---|
| 2,563,743 A | 8/1951 | Plentl et al. | |
| 4,962,225 A | 10/1990 | Okada et al. | |
| 5,596,000 A | 1/1997 | Esser et al. | |
| 5,731,340 A | 3/1998 | Bras et al. | |
| 7,166,590 B2 * | 1/2007 | Seko et al. | 514/226.8 |

FOREIGN PATENT DOCUMENTS

| | | |
|---|---|---|
| EP | 0 194 464 A1 | 9/1986 |
| EP | 0 237 082 A2 | 9/1987 |
| EP | 0 405 391 | 1/1991 |
| EP | 0 520 200 | 12/1992 |
| EP | 0 697 403 A1 | 2/1996 |
| EP | 0 757 037 | 2/1997 |
| EP | 0 780 386 | 6/1997 |
| EP | 0 805 147 A1 | 11/1997 |
| EP | 0 997 147 A1 | 3/2000 |
| EP | 0 997 147 A1 | 5/2000 |
| JP | 6-80696 | 3/1994 |
| JP | 8-208690 | 8/1996 |
| JP | 8-217671 | 8/1996 |
| JP | 8-217751 | 8/1996 |
| WO | WO 89/02431 | 3/1989 |
| WO | WO 91/01976 | 2/1991 |
| WO | WO 93/15047 | 8/1993 |
| WO | WO 94/05693 A | 3/1994 |
| WO | WO 94/07815 | 4/1994 |
| WO | WO 94/12181 | 6/1994 |
| WO | WO 96/11940 | 4/1996 |
| WO | WO 97/49679 | 12/1997 |
| WO | WO 98/54123 | 12/1998 |
| WO | WO 99/02146 A | 1/1999 |
| WO | WO 99/25686 | 5/1999 |
| WO | WO 00/00470 | 1/2000 |

OTHER PUBLICATIONS

Beck et al. "Voltage dependent . . . " Epilepsy Res. v32 p. 321-332 (1998).*
Bowersox et al. "Selective blockade of N-type . . . " Brain Res. v.747 p. 343-347 (1997).*
Cox et al. "N-type calcium . . . " EXp. Opionion Ther. Patents v. 8(10) p. 1237-1250(1998).*
Tomiyama et al. "Cilnidipine more highly . . . " Hypertensiion Res. v.24(6) p. 679-684 (2001).*
CAS printout for Connell et al, Oct. 1993.
CAS printout for Ravi, et al, Apr. 1984.
CAS printout for Bodanzsky, et al, Feb. 1972.
CAS printout for Aubry, et al, May 1987.
Shono, Tatauya, "A New Synthetic Meth of α-amino acid from α-methoxyurethanes," Tetrahedron Letters, vol. 22, No. 25, pp. 2411-2412, 1981.
M. Ashraf Shalaby et al., "Thiopeptide Synthesis. α-Amino Thionoacid Derivatives of Nitrobenzotriazole as Thioacylating Agents," *J. Org. Chem.*, (1996) 61(25), 9045-9048.
Kosaku Noda et al., "A facile method for preparation of t-butyloxycarbonylamino acid p- nitroanilides," *Int. J. Peptide Protein Res* (1990) 36(2), 197-200.

(Continued)

*Primary Examiner*—Celia Chang
(74) *Attorney, Agent, or Firm*—Sughrue Mion, PLLC

(57) ABSTRACT

The present invention relates to the compounds of the formula (I) and salts thereof (all the symbols are the same meanings as described in the specification).

$$R^1-A-\underset{\underset{R^2}{|}}{N}-\overset{\overset{D-E-R^3}{|}}{\underset{\underset{O}{\|}}{C}}-J-R^4$$

(I)

The compounds of the formula (I) possess inhibitory activity of N-type calcium channel, so they are useful as drug for prevention and/or treatment of cerebral infarct, transient ischemic attack, encephalomyelopathy after cardiac operation, spinal angiopathy, hypertension with stress, neurosis, epilepsy, asthma and pollakiuria etc. or agent for the treatment of pain.

7 Claims, No Drawings

OTHER PUBLICATIONS

Shi Pu-Tao et al., "Opiate Multiple Receptor Binding Activity of Enkephalin Analogs," ACTA Biochimica and Biophysica Sinica (Jan. 1983), vol. 15, No. 1, 67-76, Abstract.

Castelhano et al., "Synthesis, Chemistry, and Absolute Configuration of Novel Transglutaminase Inhibitors Containing a 3-Halo-4,5-dihydroisoxazole," *Bioorganic Chemistry* (1988), 16(3), 335-40.

V.F. Pozdnev et al.., "Activation of carboxylic acids by pyrocarbonates. Synthesis of arylamides of *N*- protected amino acids and small peptides using dialkylk pyrocarbonates as condensing reagents," *Int. J. Peptide Protein Res.* (1994) 44(1), 36-48.

Václav Čeřovsky, et al., "Papain-Catalyzed Synthesis of 2-Naphthylamdes on N-Acylamino Acids and Dipeptides," *Collection Czech Chem. Comm.* (1987), vol. 52, 2309-16.

F. Orosz et al., "Derivatives of DL-1,2,3,4-Tetrahydro-2-Naphtylamine Acylated with Amino Acids," Acta Chimica Academiae Scientiarum Hungaricae (1966) 49(3), 291-302.

Michio Namikoshi et al., "Use of Tetrabutylammonium Fluoride as a Facile Deprotecting Reagent for 4-Nitrobenzyl, 2,2,2-Tricholorethyl, and Phenacyl Esters of Amino Acids," *J. Org. Chem* (1991), 56, 5464-5466.

Tohru Sugawara et al, "Application of a Unique Automated Synthesis System for Solution-phase Peptide Synthesis," *Chem. Pharm. Bull.* (1995), 43(8), 1272-1280.

Nobutaka Fujii et al., "Studies on Peptides. CXXXII. Evaluation of Two β-Carboxyl Protecting Groups of Aspartic Acid, Cycloheptyl and Cyclooctyl, for Peptide Synthesis," *Chem. Pharm. Bull* (1985), 34(2), 864--8.

Haruaka Yajima et al Chem. Pharm. Bull., "Studies ofn Peptides. CXLIII. Evaluation of β-Menthylasparate for Peptide Synthesis," (1986), 34(10) 4356-61.

Tam et al., "Mechanisms of Aspartimide Formation: The effects of Protecting Groups, Acid, Base, Temperature and Time," *Peptide Research* (1988), 1(1) 6-18.

Gasc et al., Chemical Abstracts, vol. 114:82543, 1991.

Shengeliya et al., Chemical Abstracts, vol. 107:77510, 1987.

Kowollik et al., Chemical Abstracts, vol. 103:105274, 1985.

Lau et al., Chemical Abstracts, vol. 99:64868, 1983.

Gillessen et al., Chemical Abstracts, vol. 72:67256, 1970.

Poroshin et al., Chemical Abstracts, vol. 63:89274, 1965.

A. Ino, et al., "Total Synthesis of the Antimycoplasma Antibiotic Micacocidin," *Tetrahedron Letters*, 39 (1998) 3509-3512, In English.

Y.R.Kim, et al., Soul Taehakkyo Yakhak Nonmunjip (1997), 22, 10-18; Database Caplus, Chemical Abstract Service, XP-002348211, Database accession No. 1998:714328, Abstract.

K. Undheim, et al., Acta Chemica Scandinavica (1947-1973) (1969) 23 (7) 2475-87; Database Caplus, Chemical Abstract Service, XP-002348212, Database accession No. 1970:32186, Abstract.

C. Palomo et al., Chemical Communication (Cambridge) (1996) (2) 161-62; Database Caplus, Chemical Abstract Service, XP-002348213, Database accession No. 1996:154232, Abstract.

* cited by examiner

US 7,427,634 B2

AMINO ACID DERIVATIVES AND PHARMACEUTICAL COMPOSITION COMPRISING, AS ACTIVE INGREDIENTS, THEM

This is a Divisional of application Ser. No. 09/743,393 filed Jan. 10, 2001 (now U.S. Pat. No. 6,903,119).

THE FIELD OF THE ART

The present invention relates to amino acid derivatives of the formula (I), process for the preparation thereof and pharmaceutical composition, as active ingredients, them.

More particularly, it relates to amino acid derivatives of the formula (I)

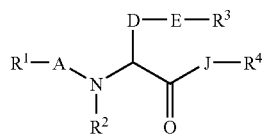
(I)

(wherein all the symbols are the same meanings as hereinafter described), non-toxic salts thereof and the hydrates thereof, processes for the preparation thereof, and N-type calcium channel blocker comprising them as active ingredients.

BACKGROUND OF THE RELATED ARTS

Calcium ion has been known as an intracellular messenger for signal transduction, and it is suggested that various physiological events are triggered by the elevation of intracellular calcium concentration. Calcium influx from extracellular fluid is one of the mechanisms for the elevation of intracellular calcium concentration. The gate of calcium influx is the voltage-dependent calcium channels. The voltage-dependent calcium channel is opened by the polarization of plasma membrane, and calcium ion influxes from extracellular fluid into the cell selectively through the channel according to the electrochemical gradient. The voltage-dependent calcium channels are classified into N-, L-, P-, Q- and T-type at present. It is known that L- and T-type calcium channels are distributed in the various tissues ubiquitously, and especially, L-type calcium channel is enriched in the smooth muscle cells or the cardiac muscle cells. On the other hand, N- and P-type calcium channels are mainly located in the nervous system and related to the neurotransmitter release. This neurotransmitter is stored in synaptic vesicles of nerve terminals at resting state. When action potential by signal transmission on nerve is conducted in pre-synaptic fiber and reaches to the nerve terminal, the voltage-dependent calcium channels are activated and then, calcium ion influxes into the nerve terminals. By these mechanisms, synaptic vesicles are fused with pre-synaptic membrane, and neurotransmitters in the vesicles are released. The released neurotransmitters are related to signal transmission in synapse due to binding to their receptors in post-synaptic membrane. From the above, an N-type calcium channel blocker is thought to be effective on various diseases induced by an excessive release of neurotransmitter. For example, it may be useful as agent for the prevention and/or treatment of cerebral infarct (J. Cereb. Blood Flow Metab., Vol. 17, 421-429, 1997), transient ischemic attack, encephalomyelopathy after cardiac operation, spinal angiopathy, hypertension with stress (Science., 239, 57-61, 1988), neurosis, epilepsy, asthma and pollakiuria etc. or agent for the treatment of pain (for example, acute pain, chronic pain, pain after operation, cancer pain, neuralgia, pain caused by infection etc.) (Pain, 60, 83-90, 1995).

The venoms isolated from the genus Conus, ω-conotoxin GVIA, MVIIA, are well known as N-type calcium channel blockers.

But, these ω-conotoxins are peptide compounds, so it is expected that they have various problems (for example, they are not absorbed into the living body easily). Therefore, there is a demand for arrangement of these blockers to non-peptide compounds namely to small-molecule. There are some reports relate to small-molecule as follows:

For example, it is described in the specification of Japanese Patent Kokai Hei 8-217671 that glycine derivatives of the formula (A)

(A)

(wherein $R^{1A}$ and $R^{2A}$ are, same or different, C1-19 straight or branched alkyl or C2-19 straight or branched alkenyl) and salts thereof are N-type calcium channel blocker.

It is described in the specification of EP 805147 that the compounds of the formula (B)

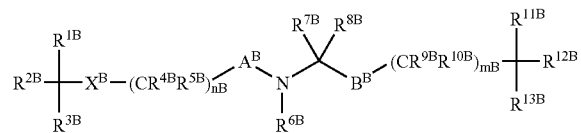
(B)

(wherein $R^{1B}$ is alkyl, $R^{2B}$ is hydrogen, optionally substituted alkyl, optionally substituted aryl or optionally substituted heteroaryl, $R^{3B}$ is hydrogen, CN, $X^B$ is bond or $SO_2$, $R^{4B}$, $R^{5B}$, $R^{6B}$, $R^{8B}$, $R^{9B}$ and $R^{10B}$ are each hydrogen or alkyl, $A^B$ is $CH_2$ or $Y^B CO$ (in which $Y^B$ is bond), $R^{7B}$ is C α-substituent of amino acid or ester thereof, $R^{6B}$ and $R^{7B}$ together form C3-5 alkylene chain optionally substituted by C1-4 alkyl or hydroxy or $CH_2$-$Z^B$-$CH_2$ (in which $Z^B$ is CO, S, SO, $SO_2$), $R^{7B}$ and $R^{8B}$ together form C3-5 alkylene chain optionally substituted by C1-4 alkyl or hydroxy, $B^B$ is $CON(R^{21B})$, mB is 0~2, $R^{11B}$ is hydrogen or alkyl, $R^{12B}$ is hydrogen, alkyl, optionally substituted aryl or optionally substituted heteroaryl, $R^{13B}$ is alkyl, optionally substituted aryl or optionally substituted heteroaryl, $R^{12B}$ and $R^{13B}$ together form C3-8 cycloalkyl), the salts thereof or the ester thereof are calcium channel modulator (necessary part is extracted in the explanation of the group).

Also, it is described in the specification of Japanese Patent Kokai Sho 61-200950 that the compound of the formula (C)

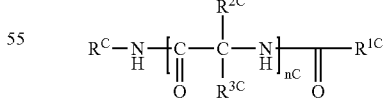
(C)

(wherein $R^C$ and $R^{1C}$ each independently, is lower alkyl, aryl-lower alkyl or phenyl optionally substituted by one or more electron-withdrawing or electron-donating group, $R^{2C}$ and $R^{3C}$ each independently, is hydrogen, lower alkyl, aryl-lower alkyl or phenyl optionally substituted with one or more electron-withdrawing or electron-donating group, and nC is 1~4) and pharmaceutically acceptable salts thereof are anti-convulsant agent.

In addition, the present inventors (applicant(s)) have filed two international applications relating to an N-type calcium channel inhibitor (WO99/02146 and international application No. PCT/99/03409 (filing date: Jun. 25, 1999)).

Further, as for an application relating to an N-type calcium channel inhibitor, WO 98/54123 is listed.

Besides the above applications, WO 99/25686 (cyclic amine derivatives possessing inhibitory action on chemokine) is listed.

DISCLOSURE OF THE INVENTION

As the result of energetic investigations in order to find compounds possessing inhibitory action on N-type calcium channel, the present inventors have found that the purpose has been accomplished by the compound of the formula (I).

The present invention relates to, (1) an amino acid derivative of the formula (I)

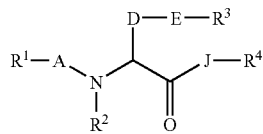

(I)

[wherein, $R^1$ is
1) phenyl,
2) C3-8 cycloalkyl,
3) heterocyclic ring,
4) C1-4 alkyl substituted with phenyl, C3-8 cycloalkyl or heterocyclic ring,
5) C1-4 alkoxy substituted with phenyl, C3-8 cycloalkyl or heterocyclic ring, or
6) C2-4 alkenyl substituted with phenyl, C3-8 cycloalkyl or heterocyclic ring, provided that all the said phenyl, C3-8 cycloalkyl and heterocyclic ring in $R^1$ is substituted with (a) four C1-4 alkyl or (b) one substituent selected from the following (i)-(xii) essentially, and the said ring may be substituted with 1~3 of substituent(s) selected from the group consisting of (i)-(xxiii):
(i) oxo,
(ii) C5-8 alkyl,
(iii) —COO—$R^5$ (in which, $R^5$ is hydrogen, C5-8 alkyl, C2-8 alkenyl, or C1-4 alkyl substituted with 1~3 of halogen or C1-4 alkoxy),
(iv) —(C1-4 alkylene)-COO$R^6$ (in which, $R^6$ is hydrogen, C1-8 alkyl, C2-8 alkenyl or C1-4 alkyl substituted with 1~3 of halogen),
(v) —CO—$R^7$ (in which, $R^7$ is C5-8 alkyl, C2-4 alkenyl, carbocyclic ring, heterocyclic ring or C1-8 alkyl substituted with one substituent selected from the following (1)-(8);
(1) carbocyclic ring,
(2) heterocyclic ring,
(3) hydroxy,
(4) C1-4 alkoxy,
(5) —OCO—(C1-4 alkyl),
(6) —O—(C1-4 alkylene)-O—(C1-4 alkyl),
(7) $NR^8R^9$ (in which, $R^8$ and $R^9$ each, independently, is hydrogen or C1-4 alkyl),
(8) halogen),
(vi) —(C1-4 alkylene)-CO—$R^{10}$ (in which, $R^{10}$ is C1-8 alkyl, C2-4 alkenyl, carbocyclic ring, heterocyclic ring or C1-8 alkyl substituted with one substituent selected from the following (1)-(8);
(1) carbocyclic ring,
(2) heterocyclic ring,
(3) hydroxy,
(4) C1-4 alkoxy,
(5) —OCO—(C1-4 alkyl),
(6) —O—(C1-4 alkylene)-O—(C1-4 alkyl),
(7) $NR^{11}R^{12}$ (in which, $R^{11}$ and $R^{12}$ each, independently, is hydrogen or C1-4 alkyl),
(8) halogen),
(vii) —CO—CO—$R^{13}$,
(viii) —CO—(C1-4 alkylene)-CO—$R^{14}$,
(ix) —$SO_2$—$R^{15}$ (in which, $R^{13}$, $R^{14}$ and $R^{15}$ each, independently, is C1-8 alkyl, C2-4 alkenyl, carbocyclic ring, heterocyclic ring, hydroxy, C1-4 alkoxy or C1-8 alkyl substituted with one substituent selected from the following (1)-(8);
(1) carbocyclic ring,
(2) heterocyclic ring,
(3) hydroxy,
(4) C1-4 alkoxy,
(5) —OCO—(C1-4 alkyl),
(6) —O—(C1-4 alkylene)-O—(C1-4 alkyl),
(7) $NR^{16}R^{17}$ (in which, $R^{16}$ and $R^{17}$ each, independently, is hydrogen or C1-4 alkyl),
(8) halogen),
(x) —$CONR^{18}R^{19}$ (in which, $R^{18}$ is hydrogen or C1-4 alkyl which may be substituted with one phenyl, $R^{19}$ is C1-8 alkyl or C2-4 alkenyl),
(xi) C1-8 alkyl substituted with 1~2 of substituent(s) selected from the group consisting of the following (1)-(7);
(1) hydroxy,
(2) C1-4 alkoxy,
(3) —O—(C1-4 alkylene)-O—(C1-4 alkyl),
(4) tetrahydropyran-2-yloxy,
(5) —$SR^{20}$ (in which, $R^{20}$ is hydrogen or C1-4 alkyl),
(6) halogen,
(7) $NR^{21}R^{22}$ (in which, $R^{21}$ and $R^{22}$ each, independently, is hydrogen or C1-4 alkyl),
(xii) hydroxy,
(xiii) C1-4 alkyl,
(xiv) C1-4 alkoxy,
(xv) phenyl,
(xvi) phenoxy,
(xvii) benzyloxy,
(xviii) —$SR^{23}$ (in which, $R^{23}$ is hydrogen or C1-4 alkyl),
(xix) C2-5 acyl,
(xx) halogen,
(xxi) C1-4 alkoxycarbonyl,
(xxii) nitro,
(xxiii) —$NR^{24}R^{25}$ (in which, $R^{24}$ and $R^{25}$ each, independently, is hydrogen, C1-4 alkyl or C1-4 alkoxycarbonyl, or $R^{24}$ and $R^{25}$ taken together with nitrogen atom to which is attached represents 5~7-membered saturated heterocyclic ring necessary containing one nitrogen atom and optionally further containing one nitrogen atom or one oxygen atom), A is single bond, —CO— or —$SO_2$—,
$R^2$ is hydrogen or C1-4 alkyl which may be substituted with one phenyl,
D is C1-4 alkylene or C2-4 alkenylene,
E is
1) —COO—, 2) —OCO—,
3) —CONR$^{26}$— (in which, R$^{26}$ is hydrogen or C1-4 alkyl),
4) —NR$^{27}$CO— (in which, R$^{27}$ is hydrogen or C1-4 alkyl),
5) —O—,
6) —S—,
7) —SO—,
8) —SO$_2$—,
9) —NR$^{28}$— (in which, R$^{28}$ is hydrogen or C1-4 alkyl),
10) —CO—,
11) —SO$_2$NR$^{29}$— (in which, R$^{29}$ is hydrogen or C1-4 alkyl) or
12) —NR$^{30}$SO$_2$— (in which, R$^{30}$ is hydrogen or C1-4 alkyl),
R$^3$ is
1) carbocyclic ring,
2) heterocyclic ring or
3) C1-4 alkyl substituted with carbocyclic ring or heterocyclic ring, in which, all the said carbocyclic ring and heterocyclic ring in R$^3$ may be substituted with 1~3 of substituent(s) selected from the group consisting of the following (i)-(xi):
　(i) C1-4 alkyl,
　(ii) C1-4 alkoxy,
　(iii) phenyl,
　(iv) phenoxy,
　(v) benzyloxy,
　(vi) —SR$^{31}$ (in which, R$^{31}$ is hydrogen or C1-4 alkyl),
　(vii) C2-5 acyl,
　(viii) halogen,
　(ix) C1-4 alkoxycarbonyl,
　(x) nitro,
　(xi) —NR$^{32}$R$^{33}$ (in which, R$^{32}$ and R$^{33}$ each, independently, is hydrogen, C1-4 alkyl or C1-4 alkoxycarbonyl, or R$^{32}$ and R$^{33}$ taken together with nitrogen atom to which is attached represents 5~7-membered saturated heterocyclic ring necessary containing one nitrogen atom and optionally further containing one nitrogen atom or one oxygen atom),
J is
1) —O—,
2) —NR$^{34}$— (in which, R$^{34}$ is hydrogen, C1-4 alkyl which may be substituted with one phenyl, NR$^{35}$R$^{36}$ (in which, R$^{35}$ and R$^{36}$ each, independently, is hydrogen or C1-4 alkyl), hydroxy, C1-4 alkoxy, —(C1-4 alkylene)-OH, —(C1-4 alkylene)-O—(C1-4 alkyl) or —(C1-4 alkylene)-O—(C2-5 acyl)),
3) —NR$^{37}$—NR$^{38}$— (in which, R$^{37}$ and R$^{38}$ each, independently, is hydrogen or C1-4 alkyl which may be substituted with one phenyl),
4) —NR$^{39}$—(C1-4 alkylene)-NR$^{40}$— (in which, R$^{39}$ and R$^{40}$ each, independently, is hydrogen or C1-4 alkyl which may be substituted with one phenyl),
5) —NR$^{41}$—(C1-4alkylene)-O— (in which, R$^{41}$ is hydrogen or C1-4 alkyl which may be substituted with one phenyl) or
6) —NR$^{42}$—(C1-4 alkylene)-S— (in which, R$^{42}$ is hydrogen or C1-4 alkyl which may be substituted with one phenyl),
R$^4$ is R$^{4-1}$ or R$^{4-2}$,
R$^{4-1}$ is
1) C1-8 alkyl,
2) carbocyclic ring,
3) heterocyclic ring or
4) C1-8 alkyl substituted with 1~3 of substituent(s) selected from the group consisting of the following (i)-(v);
　(i) carbocyclic ring,
　(ii) heterocyclic ring,
　(iii) COOR$^{43}$ (in which, R$^{43}$ is hydrogen or C1-4 alkyl substituted with one phenyl (in which, phenyl may be substituted with C1-4 alkoxy)),
　(iv) SR$^{44}$ (in which, R$^{44}$ is hydrogen or C1-4 alkyl),
　(v) OR$^{45}$ (in which, R$^{45}$ is hydrogen or C1-4 alkyl), or when J is —NR$^{34}$—, —NR$^{37}$—NR$^{38}$— or —NR$^{39}$—(C1-4 alkylene)-NR$^{40}$—, each R$^{4-1}$ and R$^{34}$, R$^{4-1}$ and R$^{38}$, and R$^{4-1}$ and R$^{40}$ taken together with nitrogen atom to which is attached may represent heterocyclic ring, in which all the said carbocyclic ring and heterocyclic ring in R$^{4-1}$, and heterocyclic ring represented by each R$^{4-1}$ and R$^{34}$, R$^{4-1}$ and R$^{38}$, and R$^{4-1}$ and R$^{40}$ taken together with nitrogen atom to which is attached may be substituted with 1~3 of substituent(s) selected from the group consisting of the following (i)-(x):
　(i) C1-4 alkyl,
　(ii) C1-4 alkoxy,
　(iii) —SR$^{46}$ (in which, R$^{46}$ is hydrogen or C1-4 alkyl),
　(iv) C2-5 acyl,
　(v) halogen,
　(vi) C1-4 alkoxycarbonyl,
　(vii) nitro,
　(viii) —NR$^{47}$R$^{48}$ (in which, R$^{47}$ and R$^{48}$ each, independently, is hydrogen, C1-4 alkyl or C1-4 alkoxycarbonyl),
　(ix) hydroxy,
　(x) —(C1-4 alkylene)-O—(C1-4 alkyl),
R$^{4-2}$ is -L-M,
-L- is
1) -carbocyclic ring-,
2) -heterocyclic ring- or
3) (C1-4 alkylene)-(carbocyclic ring or heterocyclic ring)-, or when J is —NR$^{34}$—, —NR$^{37}$—NR$^{38}$— or —NR$^{39}$—(C1-4 alkylene)-NR$^{40}$—, each L and R$^{34}$, L and R$^{38}$, and L and R$^{40}$ taken together with nitrogen atom to which is attached may represent -heterocyclic ring-,
M is
1) carbocyclic ring,
2) heterocyclic ring
3) C1-4 alkyl substituted with 1~2 of substituent(s) selected from the group consisting of the following (i)-(ii);
　(i) carbocyclic ring,
　(ii) heterocyclic ring,
4) —O-(carbocyclic ring or heterocyclic ring),
5) —S-(carbocyclic ring or heterocyclic ring),
6) —NR$^{49}$-(carbocyclic ring or heterocyclic ring) (in which, R$^{49}$ is hydrogen or C1-4 alkyl which may be substituted with one phenyl),
7) —O—(C1-4 alkylene)-(carbocyclic ring or heterocyclic ring),
8) —S—(C1-4 alkylene)-(carbocyclic ring or heterocyclic ring),
9) —NR$^{50}$—(C1-4 alkylene)-(carbocyclic ring or heterocyclic ring) (in which, R$^{50}$ is hydrogen, C1-4 alkyl which may be substituted with one phenyl or C2-5 acyl which may be substituted with 1~3 of halogen) or
10) —CO-(carbocyclic ring or heterocyclic ring), or the said carbocyclic ring and heterocyclic ring in L and M, and heterocyclic ring represented by each L and R$^{34}$, L and R$^{38}$, and L and R$^{40}$ taken together with nitrogen atom to which is attached may be substituted with 1~3 of substituent(s) selected from the group consisting of the following (i)-(xiv):
　(i) C1-4 alkyl,
　(ii) C2-4 alkenyl,
　(iii) hydroxy,
　(iv) C1-4 alkoxy,
　(v) —(C1-4 alkylene)-OH, (vi) —(C1-4 alkylene)-O—(C1-4 alkyl),
(vii) halogen,
(viii) $NR^{51}R^{52}$ (in which, $R^{51}$ and $R^{52}$ each, independently, is hydrogen, C1-4 alkyl or C1-4 alkoxycarbonyl, or $R^{51}$ and $R^{52}$ taken together with nitrogen atom to which is attached represents 5~7-membered saturated heterocyclic ring necessary containing one nitrogen atom and optionally further containing one nitrogen atom or one oxygen atom),
(ix) $SR^{53}$ (in which, $R^{53}$ is hydrogen or C1-4 alkyl),
(x) nitro,
(xi) trifluoromethyl,
(xii) C1-4 alkoxycarbonyl,
(xiii) oxo,
(xiv) C2-5 acyl] or a non-toxic salt thereof, or a hydrate thereof,
(2) process for preparation of an amino acid derivative of the formula (I) or a non-toxic salt thereof, or a hydrate thereof and
(3) a pharmaceutical composition (N-type calcium channel inhibitor) comprising, as an active ingredient, an amino acid derivative of the formula (I) or a non-toxic salt thereof, or a hydrate thereof.

Unless otherwise specified, all isomers are included in the present invention. For example, alkyl, alkenyl, alkynyl and alkylene group includes straight or branched ones. In addition, isomers on double bond, ring, fused ring (E-, Z-, cis-, trans-isomer), isomers generated from asymmetric carbon atom(s) (R-, S-, α-, β-isomer, enantiomer, diastereomer), optically active isomers (D-, L-, d-, l-isomer), polar compounds generated by chromatographic separation (more polar compound, less polar compound), equilibrium compounds, mixtures thereof at voluntary ratios and racemic mixtures are also included in the present invention.

In the formula (I), C1-4 alkyl means methyl, ethyl, propyl, butyl and isomers thereof.

In the formula (I), C5-8 alkyl means pentyl, hexyl, heptyl, octyl and isomers thereof.

In the formula (I), C1-8 alkyl means methyl, ethyl, propyl, butyl, pentyl, hexyl, heptyl, octyl and isomers thereof.

In the formula (I), C3-8 cycloalkyl means cyclopropyl, cyclobutyl, cyclopentyl, cyclohexyl, cycloheptyl and cyclooctyl.

In the formula (I), C1-4 alkylene means methylene, ethylene, propylene, butylene and isomers thereof.

In the formula (I), C1-4 alkoxy means methoxy, ethoxy, propoxy, butoxy and isomers thereof.

In the formula (I), C2-4 alkenyl means ethenyl, propenyl, butenyl and isomers thereof.

In the formula (I), C2-8 alkenyl means ethenyl, propenyl, butenyl, pentenyl, hexenyl, heptenyl, octenyl and isomers thereof.

In the formula (I), C2-4 alkenylene means ethenylene, propenylene, butenylene and isomers thereof.

In the formula (I), C2-5 acyl means acetyl, propionyl, butyryl, valeryl and isomers thereof.

In the formula (I), C1-4 alkoxycarbonyl means methoxycarbonyl, ethoxycarbonyl, propoxycarbonyl, butoxycarbonyl and isomers thereof.

In the formula (I), halogen means fluoride, chloride, bromide and iodide.

In the formula (I), carbocyclic ring means C3-10 mono-, bi-carbocyclic ring and fused carbocyclic ring. For example, the said C3-10 mono-, bi-carbocyclic ring and fused carbocyclic ring includes cyclopropane, cyclobutane, cyclopentane, cyclohexane, cycloheptane, cyclooctane, cyclononane, cyclodecane, cyclopentene, cyclohexene, cyclopentadiene, cyclohexadiene, benzene, pentalene, indene, naphthalene, azulene, dihydronaphthalene, tetrahydronaphthalene, perhydronaphthalene, indane (dihydroindene), perhydroindene, bicyclopentane, bicyclohexane, bicycloheptane (bicyclo[2.2.1]heptane), bicycloheptene (bicyclo[2.2.1]hept-2-ene), bicyclooctane, bicyclononane, bicyclodecane, adamanthane etc.

In the formula (I), 5~7-membered saturated heterocyclic ring containing one nitrogen atom and further optionally containing one nitrogen atom or one sulfur atom represented by each $R^{24}$ and $R^{25}$, $R^{32}$ and $R^{33}$, and $R^{51}$ and $R^{52}$ taken together with nitrogen atom to which is attached means for example, pyrrolidine, piperidine, piperazine, morpholine, perhydroazepine.

In the formula (I), heterocyclic ring represented by each $R^{4-1}$ and $R^{34}$, $R^{4-1}$ and $R^{38}$, $R^{4-1}$ and $R^{40}$, L and $R^{34}$, L and $R^{38}$, and L and $R^{40}$ taken together with nitrogen atom to which is attached means 5~15-membered mono- or bi-heterocyclic ring essentially containing one nitrogen atom and further optionally containing one nitrogen atom, one oxygen atom and/or one sulfur atom which is unsaturated or saturated partially or fully. For example, the said 5~15-membered mono- or bi-heterocyclic ring essentially containing one nitrogen atom and further optionally containing one nitrogen atom, one oxygen atom and/or one sulfur atom which is unsaturated or saturated partially or fully includes pyrroline, pyrrolidine, imidazoline, imidazolidine, pyrazoline, pyrazolidine, piperidine, piperazine, tetrahydropyrimidine, hexahydropyrimidine, tetrahydropyridazine, hexahydropyridazine, hexahydroazepine, tetrahydrooxazole, tetrahydroisooxazole, tetrahydrothiazole, tetrahydroisothiazole, morpholine, thiomorpholine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthylidine, tetrahydronaphthylidine, perhydronaphthylidine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzooxazole, perhydrobenzooxazole, dihydrobenzothiazole, perhydrobenzothiazole, dihydrobenzoimidazole, perhydrobenzoimidazole, pyrrole, imidazole, pyrazole, indole, isoindole, indazole, benzoimidazole etc.

In the formula (I), heterocyclic ring other than the above means 5~15-membered mono- or bi-heterocyclic ring containing 1~2 nitrogen atom(s), 1~2 oxygen atom(s) and/or one sulfur atom which is unsaturated or saturated partially, or fully (abbreviated as heterocyclic ring (A)). For example, the said 5~15-membered mono- or bi-heterocyclic ring containing 1~2 nitrogen atom(s), 1~2 oxygen atom(s) and/or one sulfur atom which is unsaturated or saturated partially or fully includes pyrroline, pyrrolidine, imidazoline, imidazolidine, pyrazoline, pyrazolidine, piperidine, piperazine, tetrahydropyrimidine, hexahydropyrimidine, tetrahydropyridazine, hexahydropyridazine, hexahydroazepine, dihydrofuran, tetrahydrofuran, dihydropyran, tetrahydropyran, dihydrothiophene, tetrahydrothiophene, dihydrothiain(dihydrothiopyran), tetrahydrothiain (tetrahydrothiopyran), dihydrooxazole, tetrahydrooxazole, dihydroisooxazole, tetrahydroisooxazole, dihydrothiazole, tetrahydrothiazole (thiazolidine), dihydroisothiazole, tetraisothiazole, morpholine, thiomorpholine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthylidine, tetrahydronaphthylidine, perhydronaphthylidine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzooxazole, perhydrobenzooxazole, dihydrobenzothiazole, perhydrobenzothiazole, dihydrobenzoimidazole, perhydrobenzoimidazole, dihydrobenzoxazine, dioxaindane, benzodioxane, quinuclidine, pyrrole, imidazole, pyrazole, pyridine, pyrazine, pyrimidine, pyridazine, pyridazine, azepine, diazepine, furan, pyran, oxepine, oxazepine, thiophene, thiain(thiopyran), thiepine, oxazole, isooxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthylidine, quinoxaline, quinazoline, cinnoline, benzooxazole, benzothiazole, benzoimidazole, oxatetrahydrofuran etc.

$R^1$ is preferably heterocyclic ring or C1-4 alkyl substituted with heterocyclic ring, and more preferably heterocyclic ring (provided that all the said heterocyclic ring is substituted). Such a heterocyclic ring includes the said heterocyclic ring (A), preferably, 5~15-membered mono- or bi-heterocyclic ring containing 1~2 nitrogen atom(s), 1~2 oxygen atom(s) or one sulfur atom which is unsaturated or saturated partially or fully (for example, dihydrooxazole, tetrahydrooxazole, dihydroisooxazole, tetrahydroisooxazole, dihydrothiazole, tetrahydrothiazole(thiazolidine), dihydroisothiazole, tetraisothiazole, morpholine, thiomorpholine, dihydrobenzooxazole, perhydrobenzooxazole, dihydrobenzothiazole, perhydrobenzothiazole, dihydrobenzoxazine, oxazepine, oxazole, isooxazole, thiazole, isothiazole, oxadiazole, oxazine, oxadiazine, oxazepine, oxadiazepine, thiadiazole, thiazine, thiadiazine, thiazepine, thiadiazepine, benzooxazole, benzothiazole etc.), more preferably 5~7-membered mono-heterocyclic ring containing one nitrogen atom and one oxygen atom or one sulfur atom which is unsaturated or saturated partially or fully (for example, dihydrooxazole, tetrahydrooxazole, dihydroisooxazole, tetrahydroisooxazole, dihydrothiazole, tetrahydrothiazole (thiazolidine), dihydroisothiazole, tetraisothiazole, morpholine, thiomorpholine, oxazepine, oxazole, isooxazole, thiazole, isothiazole, oxazine, oxazepine, thiazine, thiazepine etc.), and most preferably tetrahydrothiazole(thiazolidine).

In addition, each ring of $R^1$ is essentially substituted with (b-1) one substituent selected from the following (i), (ii), (iii-a), (iv)-(xii) and further may be substituted with 1~3 of substituent(s) selected from the group consisting of the following (i), (ii), (iii-a), (iv)-(xxiii):

(i) oxo,
(ii) C5-8 alkyl,
(iii-a) —COO—$R^{5.4}$ (in which, $R^{5.4}$ is hydrogen, C5-8 alkyl, C2-8 alkenyl or C1-4 alkyl substituted with 1~3 of halogen),
(iv) —(C1-4 alkylene)-COO$R^6$ (in which, $R^6$ is hydrogen, C1-8 alkyl, C2-8 alkenyl or C1-4 alkyl substituted with 1~3 of halogen),
(v) —CO—$R^7$ (in which, $R^7$ is C5-8 alkyl, C2-4 alkenyl, carbocyclic ring, heterocyclic ring or C1-8 alkyl substituted with one substituent selected from the following (1)-(8);
  (1) carbocyclic ring,
  (2) heterocyclic ring,
  (3) hydroxy,
  (4) C1-4 alkoxy,
  (5) —OCO—(C1-4 alkyl),
  (6) —O—(C1-4 alkylene)-O—(C1-4 alkyl),
  (7) $NR^8R^9$ (in which, $R^8$ and $R^9$ each, independently, is hydrogen or C1-4 alkyl),
  (8) halogen,
(vi) —(C1-4 alkylene)-CO—$R^{10}$(in which, $R^{10}$ is C1-8 alkyl, C2-4 alkenyl, carbocyclic ring, heterocyclic ring or C1-8 alkyl substituted with one substituent selected from the following (1)-(8);

(1) carbocyclic ring,
  (2) heterocyclic ring,
  (3) hydroxy,
  (4) C1-4 alkoxy,
  (5) —OCO—(C1-4 alkyl),
  (6) —O—(C1-4 alkylene)-O—(C1-4 alkyl),
  (7) $NR^{11}R^{12}$ (in which, $R^{11}$ and $R^{12}$ each, independently, is hydrogen or C1-4 alkyl),
  (8) halogen,
(vii) —CO—CO—$R^3$,
(viii) —CO—(C1-4 alkylene)-CO—$R^{14}$,
(ix) —$SO_2$—$R^{15}$ (in which, $R^{13}$, $R^{14}$ and $R^{15}$ each, independently, is C1-8 alkyl, C2-4 alkenyl, carbocyclic ring, heterocyclic ring, hydroxy, C1-4 alkoxy or C1-8 alkyl substituted with one substituent selected from the following (1)-(8);
  (1) carbocyclic ring,
  (2) heterocyclic ring,
  (3) hydroxy,
  (4) C1-4 alkoxy,
  (5) —OCO—(C1-4 alkyl),
  (6) —O—(C1-4 alkylene)-O—(C1-4 alkyl),
  (7) $NR^{16}R^{17}$ (in which, $R^{16}$ and $R^{17}$ each, independently, is hydrogen or C1-4 alkyl),
  (8) halogen,
(x) —$CONR18R^{19}$ (in which, $R^{18}$ is hydrogen or C1-4 alkyl which may be substituted with one phenyl, $R^{19}$ is C1-8 alkyl or C2-4 alkenyl),
(xi) C1-8 alkyl substituted with 1~2 of substituent(s) selected from the group consisting of the following (1)-(7);
  (1) hydroxy,
  (2) C1-4 alkoxy,
  (3) —O—(C1-4 alkylene)-O—(C1-4 alkyl),
  (4) tetrahydropyran-2-yloxy,
  (5) —$SR^{20}$ (in which, $R^{20}$ is hydrogen or C1-4 alkyl),
  (6) halogen,
  (7) $NR^{21}R^{22}$ (in which, $R^{21}$ and $R^{22}$ each, independently, is hydrogen or C1-4 alkyl),
(xii) hydroxy,
(xiii) C1-4 alkyl,
(xiv) C1-4 alkoxy,
(xv) phenyl,
(xvi) phenoxy,
(xvii) benzyloxy,
(xviii) —$SR^{23}$ (in which, $R^{23}$ is hydrogen or C1-4 alkyl),
(xix) C2-5 acyl,
(xx) halogen,
(xxi) C1-4 alkoxycarbonyl,
(xxii) nitro,
(xxiii) —$NR^{24}R^{25}$ (in which, $R^{24}$ and $R^{25}$ each, independently, is hydrogen, C1-4 alkyl or C1-4 alkoxycarbonyl, or $R^{24}$ and $R^{24}$ taken together with nitrogen atom to which is attached represents 5~7-membered saturated heterocyclic ring necessary containing one nitrogen atom and optionally further containing one nitrogen atom or one oxygen atom)

is preferable (in the following explanation, for example, substituent "(i)", "(iii)" of each ring in $R^1$ means
(i) oxo,
(iii) —COO—$R^5$ (in which, $R^5$ is hydrogen, C5-8 alkyl, C2-8 alkenyl or C1-4 alkyl substituted with 1~3 of halogen or C1-4 alkoxy)).

Further, when $R^1$ is group containing thiazolidine and such a ring is substituted with the substituent (i) oxo, then the said oxo is preferably bonded to the sulfur atom in thiazolidine ring.

In addition, when $R^1$ is group containing thiazolidine, the substituent of such a ring is preferably the said substituent (ii), (iii), (iv)-(xxiii).

The above group containing thiazolidine means thiazolidine, C1-4 alkyl substituted with thiazolidine, C1-4 alkoxy substituted with thiazolidine and C2-4 alkenyl substituted with thiazolidine.

A is preferably single bond or —CO—, and more preferably —CO—.

D is preferably every group, more preferably C1-4 alkylene, and most preferably methylene.

$R^2$ is preferably every group, more preferably hydrogen or methyl substituted with one phenyl, and most preferably hydrogen.

E is preferably —COO—, —O—, —S—, —SO— or —$SO_2$—, more preferably —O— or —S—, and most preferably —S—.

$R^3$ is preferably carbocyclic ring or C1-4 alkyl substituted with carbocyclic ring (provided that all the said carbocyclic ring may be substituted), more preferably C3-10 cycloalkyl such as cyclopropane, cyclobutane, cyclopentane, cyclohexane, cycloheptane, cyclooctane, cyclononane, cyclodecane or C1-4 alkyl substituted with C3-10 cycloalkyl (provided that all the said cycloalkyl may be substituted), much more preferably cyclopentyl, cyclohexyl, or methyl substituted with cyclopentyl or cyclohexyl, and most preferably methyl substituted with cyclohexyl.

J is preferably —$NR^{34}$— (in which, $R^{34}$ is the same meaning as hereinbefore defined) or —$NR^{39}$—(C1-4 alkylene)-$NR^{40}$—, and more preferably —$NR^{34}$—.

In $R^4$, $R^{4-1}$ is preferably carbocyclic ring, heterocyclic ring or C1-8 alkyl substituted with carbocyclic ring or heterocyclic ring, and more preferably C1-8 alkyl substituted with carbocyclic ring, and most preferably C1-4 alkyl substituted with benzene (all the ring may be substituted).

In $R^4$, (-L-M) represented by $R^{4-2}$ is preferably the following group.

That is to say, L is preferably every group, and more preferably heterocyclic ring (such a ring may be substituted). Such a heterocyclic ring includes the said heterocyclicn ring (A), and preferably 5~15-membered mono- or bi-heterocyclicn ring containing 1—2 nitrogen atom(s) which is unsaturated or saturated partially or fully (for example, pyrroline, pyrrolidine, imidazoline, imidazolidine, pyrazoline, pyrazolidine, piperidine, piperazine, tetrahydropyrimidine, hexahydropyrimidine, tetrahydropyridazine, hexahydropyridazine, hexahydroazepine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthylidine, tetrahydronaphthylidine, perhydronaphthylidine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoimidazole, perhydrobenzoimidazole, quinuclidine, pyrrole, imidazole, pyrazole, pyridine, pyrazine, pyrimidine, pyridazine, pyridazine, azepine, diazepine, indole, isoindole, indazole, quinoline, isoquinoline, phthalazine, naphthylidine, quinoxaline, quinazoline, cinnoline, benzoimidazole etc.), more preferably 5~7-membered mono-heterocyclicn ring containing 1~2 nitrogen atom(s) which is unsaturated or saturated partially or fully (for example, pyrroline, pyrrolidine, imidazoline, imidazolidine, pyrazoline, pyrazolidine, piperidine, piperazine, tetrahydropyrimidine, hexahydropyrimidine, tetrahydropyridazine, hexahydropyridazine, hexahydroazepine, pyrrole, imidazole, pyrazole, pyridine, pyrazine, pyrimidine, pyridazine, pyridazine, azepine, diazepine etc.), and most preferably piperidine.

Further, M is preferably every group, more preferably C1-4 alkyl substituted with 1~2 of substituent(s) selected from the group consisting of carbocyclic ring and heterocyclic ring, much more preferably C1-4 alkyl substituted with 1~2 of substituent(s) selected from the group consisting of phenyl and C3-10 cycloalkyl, and most preferably methyl substituted with one phenyl (all the ring may be substituted).

In $R^4$, group represented by each $R^{4-1}$ and $R^{4-2}$ is preferable, and group represented by $R^{4-2}$ is more preferable.

[Salts]

All the non-toxic salts are also included in the present invention. For example, the compounds of the formula (I) of the present invention may be converted into the corresponding salts by known methods. Non-toxic and water-soluble salts are preferable. Suitable salts, for example, are follows: salts of alkaline metals (potassium, sodium etc.), salts of alkaline earth metals (calcium, magnesium etc.), ammonium salts, salts of pharmaceutically acceptable organic amines (tetramethylammonium, triethylamine, methylamine, dimethylamine, cyclopentylamine, dicyclohexylamine, benzylamine, phenethylamine, piperidine, monoethanolamine, diethanolamine, tris(hydroxymethyl)amine, lysine, arginine, N-methyl-D-glucamine etc.).

The compounds of the formula (I) of the present invention may be converted into the corresponding acid additional salts by methods known per se. Non-toxic and water-soluble acid addition salts are preferable. Suitable acid addition salts, for example, are salts of inorganic acids, e.g., hydrochloride, hydrobromide, sulphate, phosphate, nitrate etc., or salts of organic acids, e.g., acetate, trifluoroacetate, lactate, tartarate, oxalate, fumarate, maleate, citrate, benzoate, methanesulphonate, ethanesulphonate, benzenesulphonate, toluenesulphonate, isethioate, glucuronate, gluconate etc.

The compounds of the formula (I) of the present invention or salts thereof may be converted into hydrate thereof by methods known per se.

In the compounds of the formula (I), the compounds of the formula (Ia)

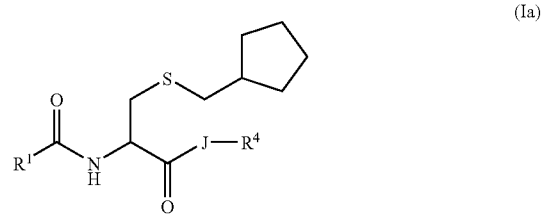

(Ia)

(wherein all the symbols are the same meanings as defined hereinbefore), the compounds of the formula (Ib)

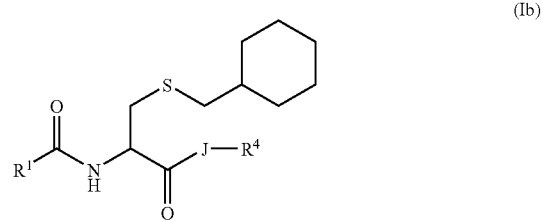

(Ib)

(wherein all the symbols are the same meanings as defined hereinbefore), the compounds of the formula (Ic)

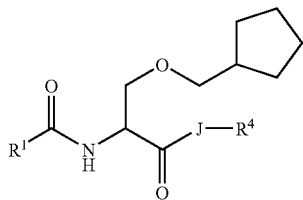
(Ic)

(wherein all the symbols are the same meanings as defined hereinbefore), the compounds of the formula (Id)

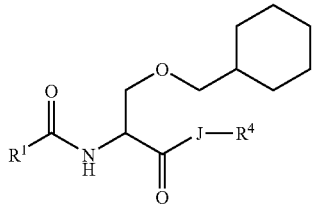
(Id)

(wherein all the symbols are the same meanings as defined hereinbefore), the compounds of the formula (Ie)

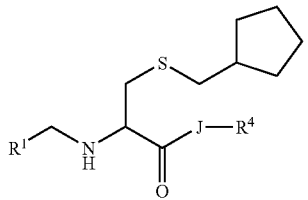
(Ie)

(wherein all the symbols are the same meanings as defined hereinbefore), the compounds of the formula (If)

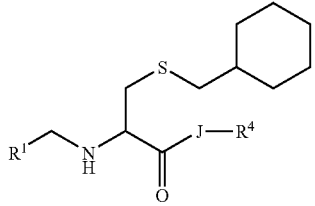
(If)

(wherein all the symbols are the same meanings as defined hereinbefore), the compounds of the formula (Ig)

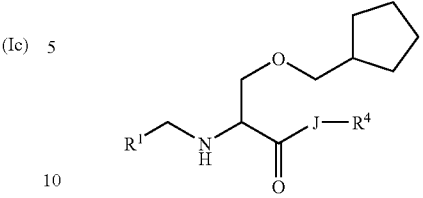
(Ig)

(wherein all the symbols are the same meanings as defined hereinbefore), and the compounds of the formula (Ih)

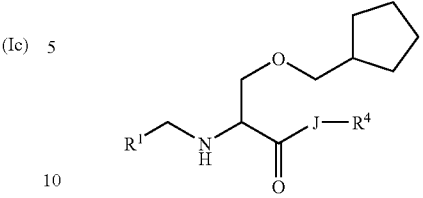
(Ih)

(wherein all the symbols are the same meanings as defined hereinbefore), non-toxic salts thereof, or hydrates thereof are preferable. The compounds of the formula (Ia) or (Ib) (wherein all the symbols are the same meanings as defined hereinbefore), non-toxic salts thereof, or hydrates thereof are preferable.

The concrete compounds are ones shown in the following Tables 1-40, non-toxic salts thereof and the hydrates thereof and ones described in Examples. Also, the following concrete compounds include the isomers generated by asymmetric carbon atom(s), i.e., R, S and RS form. In the following each Table, Me is methyl and $R^{54}$ is the same meaning of the substituent (i)-(xxiii) of the said heterocyclic ring.

TABLE 1

(Ia-1)

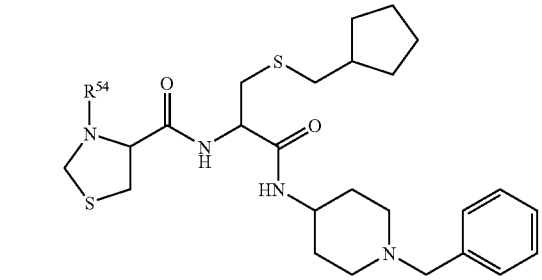

| No. | $R^{54}$ |
|---|---|
| 1 | 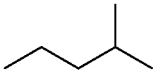 |

TABLE 1-continued
(Ia-1)
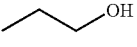
| No. | R⁵⁴ |
|---|---|
| 2 | 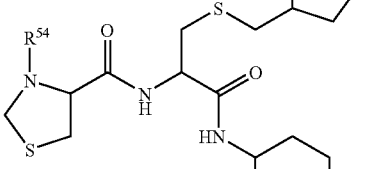 |
| 3 | 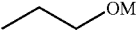 |
| 4 | 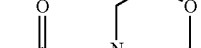 |
| 5 | 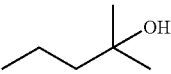 |
| 6 | 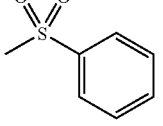 |
| 7 | 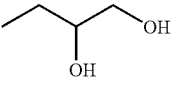 |
| 8 | 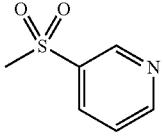 |
| 9 | 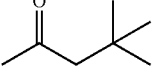 |
| 10 | 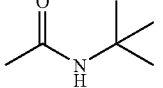 |
| 11 | 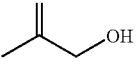 |
| 12 | 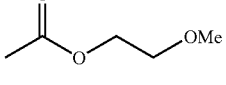 |
| 13 | 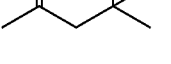 |
| 14 | 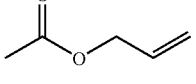 |
| 15 | 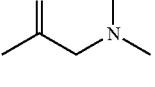 |
| 16 | 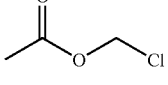 |
| 17 | 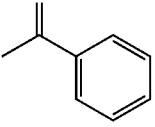 |
| 18 | 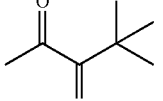 |
| 19 | 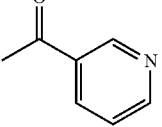 |
| 20 | 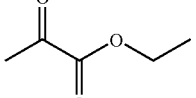 |
| 21 | 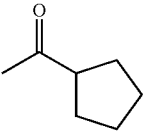 |
| 22 | 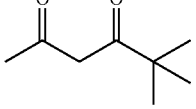 |

TABLE 1-continued (Ia-1)

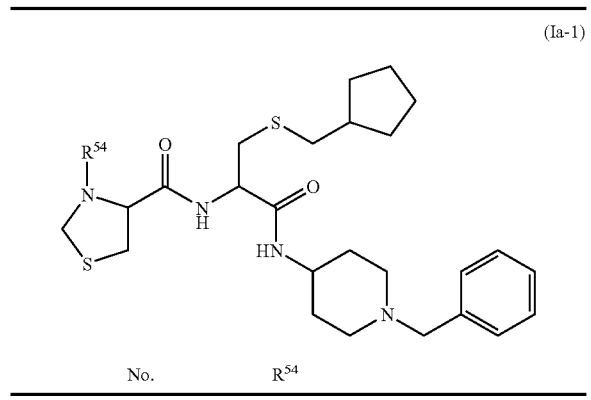

| No. | R⁵⁴ |
|---|---|
| 23 | propanoic acid |
| 24 | 1-morpholinopropan-1-one |

TABLE 2

(Ia-2)

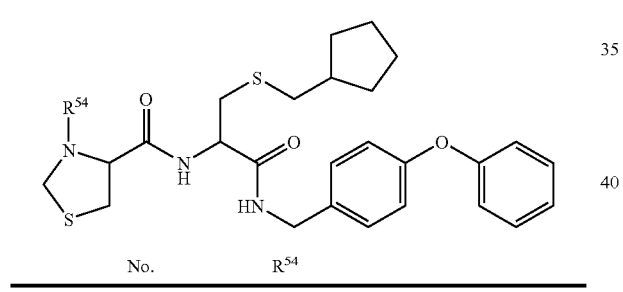

| No. | R⁵⁴ |
|---|---|
| 1 | isopentyl |
| 2 | 3-hydroxypropyl |
| 3 | 3-methoxypropyl |
| 4 | 3-hydroxy-3-methylbutyl |
| 5 | 2,3-dihydroxybutyl |
| 6 | 3,3-dimethyl-2-oxobutyl |
| 7 | 1-hydroxy-2-oxopropyl |

TABLE 2-continued (Ia-2)

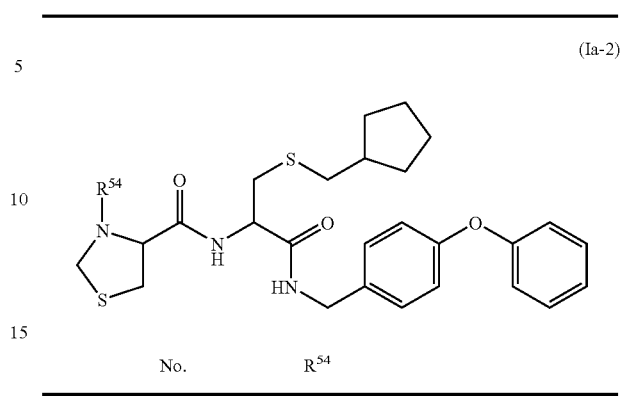

| No. | R⁵⁴ |
|---|---|
| 8 | 3-hydroxy-3-methyl-2-oxobutyl |
| 9 | 1-(dimethylamino)propan-2-one |
| 10 | phenacyl |
| 11 | 1-(pyridin-3-yl)ethanone |
| 12 | 1-cyclopentylethanone |
| 13 | 1-morpholino-2-oxopropyl |
| 14 | phenylmethanesulfonyl |
| 15 | pyridin-3-ylmethanesulfonyl |

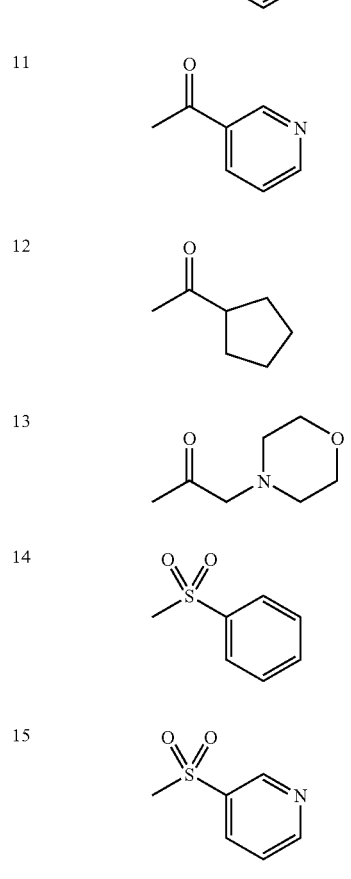

TABLE 2-continued (Ia-2)

Structure: Thiazolidine with R⁵⁴ on N, connected via C(O)NH to a cysteine-like residue with S-CH₂-cyclopentyl side chain, C(O)NH-CH₂-(4-phenoxyphenyl).

| No. | R⁵⁴ |
|---|---|
| 16 | CH₃-C(O)-NH-C(CH₃)₃ |
| 17 | CH₃-C(O)-O-CH₂CH₂-OMe |
| 18 | CH₃-C(O)-O-CH₂-CH=CH₂ (allyl ester) |
| 19 | CH₃-C(O)-O-CH₂-Cl |
| 20 | CH₃-C(O)-C(O)-C(CH₃)₃ |
| 21 | CH₃-C(O)-C(O)-O-ethyl |
| 22 | CH₃-C(O)-CH₂-C(O)-C(CH₃)₃ |
| 23 | CH₃CH₂-C(O)-OH |
| 24 | CH₃CH₂-C(O)-morpholine |

TABLE 3

(Ia-3)

Structure: Thiazolidine with R⁵⁴ on N, connected via C(O)NH to a cysteine-like residue with S-CH₂-cyclopentyl side chain, C(O)NH-CH₂-(4-methoxyphenyl-OCH₃).

| No. | R⁵⁴ |
|---|---|
| 1 | isopentyl (CH₂CH₂CH(CH₃)₂) |
| 2 | CH₂CH₂CH₂-OH |
| 3 | CH₂CH₂CH₂-OMe |
| 4 | CH₂CH₂-C(CH₃)₂-OH |
| 5 | CH₃CH₂-CH(OH)-CH₂-OH |
| 6 | CH₃-C(O)-CH₂-C(CH₃)₃ |
| 7 | CH₃-C(O)-CH₂-OH |
| 8 | CH₃-C(O)-CH₂-C(CH₃)₂-OH |
| 9 | CH₃-C(O)-CH₂-N(CH₃)₂ |
| 10 | CH₃-C(O)-phenyl |
| 11 | CH₃-C(O)-(3-pyridyl) |
| 12 | CH₃-C(O)-cyclopentyl |

TABLE 3-continued (Ia-3)

| No. | R⁵⁴ |
|---|---|
| 13 | (2-oxo-2-morpholinoethyl / morpholinylmethyl ketone group) |
| 14 | (methylsulfonylphenyl) |
| 15 | (methylsulfonylpyridin-3-yl) |
| 16 | (N-tert-butyl acetamide) |
| 17 | (2-methoxyethyl acetate) |
| 18 | (allyl acetate) |
| 19 | (chloromethyl acetate) |
| 20 | (1-(tert-butyl)-1,2-dioxopropyl) |
| 21 | (ethyl pyruvate) |
| 22 | (1-(tert-butyl)-1,3-dioxobutyl) |

TABLE 3-continued (Ia-3)

| No. | R⁵⁴ |
|---|---|
| 23 | (propionic acid) |
| 24 | (1-morpholino-1-oxopropyl) |

TABLE 4

(Ia-4)

| No. | R⁵⁴ |
|---|---|
| 1 | (isopentyl) |
| 2 | (3-hydroxypropyl) |
| 3 | (3-methoxypropyl) |
| 4 | (3-hydroxy-3-methylbutyl) |
| 5 | (2,3-dihydroxybutyl) |
| 6 | (3,3-dimethyl-2-oxobutyl) |
| 7 | (1-hydroxy-2-oxopropyl) |

TABLE 4-continued
(Ia-4)
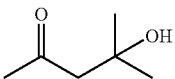
| No. | R⁵⁴ |
|---|---|
| 8 | 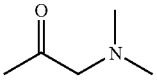 |
| 9 | 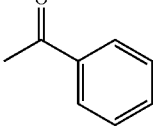 |
| 10 | 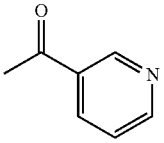 |
| 11 | 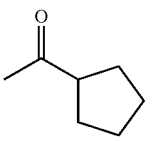 |
| 12 | 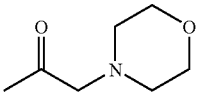 |
| 13 | 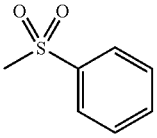 |
| 14 | 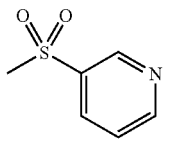 |
TABLE 4-continued
(Ia-4)
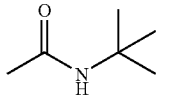
| No. | R⁵⁴ |
|---|---|
| 15 | 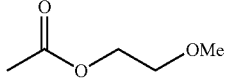 |
| 16 | 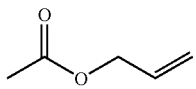 |
| 17 | 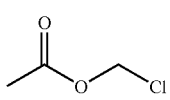 |
| 18 | 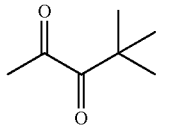 |
| 19 | 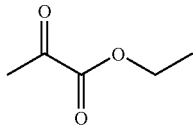 |
| 20 | 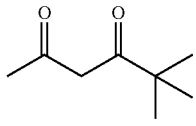 |
| 21 | |
| 22 | |

TABLE 4-continued (Ia-4)

[Structure: thiazolidine-N(R⁵⁴)-C(O)-NH-CH(CH₂-S-CH₂-cyclopentyl)-C(O)-NH-CH₂CH₂-NH-CH₂-phenyl]

| No. | R⁵⁴ |
|---|---|
| 23 | propanoic acid (CH₃CH₂-C(O)OH) |
| 24 | 1-(morpholin-4-yl)propan-1-one |

TABLE 5

(Ia-5)

[Structure: thiazolidine-N(R⁵⁴)-C(O)-NH-CH(CH₂-S-CH₂-cyclopentyl)-C(O)-N(piperidine-4-NH-CH₂-phenyl)]

| No. | R⁵⁴ |
|---|---|
| 1 | isopentyl (3-methylbutyl) |
| 2 | 3-hydroxypropyl (CH₃CH₂CH₂-OH shown with OH) |
| 3 | 3-methoxypropyl |
| 4 | 2-methyl-2-hydroxybutyl |
| 5 | 2,3-dihydroxybutyl |
| 6 | 3,3-dimethyl-2-oxobutyl (pinacolone-like) |

TABLE 5-continued (Ia-5)

| No. | R⁵⁴ |
|---|---|
| 7 | 1-hydroxyacetone (CH₃-C(O)-CH₂OH) |
| 8 | 4-hydroxy-4-methyl-2-pentanone analog |
| 9 | (dimethylamino)acetone |
| 10 | phenacyl (C(O)-phenyl) |
| 11 | 3-pyridyl ketone |
| 12 | cyclopentyl ketone |
| 13 | 1-morpholino-2-oxopropyl |
| 14 | phenylsulfonylmethyl (SO₂-phenyl) |
| 15 | (pyridin-3-yl)sulfonylmethyl |

TABLE 5-continued
(Ia-5)
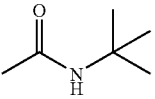
| No. | R⁵⁴ |
|---|---|
| 16 | 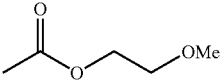 |
| 17 | 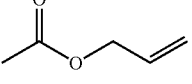 |
| 18 | 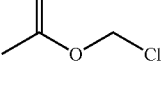 |
| 19 | 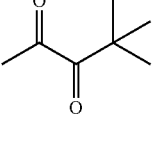 |
| 20 | 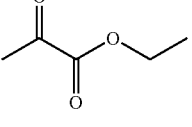 |
| 21 | 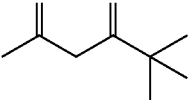 |
| 22 | 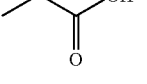 |
| 23 | 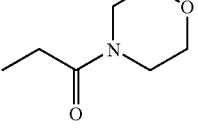 |
| 24 | 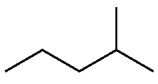 |
TABLE 6
(Ib-1)
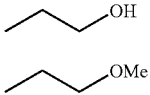
| No. | R⁵⁴ |
|---|---|
| 1 |  |
| 2 | 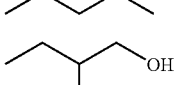 |
| 3 | 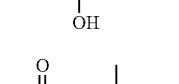 |
| 4 | 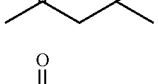 |
| 5 | 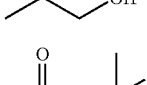 |
| 6 | 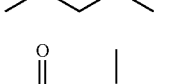 |
| 7 | 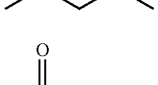 |
| 8 | 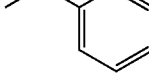 |
| 9 | 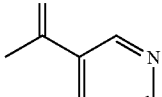 |
| 10 | 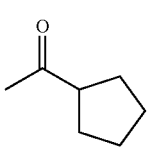 |
| 11 | |
| 12 | |

TABLE 6-continued (Ib-1)

| No. | R⁵⁴ |
|---|---|
| 13 | 2-oxo-propyl morpholine |
| 14 | methylsulfonyl benzene |
| 15 | methylsulfonyl pyridine |
| 16 | N-tert-butyl acetamide |
| 17 | 2-methoxyethyl acetate |
| 18 | allyl acetate |
| 19 | chloromethyl acetate |
| 20 | 1-(tert-butyl)-2-oxopropan-1-one |
| 21 | ethyl 2-oxopropanoate |

TABLE 6-continued (Ib-1)

| No. | R⁵⁴ |
|---|---|
| 22 | 2,2-dimethyl-hexane-3,5-dione |
| 23 | propanoic acid |
| 24 | 1-morpholinopropan-1-one |

TABLE 7

(Ib-2)

| No. | R⁵⁴ |
|---|---|
| 1 | isopentyl |
| 2 | 3-hydroxypropyl |
| 3 | 3-methoxypropyl |
| 4 | 2-methyl-2-hydroxypentyl |
| 5 | 2,3-dihydroxypentyl |

TABLE 7-continued
(Ib-2)
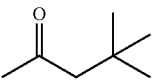
| No. | R⁵⁴ |
|---|---|
| 6 | 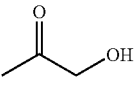 |
| 7 | 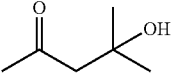 |
| 8 | 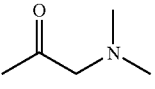 |
| 9 | 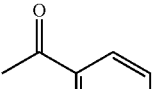 |
| 10 | 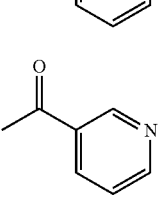 |
| 11 | 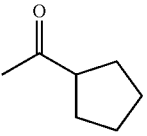 |
| 12 | 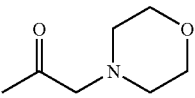 |
| 13 | 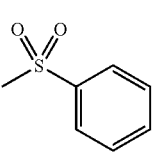 |
| 14 | 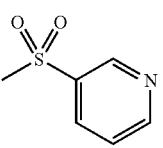 |
| 15 | 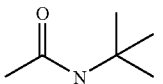 |
TABLE 7-continued
(Ib-2)
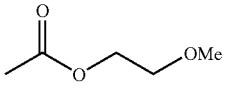
| No. | R⁵⁴ |
|---|---|
| 16 | 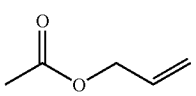 |
| 17 | 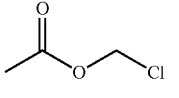 |
| 18 | 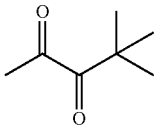 |
| 19 | 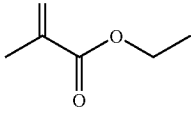 |
| 20 | 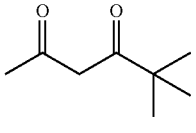 |
| 21 | 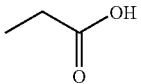 |
| 22 | 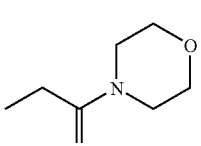 |
| 23 | 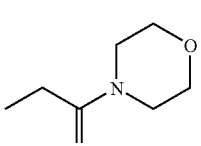 |
| 24 | 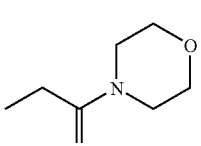 |

TABLE 8
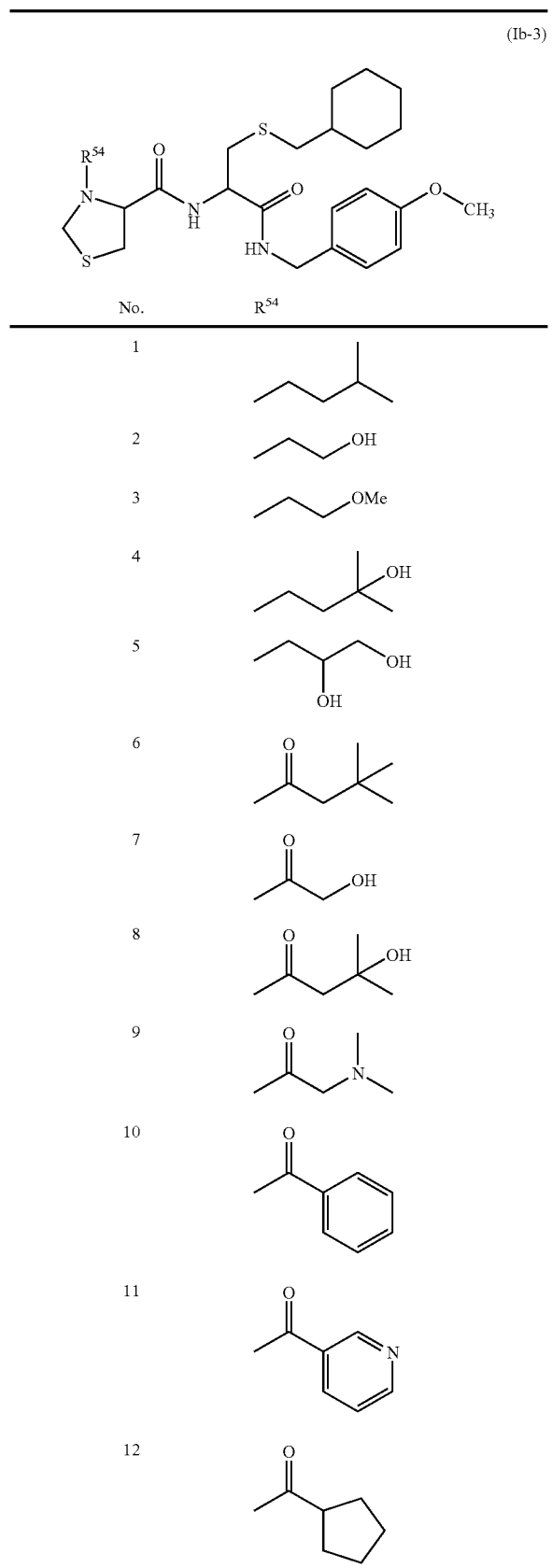
TABLE 8-continued
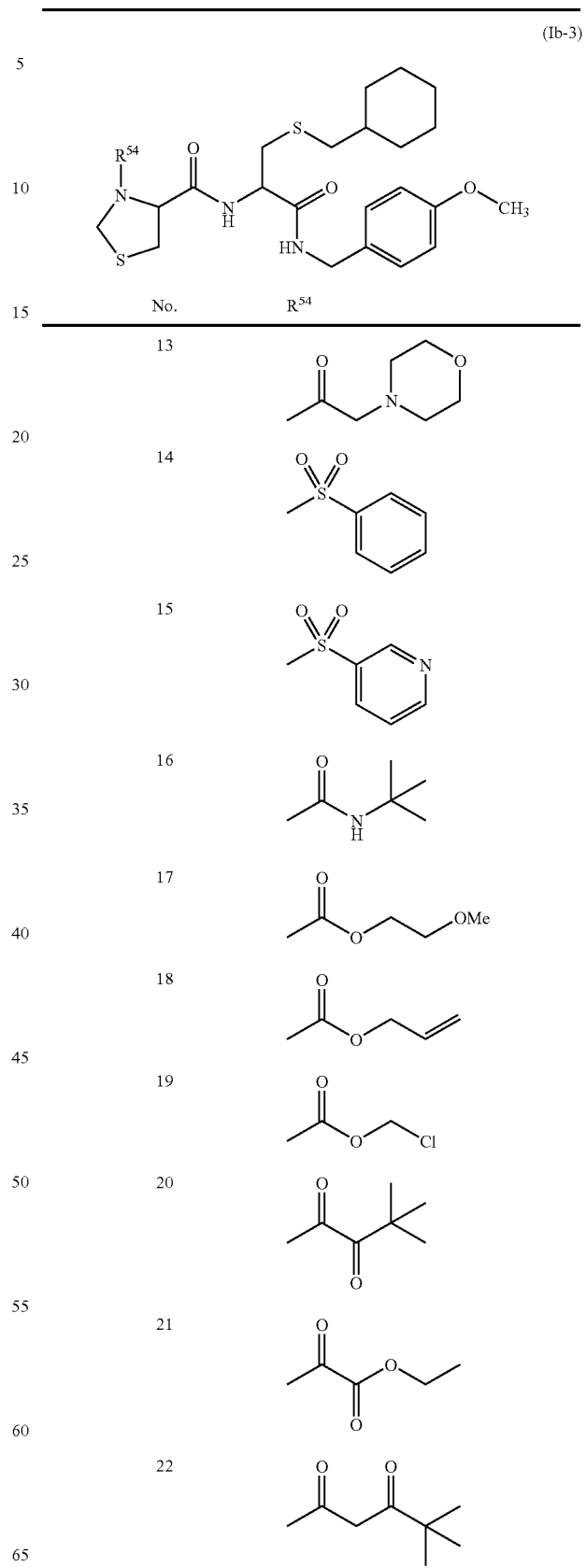

TABLE 8-continued
(Ib-3)
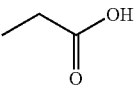
| No. | R⁵⁴ |
|---|---|
| 23 | 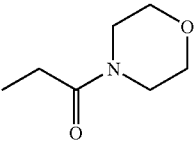 |
| 24 | 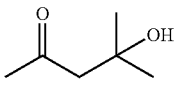 |
TABLE 9
(Ib-4)
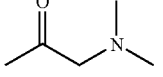
| No. | R⁵⁴ |
|---|---|
| 1 | 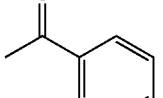 |
| 2 | 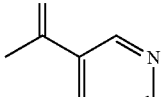 |
| 3 | 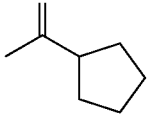 |
| 4 | 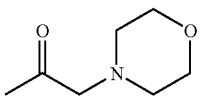 |
| 5 | 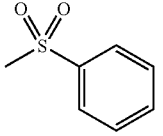 |
| 6 | 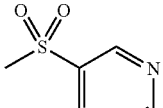 |
| 7 | 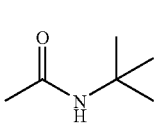 |
TABLE 9-continued
(Ib-4)
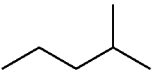
| No. | R⁵⁴ |
|---|---|
| 8 | 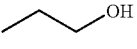 |
| 9 | 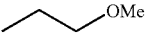 |
| 10 | 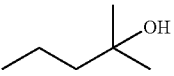 |
| 11 | 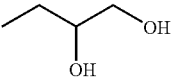 |
| 12 | 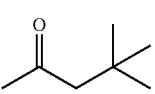 |
| 13 | 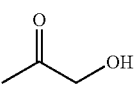 |
| 14 | |
| 15 | |
| 16 | |

TABLE 9-continued (Ib-4)

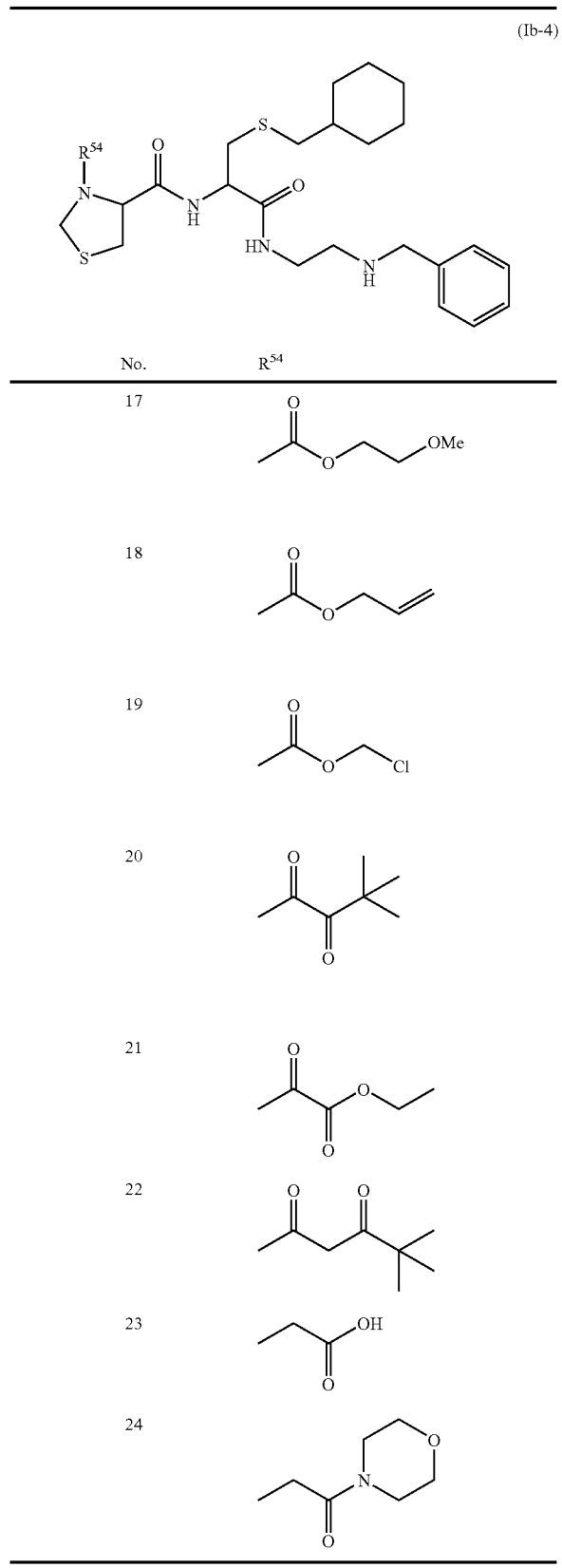

| No. | R[54] |
|---|---|
| 17 | (acetate-2-methoxyethyl) |
| 18 | (allyl acetate) |
| 19 | (chloromethyl acetate) |
| 20 | (1-pivaloyl-2-oxopropane) |
| 21 | (ethyl pyruvate) |
| 22 | (1-tert-butyl-1,3-dioxobutane) |
| 23 | (propanoic acid) |
| 24 | (3-morpholino-3-oxopropyl) |

TABLE 10

(Ib-5)

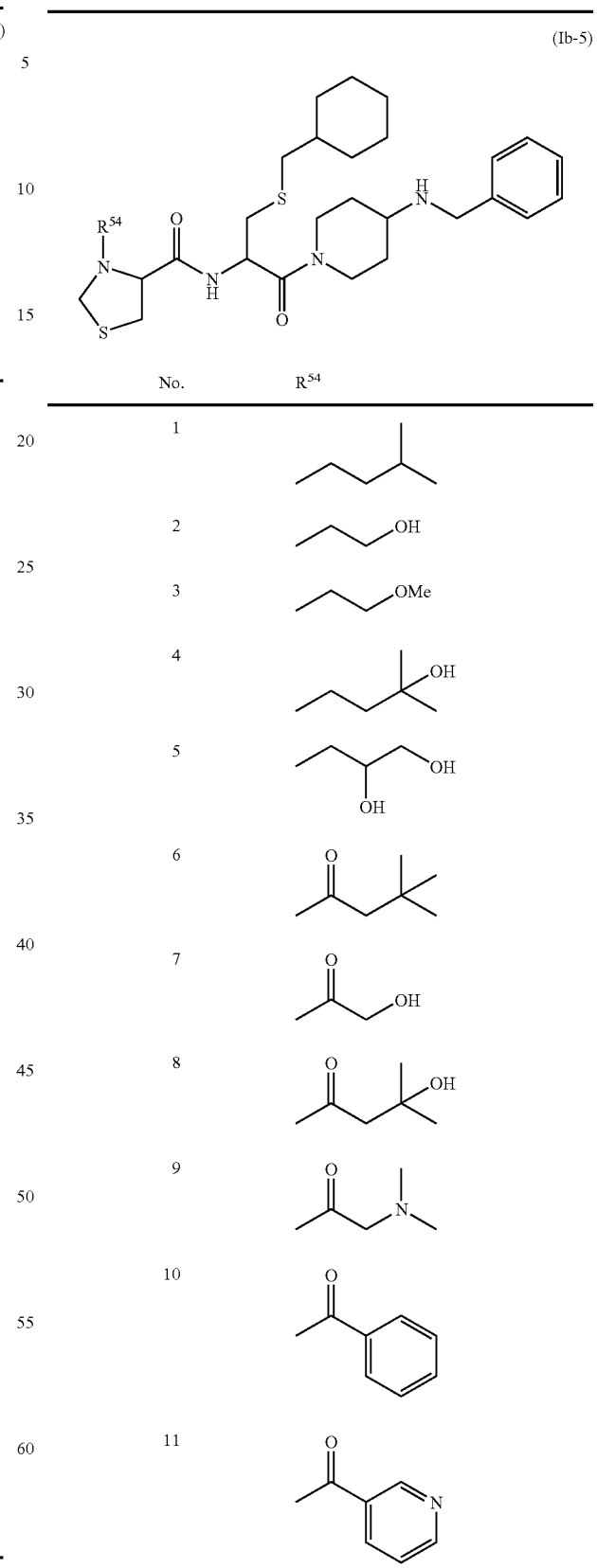

| No. | R[54] |
|---|---|
| 1 | (isopentyl) |
| 2 | (3-hydroxypropyl) |
| 3 | (3-methoxypropyl) |
| 4 | (2-methyl-2-hydroxypentyl) |
| 5 | (2,3-dihydroxybutyl) |
| 6 | (pivaloylmethyl) |
| 7 | (hydroxyacetonyl) |
| 8 | (4-hydroxy-4-methyl-2-oxopentyl) |
| 9 | (dimethylaminoacetonyl) |
| 10 | (phenacyl) |
| 11 | (3-pyridoyl methyl) |

TABLE 10-continued
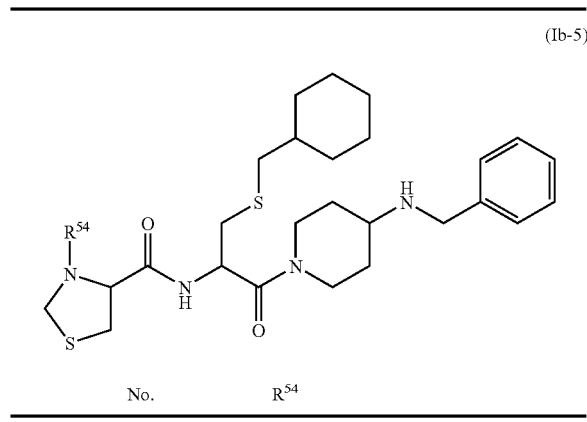
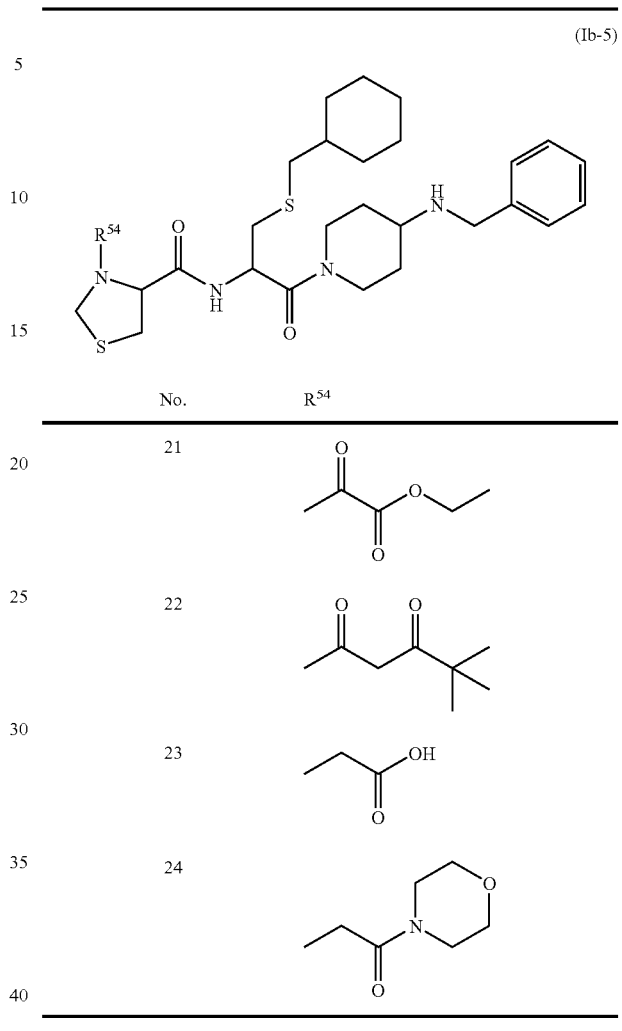
TABLE 11
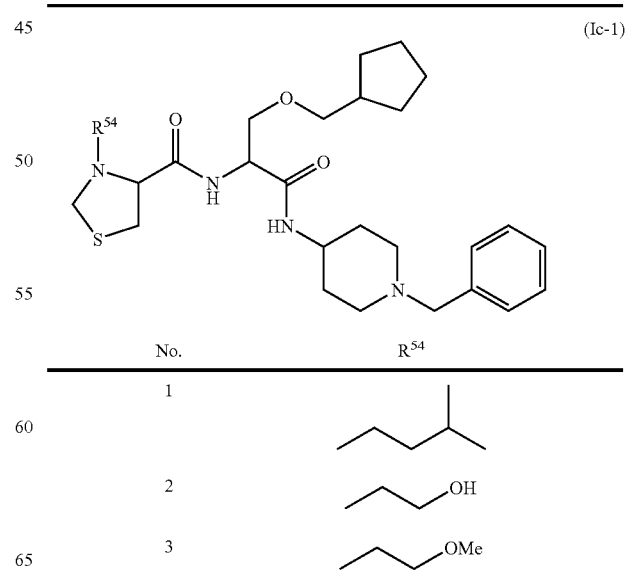

TABLE 11-continued (Ic-1)

| No. | R⁵⁴ |
|---|---|
| 4 | 2-methyl-2-hydroxypentyl |
| 5 | 2,3-dihydroxybutyl |
| 6 | 3,3-dimethyl-2-oxobutyl |
| 7 | 1-hydroxy-2-oxopropyl |
| 8 | 3-hydroxy-3-methyl-2-oxobutyl |
| 9 | 3-(dimethylamino)-2-oxopropyl |
| 10 | phenacyl |
| 11 | (pyridin-3-yl)carbonylmethyl |
| 12 | cyclopentylcarbonylmethyl |
| 13 | (morpholin-4-yl)acetyl |

TABLE 11-continued (Ic-1)

| No. | R⁵⁴ |
|---|---|
| 14 | phenylsulfonylmethyl (methylsulfonylphenyl) |
| 15 | (methylsulfonyl)pyridin-3-yl |
| 16 | N-tert-butylacetamide |
| 17 | 2-methoxyethyl acetate |
| 18 | allyl acetate |
| 19 | chloromethyl acetate |
| 20 | 3,3-dimethyl-2-oxobutanoyl |
| 21 | ethyl 2-oxopropanoate |
| 22 | 5,5-dimethyl-2,4-dioxohexyl |
| 23 | propanoic acid |

TABLE 11-continued
(Ic-1)
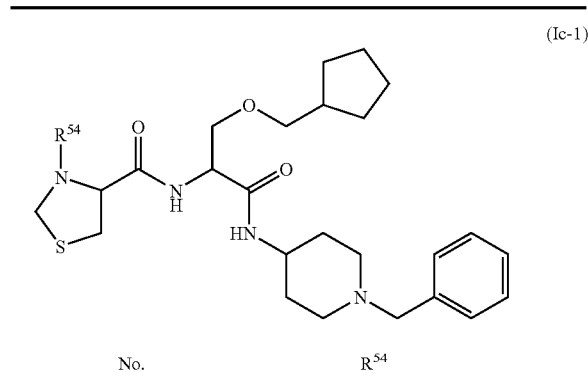
| No. | R⁵⁴ |
|---|---|
| 24 | 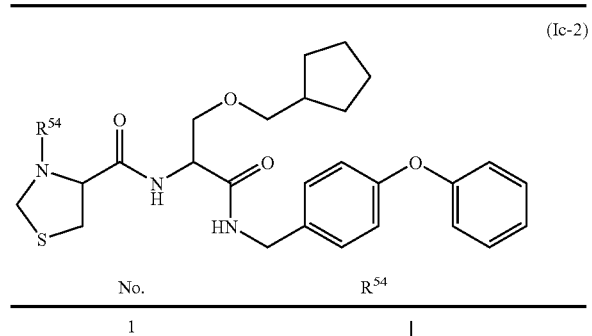 |
TABLE 12
(Ic-2)
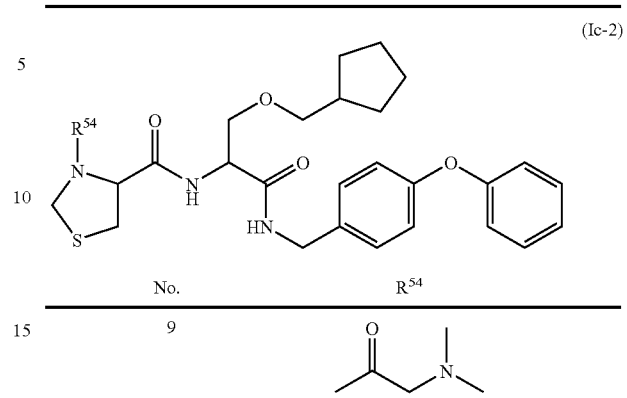
| No. | R⁵⁴ |
|---|---|
| 1 | |
| 2 | |
| 3 | |
| 4 | |
| 5 | |
| 6 | |
| 7 | |
| 8 | |
TABLE 12-continued
(Ic-2)
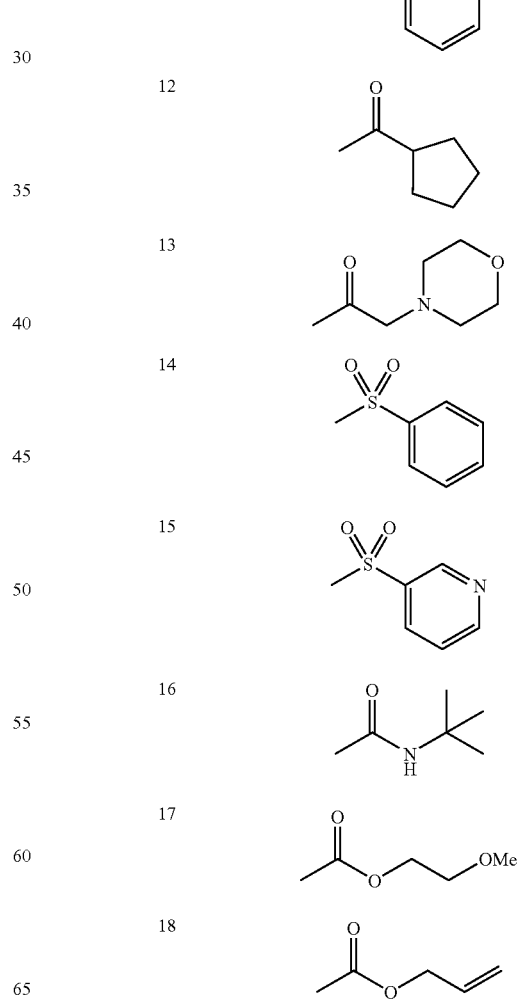
| No. | R⁵⁴ |
|---|---|
| 9 | (dimethylaminoacetyl) |
| 10 | (benzoyl) |
| 11 | (nicotinoyl) |
| 12 | (cyclopentylcarbonyl) |
| 13 | (morpholinoacetyl) |
| 14 | (phenylsulfonylmethyl) |
| 15 | (pyridylsulfonylmethyl) |
| 16 | (tert-butylcarbamoylmethyl) |
| 17 | (2-methoxyethoxycarbonylmethyl) |
| 18 | (allyloxycarbonylmethyl) |

TABLE 12-continued
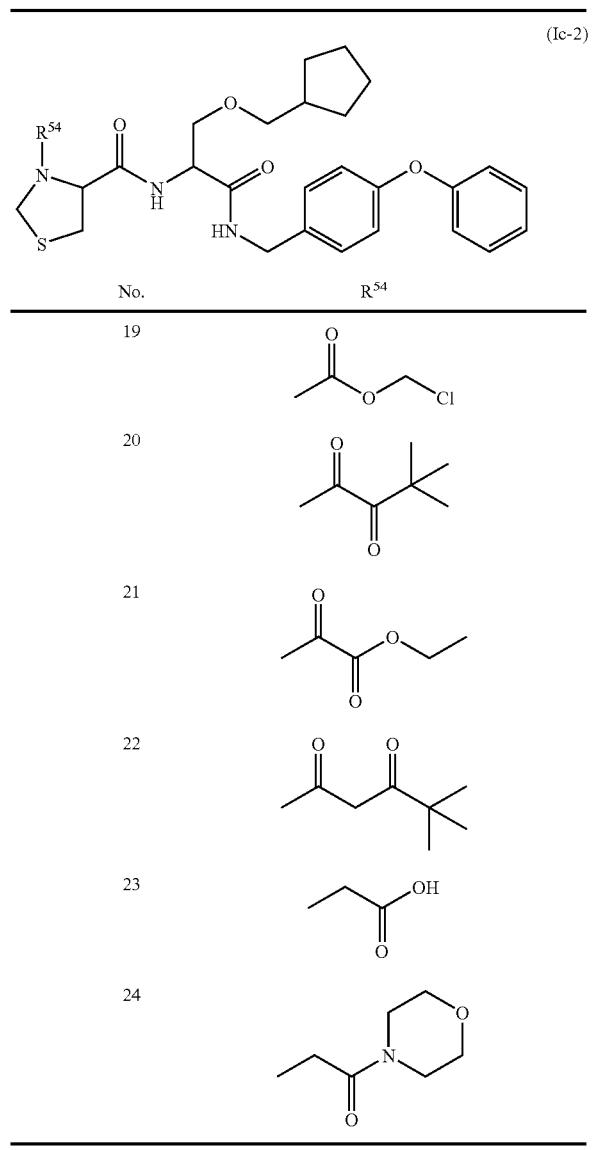
TABLE 13
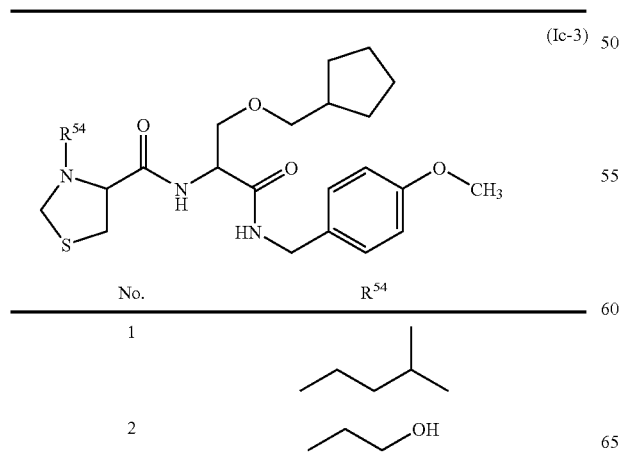
TABLE 13-continued
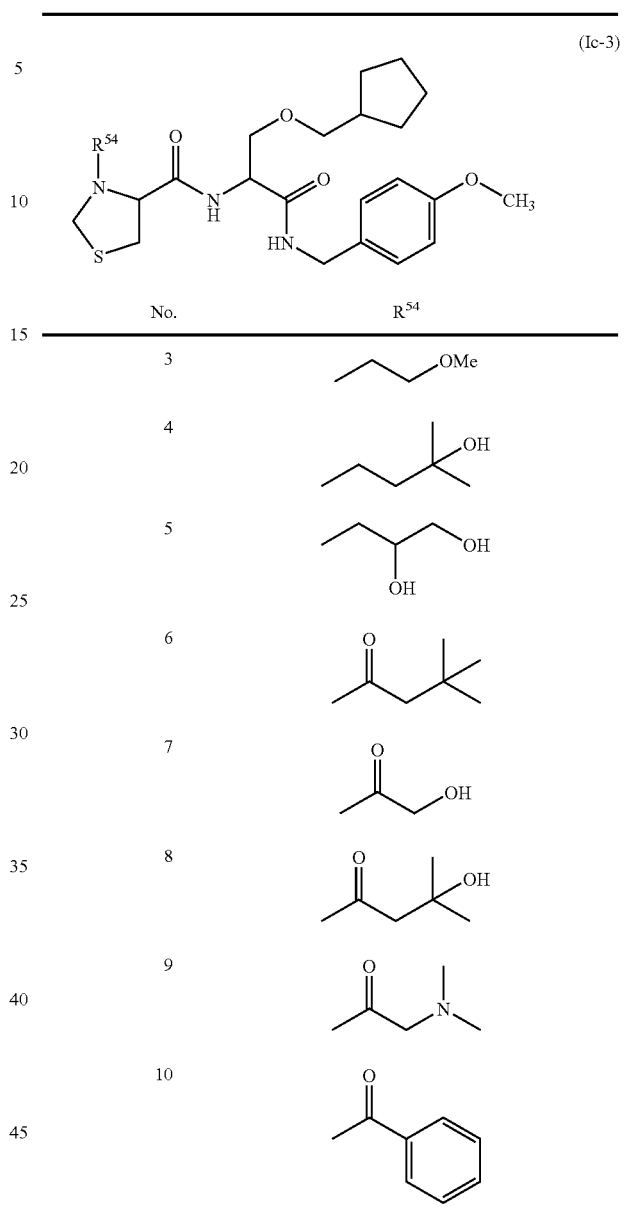

TABLE 13-continued (Ic-3)

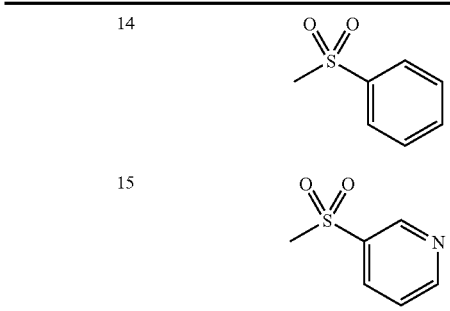

| No. | R⁵⁴ |
|---|---|
| 14 | methylsulfonylphenyl |
| 15 | methylsulfonylpyridinyl |
| 16 | N-tert-butyl acetamide |
| 17 | 2-methoxyethyl acetate |
| 18 | allyl acetate |
| 19 | chloromethyl acetate |
| 20 | 1-(tert-butyl)-1,2-propanedione |
| 21 | ethyl pyruvate |
| 22 | 5,5-dimethyl-2,4-hexanedione |
| 23 | propanoic acid |

TABLE 13-continued (Ic-3)

| No. | R⁵⁴ |
|---|---|
| 24 | 1-morpholinopropan-1-one |

TABLE 14

(Ic-4)

| No. | R⁵⁴ |
|---|---|
| 1 | isopentyl |
| 2 | 3-hydroxypropyl |
| 3 | 3-methoxypropyl |
| 4 | 2-methyl-2-hydroxypentyl |
| 5 | 2,3-dihydroxybutyl |
| 6 | 3,3-dimethyl-2-butanone |

TABLE 14-continued (Ic-4)

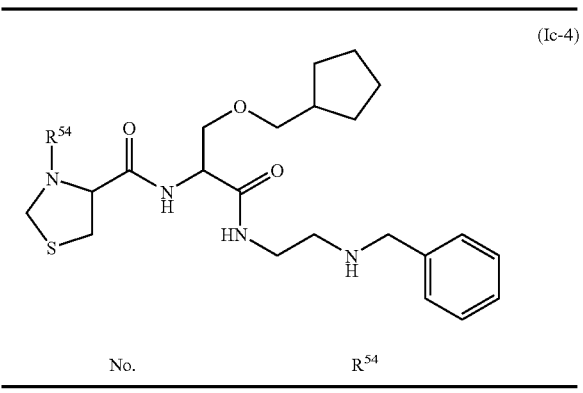

| No. | R⁵⁴ |
|---|---|
| 7 | 2-oxopropyl with OH (hydroxyacetone-derived acyl) |
| 8 | 3-hydroxy-3-methyl-butanoyl |
| 9 | (dimethylamino)acetone-derived acyl |
| 10 | benzoyl-methyl (phenacyl-type) |
| 11 | pyridin-3-yl carbonyl-methyl |
| 12 | cyclopentyl carbonyl-methyl |
| 13 | morpholinoacetone-derived acyl |
| 14 | phenylsulfonyl-methyl |
| 15 | (pyridin-3-yl)sulfonyl-methyl |

TABLE 14-continued (Ic-4)

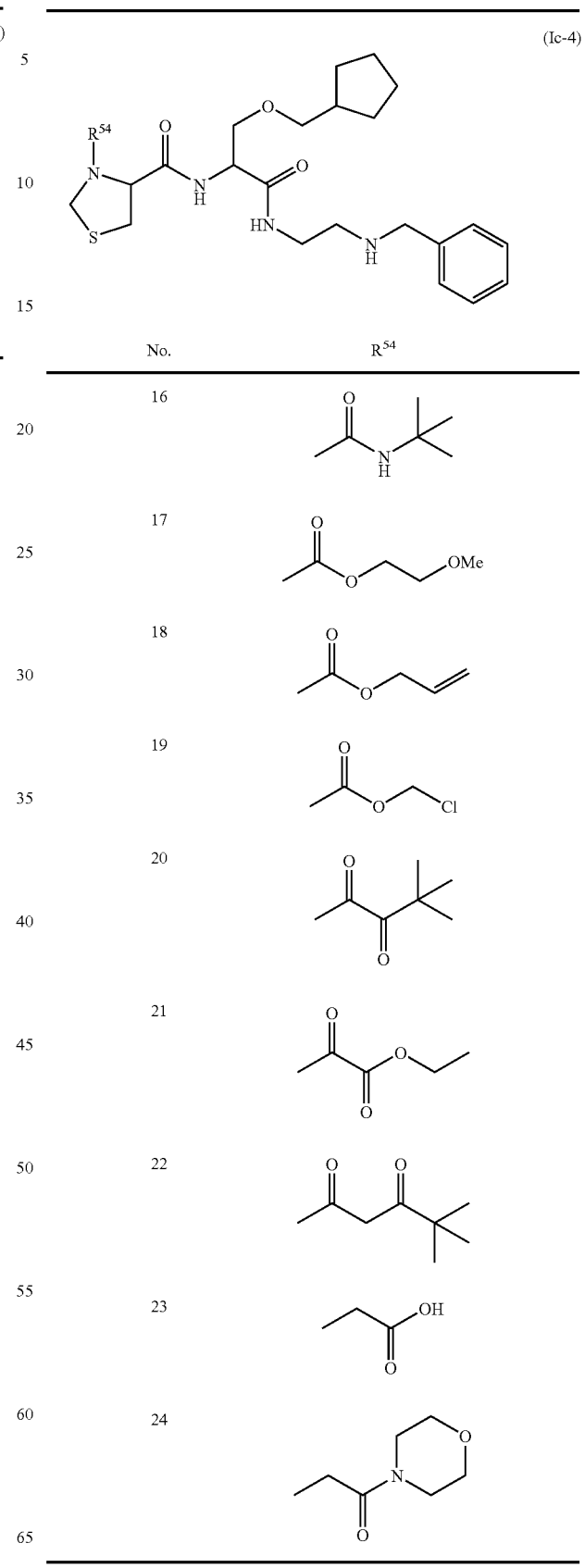

| No. | R⁵⁴ |
|---|---|
| 16 | N-tert-butyl acetamide |
| 17 | 2-methoxyethyl acetate |
| 18 | allyl acetate |
| 19 | chloromethyl acetate |
| 20 | 3,3-dimethyl-2-oxobutanoyl (pivaloyl-acetyl) |
| 21 | ethyl 2-oxopropanoate (ethyl pyruvate) |
| 22 | 5,5-dimethyl-2,4-dioxohexanoyl |
| 23 | propanoic acid |
| 24 | 1-morpholino-propan-1-one (propionyl morpholine) |

TABLE 15

(Ic-5)

Structure: Thiazolidine-N(R⁵⁴)-C(=O)-NH-CH(CH₂-O-CH₂-cyclopentyl)-C(=O)-N(piperidine-4-NH-CH₂-phenyl)

| No. | R⁵⁴ |
|---|---|
| 1 | isopentyl (CH(CH₃)CH₂CH₂CH₃ branch) |
| 2 | -CH₂CH₂CH₂OH |
| 3 | -CH₂CH₂CH₂OMe |
| 4 | -CH₂CH₂C(CH₃)₂OH |
| 5 | -CH₂CH(OH)CH₂OH (with ethyl) |
| 6 | -C(=O)CH₂C(CH₃)₃ |
| 7 | -C(=O)CH₂OH |
| 8 | -C(=O)CH₂C(CH₃)₂OH |
| 9 | -C(=O)CH₂N(CH₃)₂ |
| 10 | -C(=O)-phenyl |
| 11 | -C(=O)-(3-pyridyl) |
| 12 | -C(=O)-cyclopentyl |

TABLE 15-continued (Ic-5)

| No. | R⁵⁴ |
|---|---|
| 13 | -C(=O)CH₂-(morpholin-4-yl) |
| 14 | -S(=O)₂-phenyl (with Me) |
| 15 | -S(=O)₂-(3-pyridyl) (with Me) |
| 16 | -C(=O)NH-C(CH₃)₃ |
| 17 | -C(=O)O-CH₂CH₂-OMe |
| 18 | -C(=O)O-CH₂CH=CH₂ |
| 19 | -C(=O)O-CH₂Cl |
| 20 | -C(=O)C(=O)C(CH₃)₃ |
| 21 | -C(=O)C(=O)O-CH₂CH₃ |
| 22 | -C(=O)CH₂C(=O)C(CH₃)₃ |

TABLE 15-continued (Ic-5)

| No. | R⁵⁴ |
|---|---|
| 23 | propanoic acid |
| 24 | 1-morpholinopropan-1-one |

TABLE 16

(Id-1)

| No. | R⁵⁴ |
|---|---|
| 1 | 2-methylpentyl |
| 2 | 3-hydroxypropyl |
| 3 | 3-methoxypropyl |
| 4 | 2-methyl-2-hydroxypentyl |
| 5 | 2,3-dihydroxybutyl |
| 6 | 4,4-dimethyl-3-oxopentyl |

TABLE 16-continued (Id-1)

| No. | R⁵⁴ |
|---|---|
| 7 | 1-hydroxypropan-2-one |
| 8 | 4-hydroxy-4-methylpentan-2-one |
| 9 | 1-(dimethylamino)propan-2-one |
| 10 | 1-phenylethanone |
| 11 | 1-(pyridin-3-yl)ethanone |
| 12 | 1-cyclopentylethanone |
| 13 | 1-morpholinopropan-2-one |
| 14 | methyl phenyl sulfone |
| 15 | methyl pyridin-3-yl sulfone |

TABLE 16-continued (Id-1)

[Structure: R⁵⁴-N-thiazolidine-C(O)-NH-CH(CH₂-O-CH₂-cyclohexyl)-C(O)-NH-(4-piperidinyl)-N-CH₂-phenyl]

| No. | R⁵⁴ |
|---|---|
| 16 | CH₃-C(O)-NH-C(CH₃)₃ |
| 17 | CH₃-C(O)-O-CH₂CH₂-OMe |
| 18 | CH₃-C(O)-O-CH₂-CH=CH₂ |
| 19 | CH₃-C(O)-O-CH₂-Cl |
| 20 | CH₃-C(O)-C(O)-C(CH₃)₃ |
| 21 | CH₃-C(O)-C(O)-O-CH₂CH₃ |
| 22 | CH₃-C(O)-CH₂-C(O)-C(CH₃)₃ |
| 23 | CH₃CH₂-C(O)-OH |
| 24 | CH₃CH₂-C(O)-morpholine |

TABLE 17

(Id-2)

[Structure: R⁵⁴-N-thiazolidine-C(O)-NH-CH(CH₂-O-CH₂-cyclohexyl)-C(O)-NH-CH₂-(4-phenoxyphenyl)]

| No. | R⁵⁴ |
|---|---|
| 1 | isopentyl (CH₂CH₂CH(CH₃)₂) |
| 2 | CH₂CH₂CH₂-OH |
| 3 | CH₂CH₂CH₂-OMe |
| 4 | CH₂CH₂-C(CH₃)₂-OH |
| 5 | CH₃CH₂-CH(OH)-CH₂-OH |
| 6 | CH₃-C(O)-CH₂-C(CH₃)₃ |
| 7 | CH₃-C(O)-CH₂-OH |
| 8 | CH₃-C(O)-CH₂-C(CH₃)₂-OH |
| 9 | CH₃-C(O)-CH₂-N(CH₃)₂ |
| 10 | CH₃-C(O)-phenyl |
| 11 | CH₃-C(O)-(3-pyridyl) |
| 12 | CH₃-C(O)-cyclopentyl |

TABLE 17-continued (Id-2)

[Structure: R⁵⁴-N-thiazolidine-C(O)-NH-CH(CH₂-O-CH₂-cyclohexyl)-C(O)-NH-CH₂-C₆H₄-O-C₆H₅]

| No. | R⁵⁴ |
|---|---|
| 13 | CH₃-C(O)-CH₂-N(morpholine) |
| 14 | CH₃-S(O)₂-phenyl |
| 15 | CH₃-S(O)₂-pyridin-3-yl |
| 16 | CH₃-C(O)-NH-C(CH₃)₃ |
| 17 | CH₃-C(O)-O-CH₂CH₂-OMe |
| 18 | CH₃-C(O)-O-CH₂-CH=CH₂ |
| 19 | CH₃-C(O)-O-CH₂-Cl |
| 20 | CH₃-C(O)-C(O)-C(CH₃)₃ |
| 21 | CH₃-C(O)-C(O)-O-Et |
| 22 | CH₃-C(O)-CH₂-C(O)-C(CH₃)₃ |
| 23 | CH₃CH₂-COOH |
| 24 | CH₃CH₂-C(O)-N(morpholine) |

TABLE 18

(Id-3)

[Structure: R⁵⁴-N-thiazolidine-C(O)-NH-CH(CH₂-O-CH₂-cyclohexyl)-C(O)-NH-CH₂-C₆H₄-O-CH₃]

| No. | R⁵⁴ |
|---|---|
| 1 | isopentyl |
| 2 | CH₃CH₂CH₂-OH |
| 3 | CH₃CH₂CH₂-OMe |
| 4 | CH₃CH₂-C(CH₃)₂-OH |
| 5 | CH₃CH₂-CH(OH)-CH₂-OH |
| 6 | CH₃-C(O)-CH₂-C(CH₃)₃ |
| 7 | CH₃-C(O)-CH₂-OH |
| 8 | CH₃-C(O)-C(CH₃)₂-OH |

TABLE 18-continued
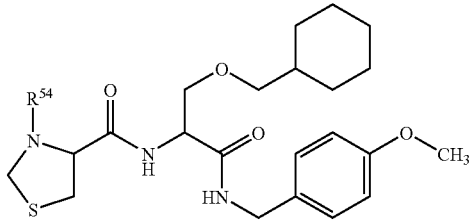
(Id-3)
| No. | R⁵⁴ |
|---|---|
| 9 | 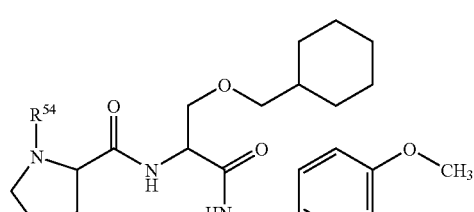 |
| 10 | 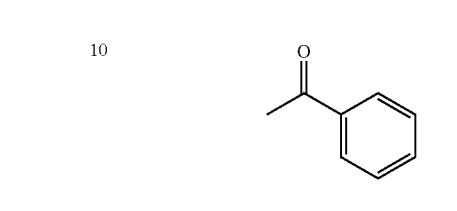 |
| 11 | 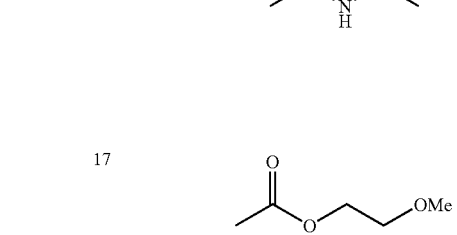 |
| 12 | 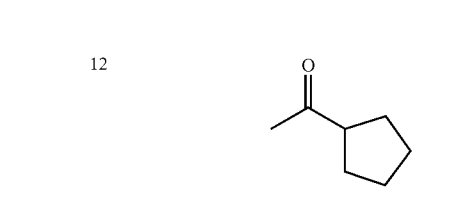 |
| 13 | 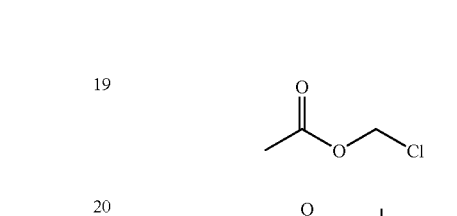 |
| 14 | 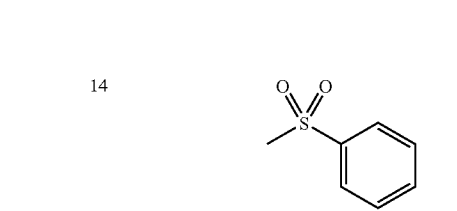 |
| 15 | 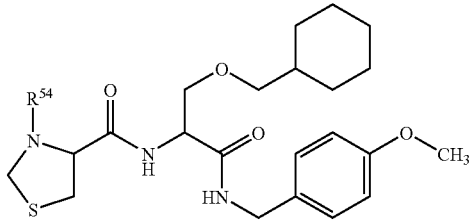 |
| 16 | 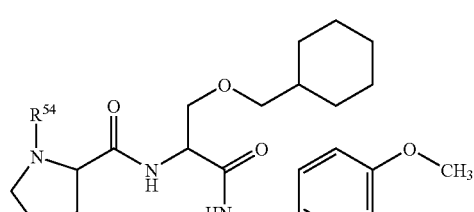 |
| 17 | 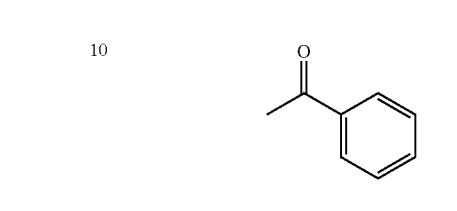 |
| 18 | 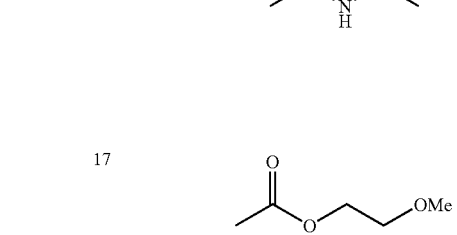 |
| 19 | 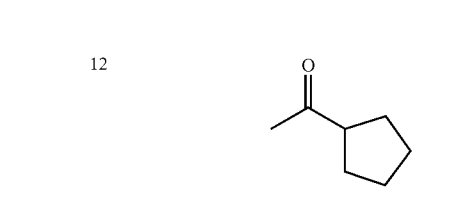 |
| 20 | 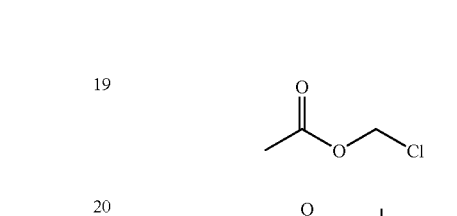 |
| 21 | 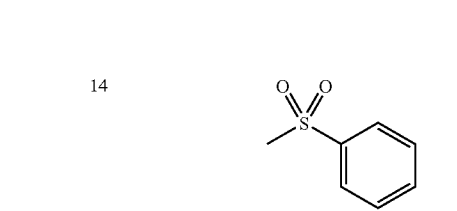 |
| 22 | 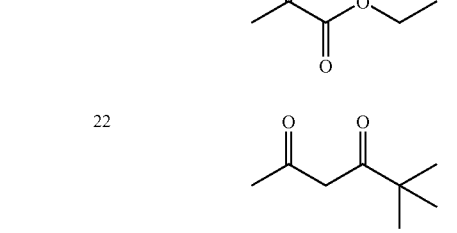 |
| 23 |  |

TABLE 18-continued

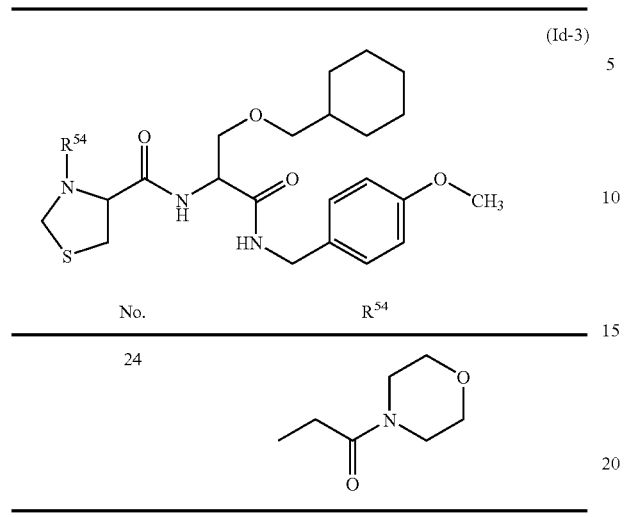

| No. | R⁵⁴ |
|---|---|
| 24 | (morpholine propanoyl group) |

TABLE 19

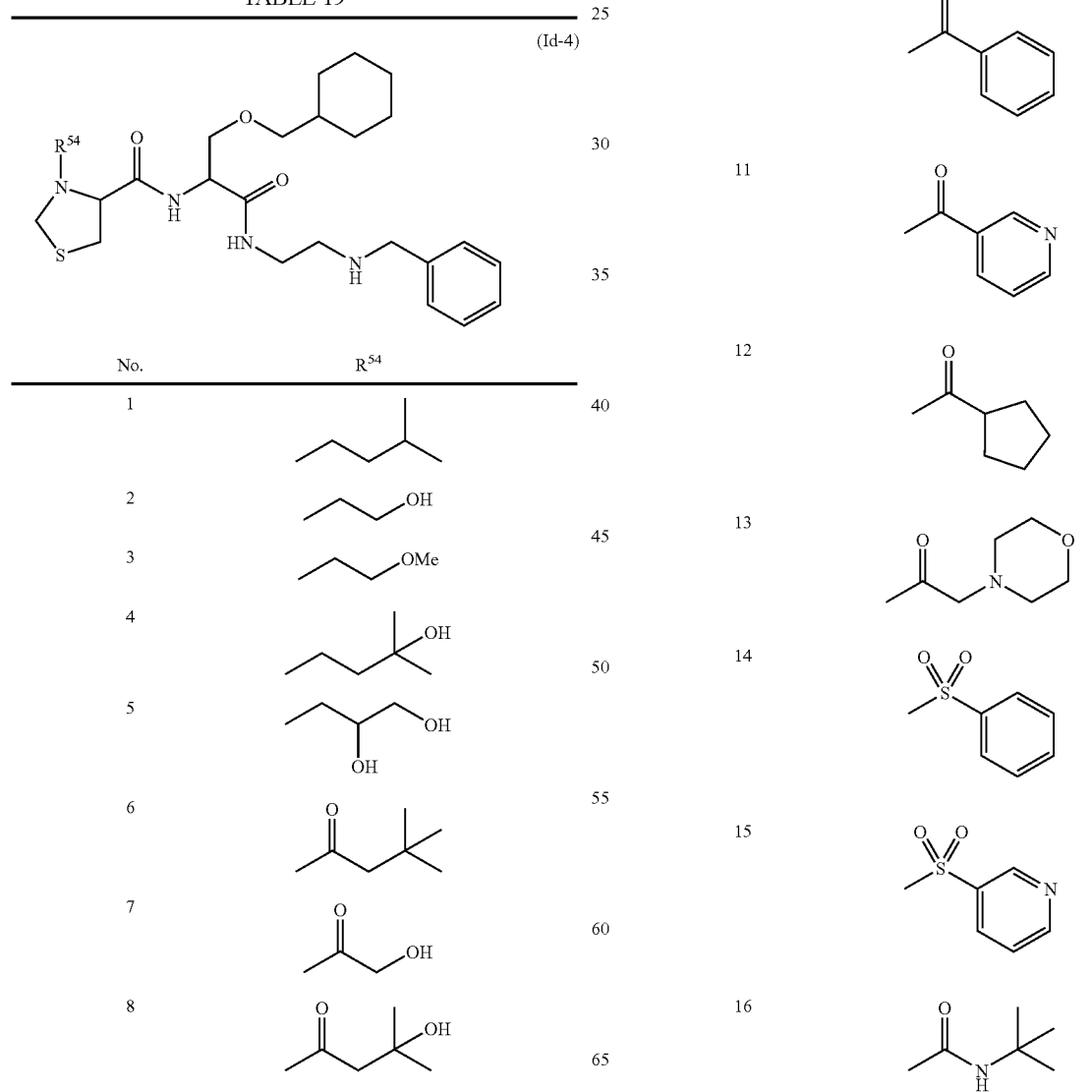

| No. | R⁵⁴ |
|---|---|
| 1 | (isopentyl) |
| 2 | (propyl-OH) |
| 3 | (propyl-OMe) |
| 4 | (2-methyl-2-hydroxybutyl) |
| 5 | (2,3-dihydroxybutyl) |
| 6 | (4,4-dimethyl-2-oxopentyl) |
| 7 | (hydroxyacetone) |
| 8 | (4-hydroxy-4-methyl-2-oxopentyl) |

TABLE 19-continued

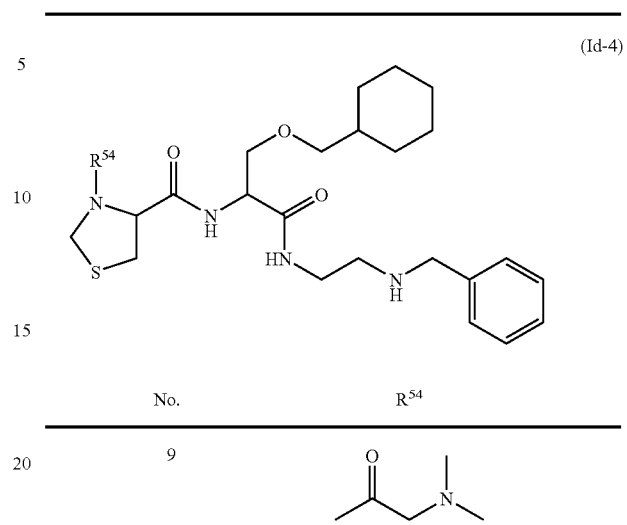

| No. | R⁵⁴ |
|---|---|
| 9 | (N,N-dimethylaminoacetone) |
| 10 | (acetophenone) |
| 11 | (3-acetylpyridine) |
| 12 | (cyclopentyl methyl ketone) |
| 13 | (morpholinoacetone) |
| 14 | (phenyl methyl sulfone) |
| 15 | (3-(methylsulfonyl)pyridine) |
| 16 | (N-tert-butylacetamide) |

TABLE 19-continued (Id-4)

| No. | R⁵⁴ |
|---|---|
| 17 | CH₃C(O)OCH₂CH₂OMe |
| 18 | CH₃C(O)OCH₂CH=CH₂ (allyl acetate) |
| 19 | CH₃C(O)OCH₂Cl |
| 20 | CH₃C(O)C(O)C(CH₃)₃ |
| 21 | CH₃C(O)C(O)OEt |
| 22 | CH₃C(O)CH₂C(O)C(CH₃)₃ |
| 23 | CH₃CH₂COOH |
| 24 | morpholine-N-C(O)CH₂CH₃ |

TABLE 20

(Id-5)

| No. | R⁵⁴ |
|---|---|
| 1 | isopentyl (3-methylbutyl) |
| 2 | HOCH₂CH₂CH₂– |
| 3 | MeOCH₂CH₂CH₂– |
| 4 | (CH₃)₂C(OH)CH₂CH₂CH₃ |
| 5 | CH₃CH₂CH(OH)CH₂OH |
| 6 | CH₃C(O)CH₂C(CH₃)₃ |
| 7 | CH₃C(O)CH₂OH |
| 8 | CH₃C(O)CH₂C(CH₃)₂OH |
| 9 | CH₃C(O)CH₂N(CH₃)₂ |
| 10 | C₆H₅C(O)CH₃ |
| 11 | 3-pyridyl-C(O)CH₃ |
| 12 | cyclopentyl-C(O)CH₃ |

TABLE 20-continued
(Id-5)
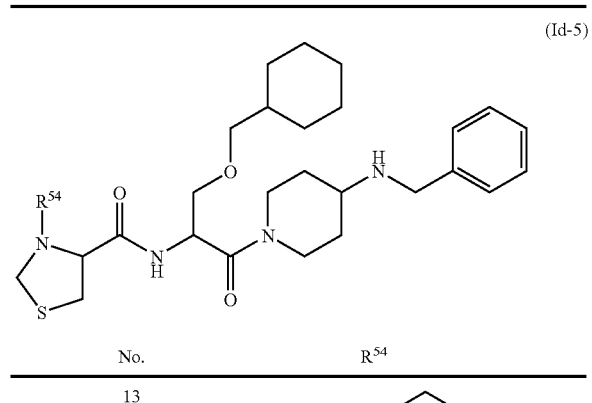
| No. | R⁵⁴ |
|---|---|
| 13 | 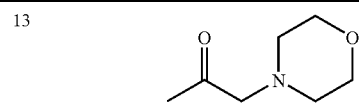 |
| 14 | 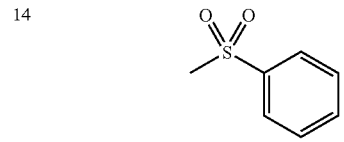 |
| 15 | 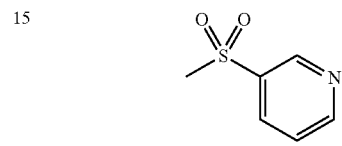 |
| 16 | 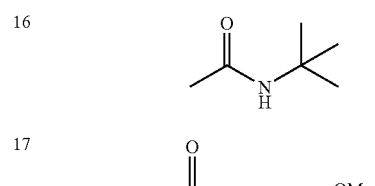 |
| 17 | 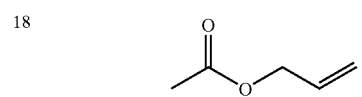 |
| 18 | 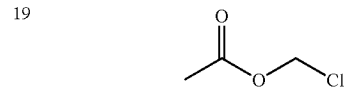 |
| 19 | 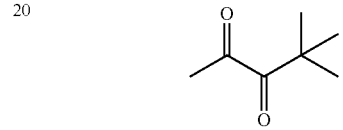 |
| 20 | 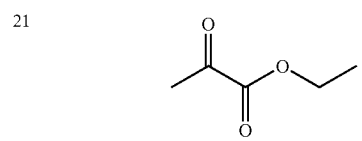 |
| 21 | 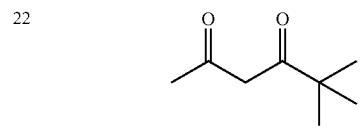 |
| 22 | |
TABLE 20-continued
(Id-5)
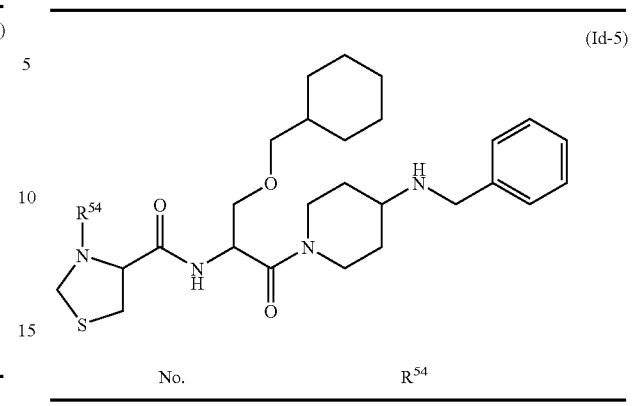
| No. | R⁵⁴ |
|---|---|
| 23 | 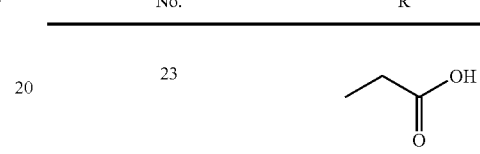 |
| 24 | 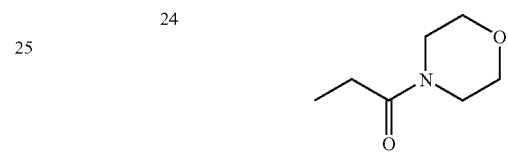 |
TABLE 21
(Ie-1)
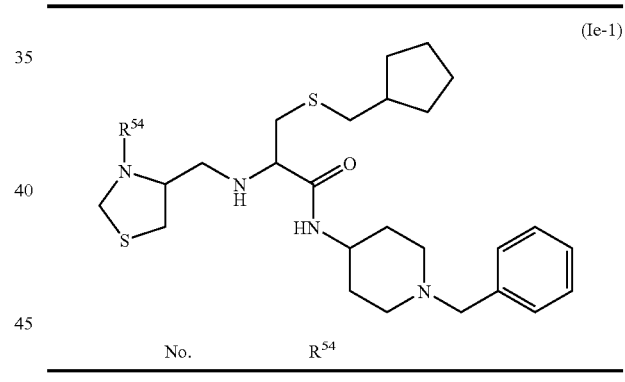
| No. | R⁵⁴ |
|---|---|
| 1 | 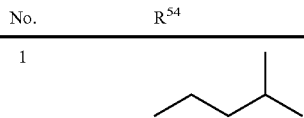 |
| 2 | 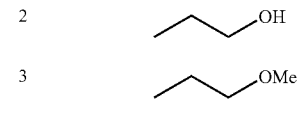 |
| 3 | 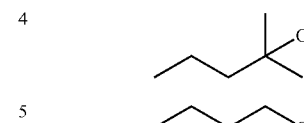 |
| 4 | 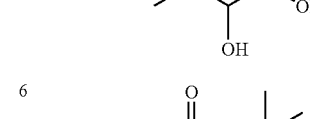 |
| 5 | 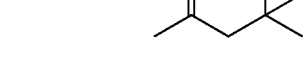 |
| 6 |  |

TABLE 21-continued (Ie-1)

| No. | R⁵⁴ |
|---|---|
| 7 | acetol (CH₃C(O)CH₂OH) |
| 8 | 4-hydroxy-4-methylpentan-2-one type (CH₃C(O)CH₂C(CH₃)₂OH) |
| 9 | 1-(dimethylamino)propan-2-one (CH₃C(O)CH₂N(CH₃)₂) |
| 10 | acetophenone |
| 11 | 1-(pyridin-3-yl)ethanone |
| 12 | 1-cyclopentylethanone |
| 13 | 1-morpholinopropan-2-one |
| 14 | methylsulfonylbenzene |
| 15 | 3-(methylsulfonyl)pyridine |
| 16 | N-tert-butylacetamide |
| 17 | 2-methoxyethyl acetate |
| 18 | allyl acetate |
| 19 | chloromethyl acetate |
| 20 | 3,3-dimethylbutane-2,3-dione type |
| 21 | ethyl 2-oxopropanoate |
| 22 | 5,5-dimethylhexane-2,4-dione |
| 23 | propionic acid |
| 24 | 1-morpholinopropan-1-one |

TABLE 22
(Ie-2)
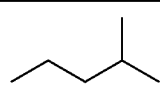
| No. | R⁵⁴ |
|---|---|
| 1 | 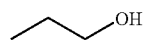 |
| 2 | 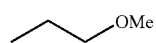 |
| 3 | 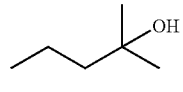 |
| 4 | 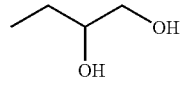 |
| 5 | 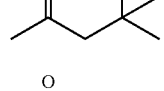 |
| 6 | 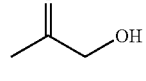 |
| 7 | 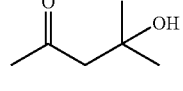 |
| 8 | 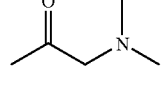 |
| 9 | 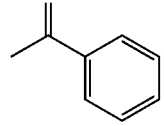 |
| 10 | 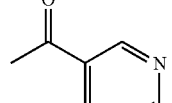 |
| 11 | 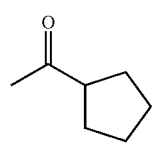 |
| 12 | 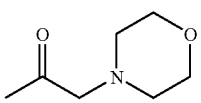 |
TABLE 22-continued
(Ie-2)
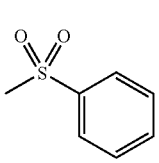
| No. | R⁵⁴ |
|---|---|
| 13 | 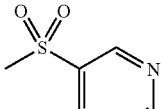 |
| 14 | 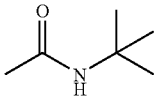 |
| 15 | 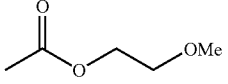 |
| 16 | 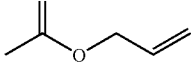 |
| 17 | 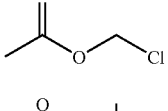 |
| 18 | 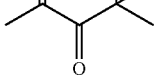 |
| 19 | 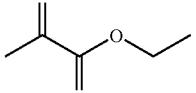 |
| 20 | 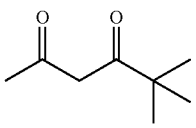 |
| 21 | |
| 22 | |

TABLE 22-continued (Ie-2)

| No. | R⁵⁴ |
|---|---|
| 23 | propanoic acid |
| 24 | 1-morpholinopropan-1-one |

TABLE 23

(Ie-3)

| No. | R⁵⁴ |
|---|---|
| 1 | isopentyl |
| 2 | 3-hydroxypropyl |
| 3 | 3-methoxypropyl |
| 4 | 2-methyl-2-hydroxybutyl |
| 5 | 2,3-dihydroxybutyl |
| 6 | 3,3-dimethyl-2-oxobutyl |
| 7 | 1-hydroxypropan-2-one |
| 8 | 4-hydroxy-4-methyl-2-oxopentyl |

TABLE 23-continued (Ie-3)

| No. | R⁵⁴ |
|---|---|
| 9 | 1-(dimethylamino)propan-2-one |
| 10 | 1-phenylethanone |
| 11 | 1-(pyridin-3-yl)ethanone |
| 12 | 1-cyclopentylethanone |
| 13 | 1-morpholinopropan-2-one |
| 14 | (methylsulfonyl)benzene |
| 15 | 3-(methylsulfonyl)pyridine |
| 16 | N-tert-butylacetamide |
| 17 | 2-methoxyethyl acetate |
| 18 | allyl acetate |

TABLE 23-continued (Ie-3)

| No. | R⁵⁴ |
|---|---|
| 19 | ClCH₂OC(O)CH₃ (chloromethyl acetate group) |
| 20 | C(O)C(O)C(CH₃)₃ (pivaloyl-type diketone) |
| 21 | C(O)C(O)OEt (ethyl pyruvate group) |
| 22 | C(O)CH₂C(O)C(CH₃)₃ |
| 23 | CH₂CH₂COOH |
| 24 | CH₂CH₂C(O)-morpholine |

TABLE 24

(Ie-4)

| No. | R⁵⁴ |
|---|---|
| 1 | isopentyl (CH₂CH(CH₃)CH₂CH₃) |
| 2 | CH₂CH₂CH₂OH |
| 3 | CH₂CH₂CH₂OMe |
| 4 | CH₂CH₂C(CH₃)₂OH |
| 5 | CH₂CH(OH)CH₂OH |
| 6 | C(O)CH₂C(CH₃)₃ |
| 7 | C(O)CH₂OH |
| 8 | C(O)CH₂C(CH₃)₂OH |
| 9 | C(O)CH₂N(CH₃)₂ |
| 10 | C(O)-phenyl |
| 11 | C(O)-(3-pyridyl) |
| 12 | C(O)-cyclopentyl |
| 13 | C(O)CH₂-morpholine |

TABLE 24-continued
(Ie-4)
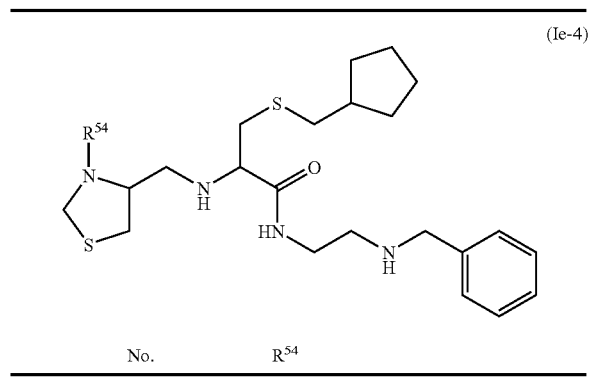
| No. | R⁵⁴ |
|---|---|
| 14 | 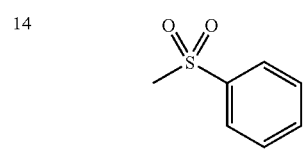 |
| 15 | 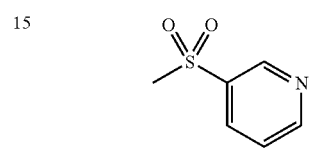 |
| 16 | 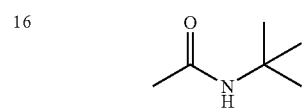 |
| 17 | 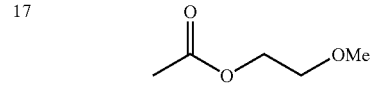 |
| 18 | 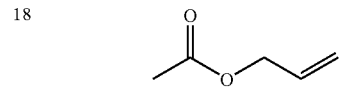 |
| 19 | 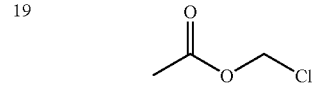 |
| 20 | 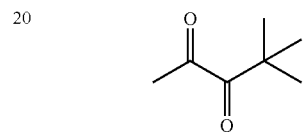 |
| 21 | 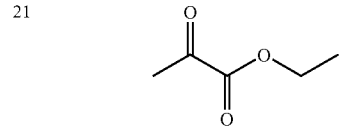 |
| 22 | 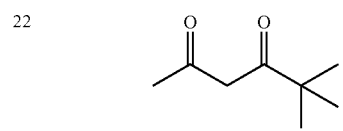 |
| 23 | 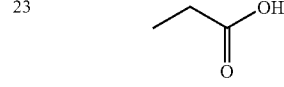 |
TABLE 24-continued
(Ie-4)
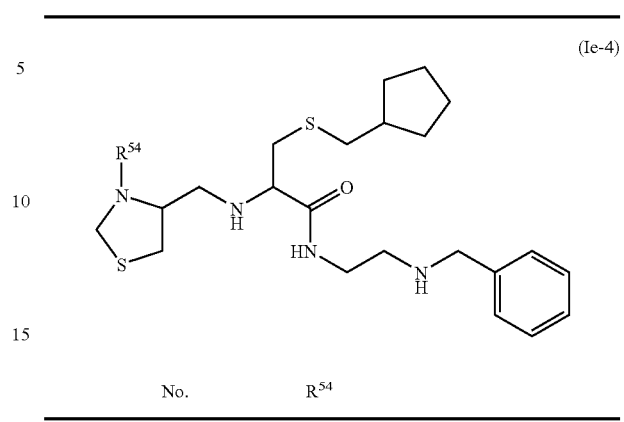
| No. | R⁵⁴ |
|---|---|
| 24 | 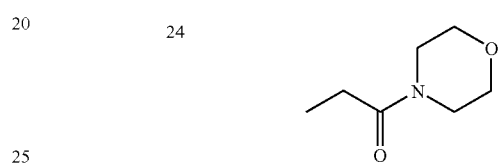 |
TABLE 25
(Ie-5)
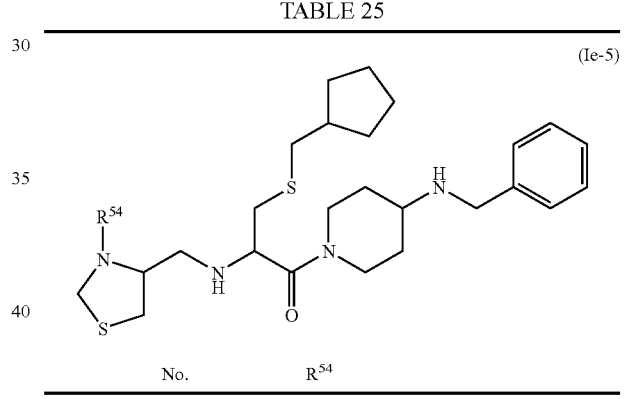
| No. | R⁵⁴ |
|---|---|
| 1 |  |
| 2 |  |
| 3 |  |
| 4 |  |
| 5 |  |
| 6 |  |
| 7 |  |

TABLE 25-continued (Ie-5)

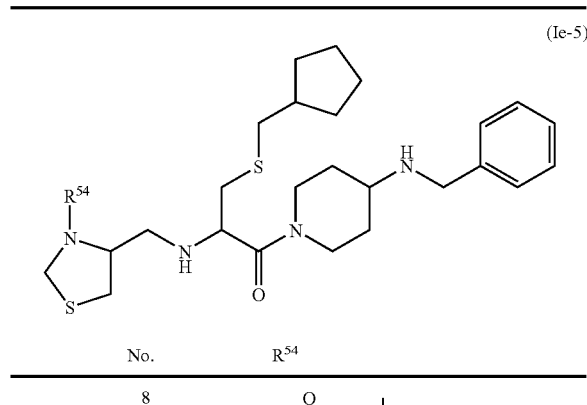

| No. | R⁵⁴ |
|---|---|
| 8 | 4-hydroxy-4-methyl-2-oxopentyl |
| 9 | (dimethylamino)acetyl |
| 10 | benzoyl |
| 11 | pyridine-3-carbonyl |
| 12 | cyclopentanecarbonyl |
| 13 | morpholin-4-ylacetyl |
| 14 | (methylsulfonyl)phenyl |
| 15 | (methylsulfonyl)pyridin-3-yl |
| 16 | tert-butylcarbamoyl |
| 17 | 2-methoxyethoxycarbonyl |
| 18 | allyloxycarbonyl |
| 19 | chloromethoxycarbonyl |
| 20 | 3,3-dimethyl-2-oxobutanoyl |
| 21 | ethyl 2-oxopropanoate |
| 22 | 5,5-dimethyl-2,4-dioxohexyl |
| 23 | propanoic acid |

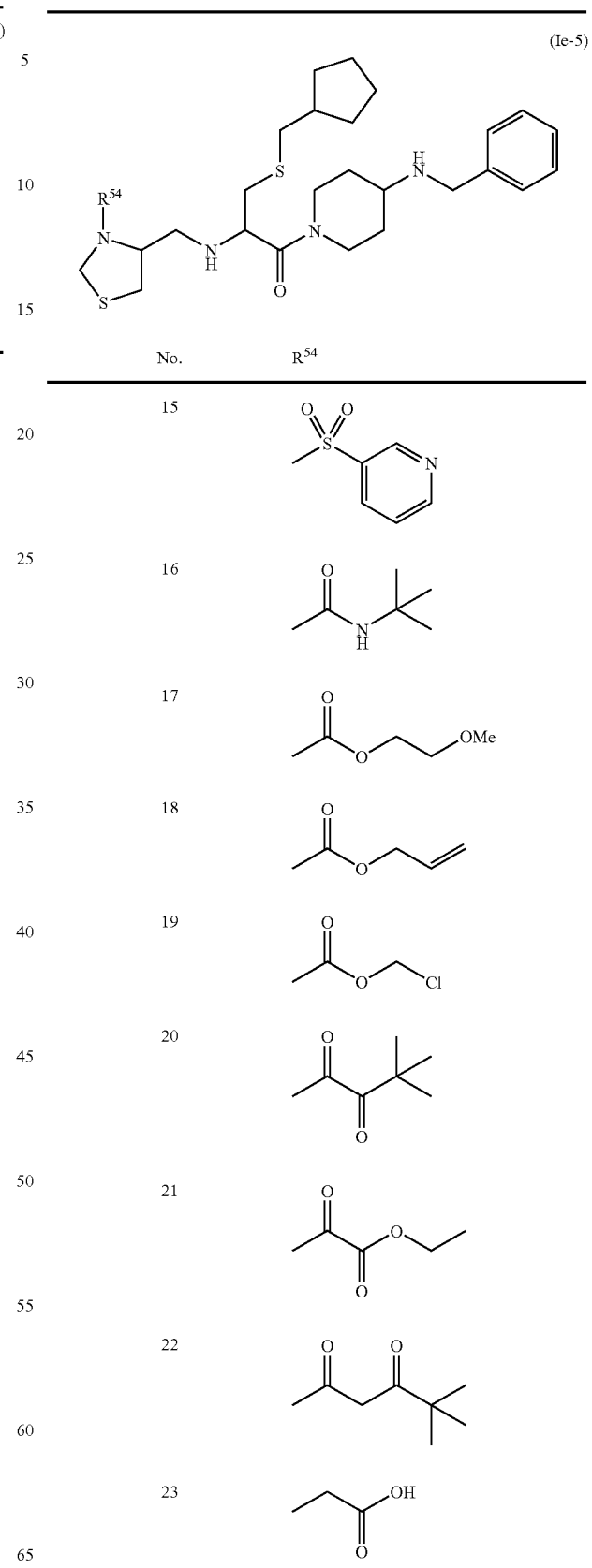

TABLE 25-continued
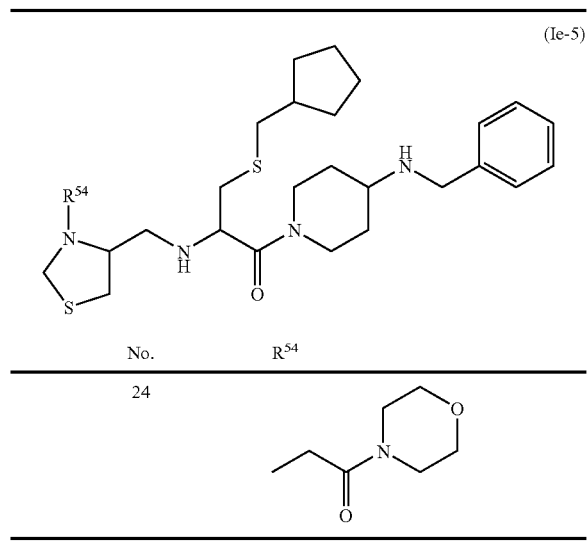
(Ie-5)
| No. | R⁵⁴ |
|---|---|
| 24 | 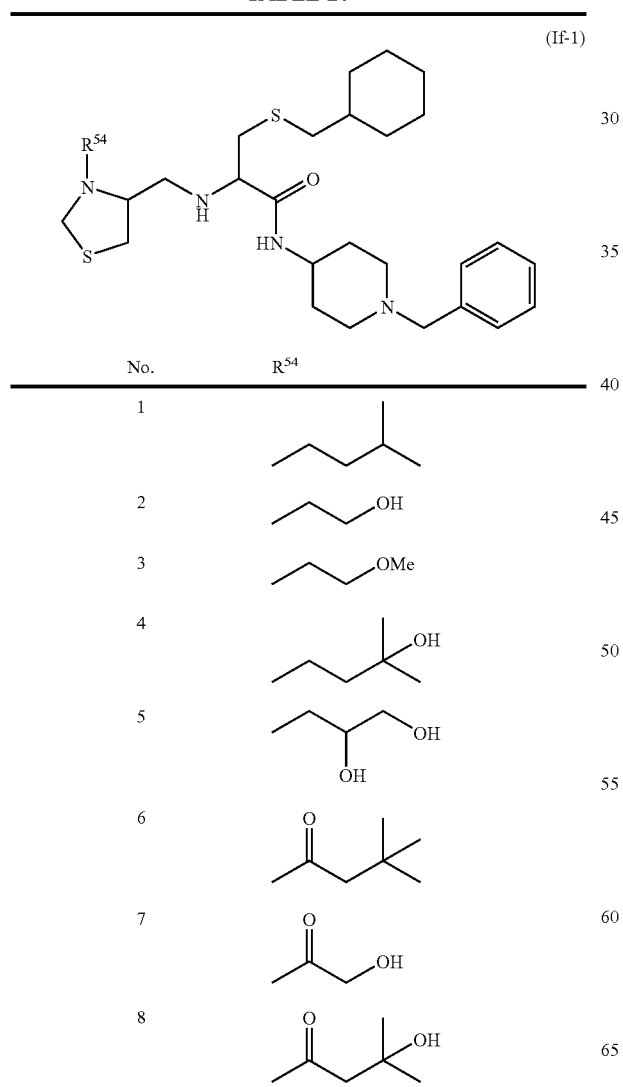 |
TABLE 26
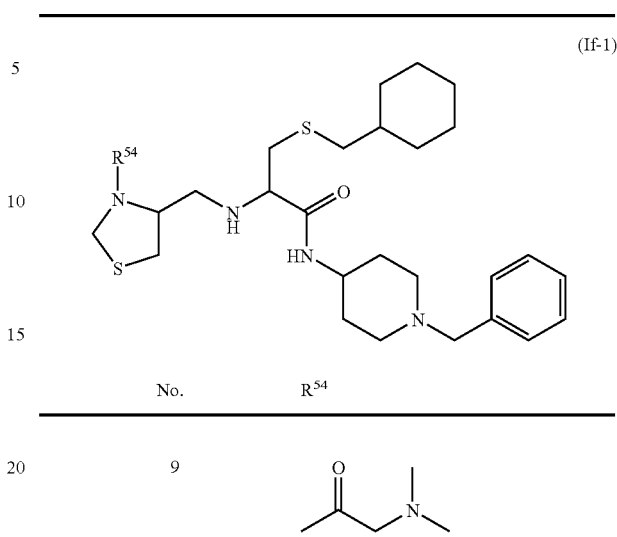
(If-1)
TABLE 26-continued
(If-1)
| No. | R⁵⁴ |
|---|---|
| 9 | |
| 10 | |
| 11 | |
| 12 | |
| 13 | |
| 14 | |
| 15 | |
| 16 | 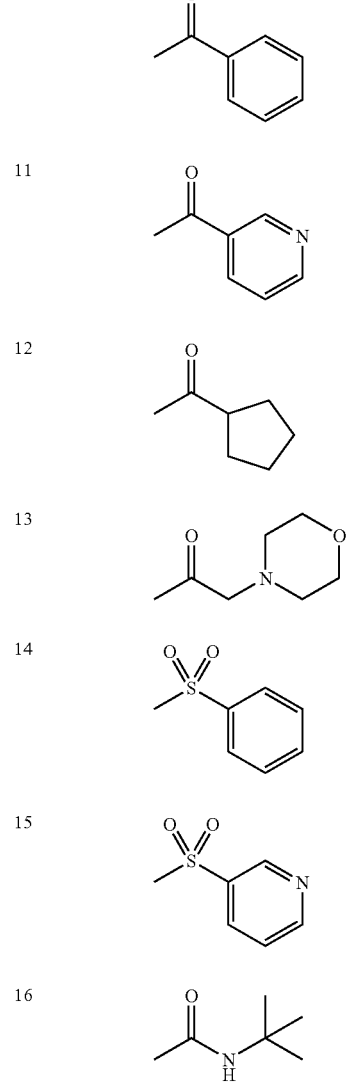 |

TABLE 26-continued
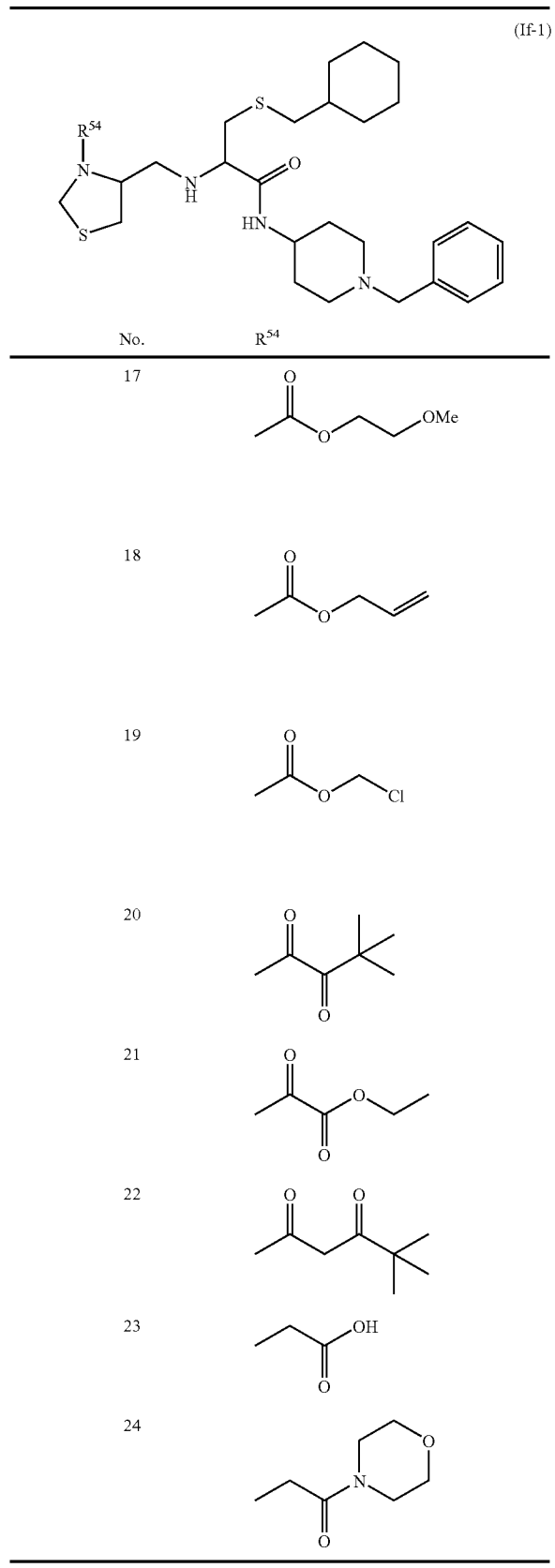
TABLE 27
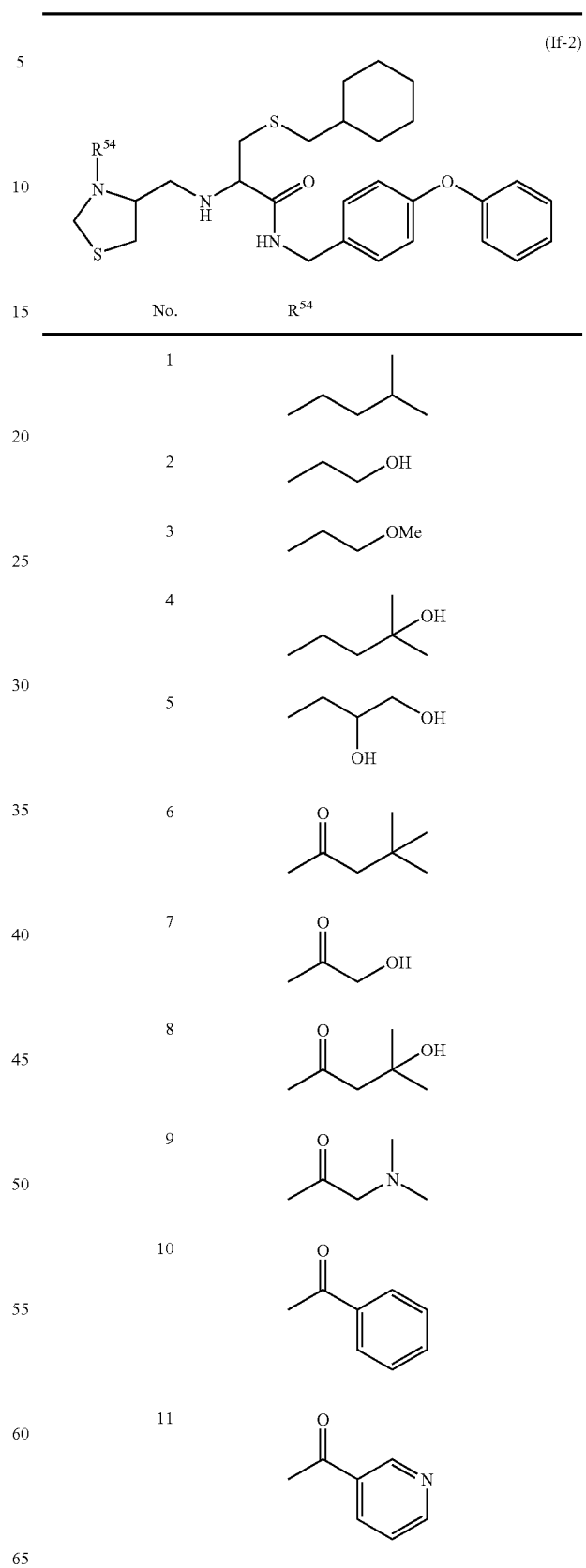

TABLE 27-continued (If-2)

| No. | R⁵⁴ |
|---|---|
| 12 | acetylcyclopentane |
| 13 | 1-morpholinopropan-2-one |
| 14 | methylsulfonylbenzene |
| 15 | 3-(methylsulfonyl)pyridine |
| 16 | N-tert-butylacetamide |
| 17 | 2-methoxyethyl acetate |
| 18 | allyl acetate |
| 19 | chloromethyl acetate |
| 20 | 1-(tert-butyl)propane-1,2-dione (2,2-dimethyl-3-oxobutanoyl) |
| 21 | ethyl 2-oxopropanoate |

TABLE 27-continued (If-2)

| No. | R⁵⁴ |
|---|---|
| 22 | 2,2-dimethylhexane-3,5-dione |
| 23 | propanoic acid |
| 24 | 1-morpholinopropan-1-one |

TABLE 28

(If-3)

| No. | R⁵⁴ |
|---|---|
| 1 | 2-methylpentyl |
| 2 | 3-hydroxypropyl |
| 3 | 3-methoxypropyl |
| 4 | 2-methyl-2-hydroxybutyl |
| 5 | 2,3-dihydroxybutyl |
| 6 | 4,4-dimethyl-2-oxopentyl |

TABLE 28-continued
(If-3)
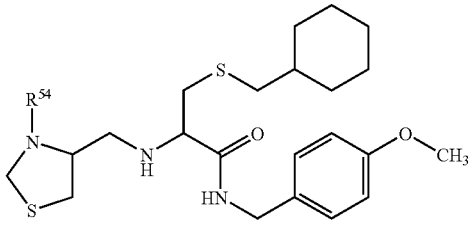
| No. | R⁵⁴ |
|---|---|
| 7 | 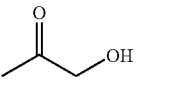 |
| 8 | 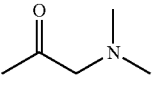 |
| 9 | 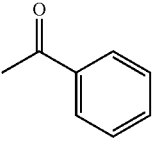 |
| 10 | 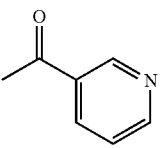 |
| 11 | 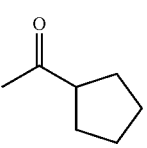 |
| 12 | 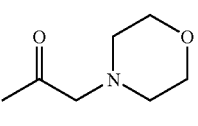 |
| 13 | 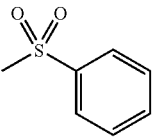 |
| 14 | 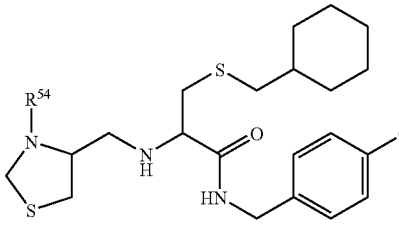 |
TABLE 28-continued
(If-3)
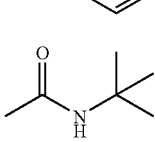
| No. | R⁵⁴ |
|---|---|
| 15 | 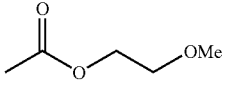 |
| 16 | 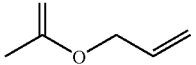 |
| 17 | 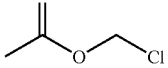 |
| 18 | 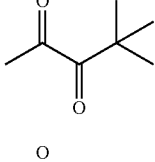 |
| 19 | 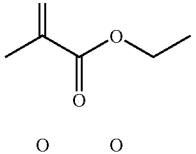 |
| 20 | 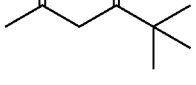 |
| 21 | 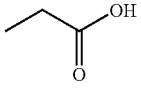 |
| 22 | 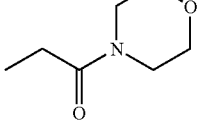 |
| 23 |  |
| 24 |  |

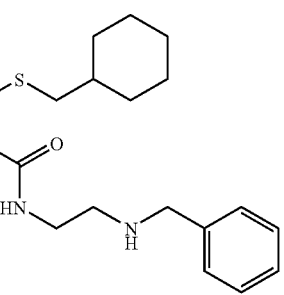

TABLE 29-continued (If-4)

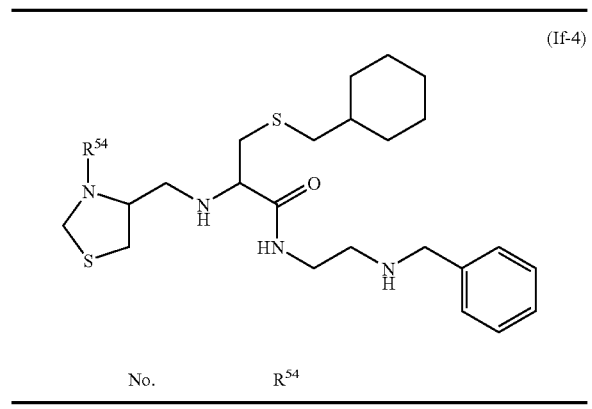

| No. | R⁵⁴ |
|---|---|
| 23 | 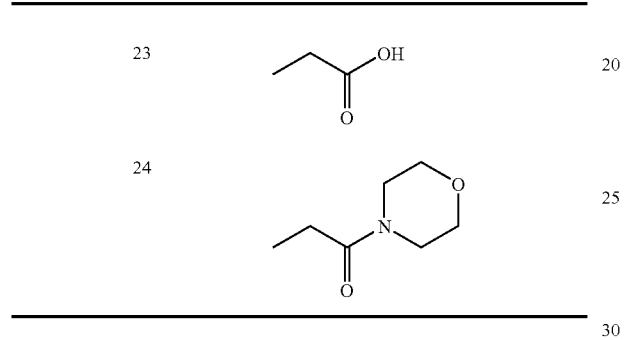 (propanoic acid) |
| 24 | (propanoyl morpholine) |

TABLE 30

(If-5)

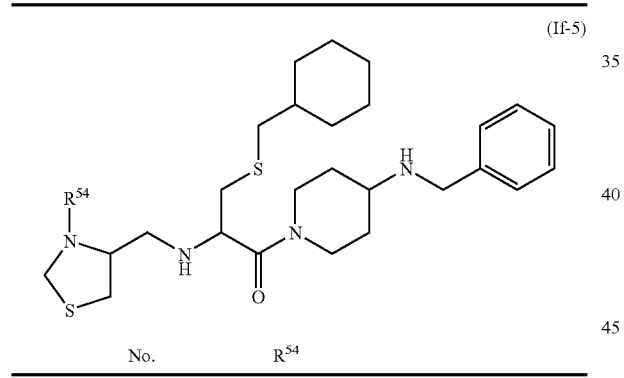

| No. | R⁵⁴ |
|---|---|
| 1 | (isopentyl) |
| 2 | (propanol) |
| 3 | (propyl OMe) |
| 4 | (2-methyl-2-butanol) |
| 5 | (propane-1,2-diol) |
| 6 | (4,4-dimethyl-2-pentanone) |

TABLE 30-continued (If-5)

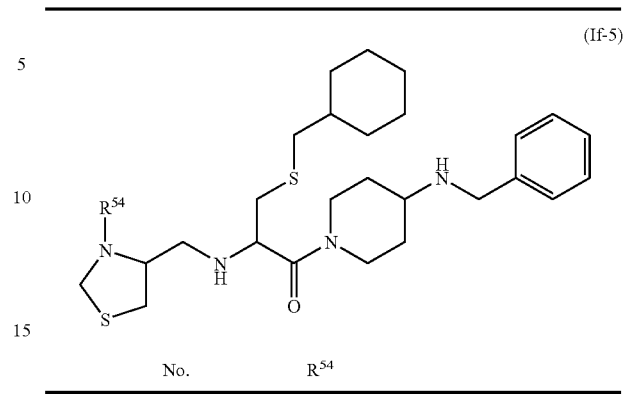

| No. | R⁵⁴ |
|---|---|
| 7 | (hydroxyacetone) |
| 8 | (4-hydroxy-4-methyl-2-pentanone) |
| 9 | (dimethylaminoacetone) |
| 10 | (acetophenone) |
| 11 | (3-acetylpyridine) |
| 12 | (cyclopentyl methyl ketone) |
| 13 | (morpholinoacetone) |
| 14 | (methylsulfonylbenzene) |
| 15 | (3-methylsulfonylpyridine) |

TABLE 30-continued
(If-5)
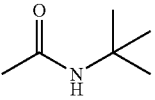
| No. | R⁵⁴ |
|---|---|
| 16 | 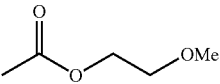 |
| 17 | 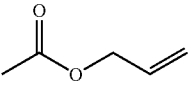 |
| 18 | 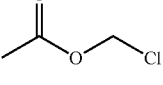 |
| 19 | 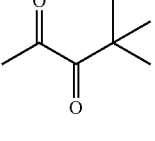 |
| 20 | 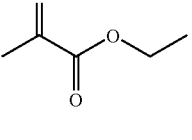 |
| 21 | 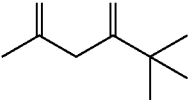 |
| 22 | 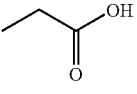 |
| 23 | 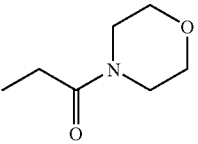 |
| 24 | 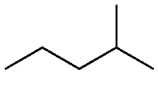 |
TABLE 31
(Ig-1)
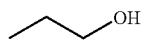
| No. | R⁵⁴ |
|---|---|
| 1 | 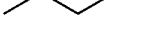 |
| 2 | 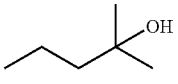 |
| 3 |  |
| 4 | 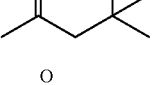 |
| 5 | 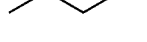 |
| 6 | 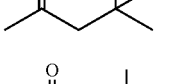 |
| 7 | 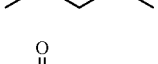 |
| 8 | 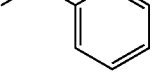 |
| 9 | 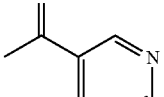 |
| 10 | 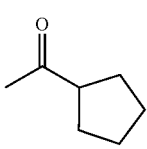 |
| 11 |  |
| 12 |  |

TABLE 31-continued (Ig-1)

| No. | R⁵⁴ |
|---|---|
| 13 | (2-morpholinyl-acetyl) |
| 14 | (phenylsulfonyl, methyl) |
| 15 | (pyridin-3-ylsulfonyl, methyl) |
| 16 | (N-tert-butyl-acetamide) |
| 17 | (2-methoxyethyl acetate) |
| 18 | (allyl acetate) |
| 19 | (chloromethyl acetate) |
| 20 | (1-tert-butyl-propane-1,2-dione) |
| 21 | (ethyl 2-oxopropanoate) |
| 22 | (5,5-dimethyl-hexane-2,4-dione) |
| 23 | (propanoic acid) |
| 24 | (1-morpholin-4-yl-propan-1-one) |

TABLE 32

(Ig-2)

| No. | R⁵⁴ |
|---|---|
| 1 | (isopentyl) |
| 2 | (3-hydroxypropyl) |
| 3 | (3-methoxypropyl) |
| 4 | (2-methylpentan-2-ol) |
| 5 | (butane-2,3-diol) |
| 6 | (4,4-dimethylpentan-2-one) |

TABLE 32-continued
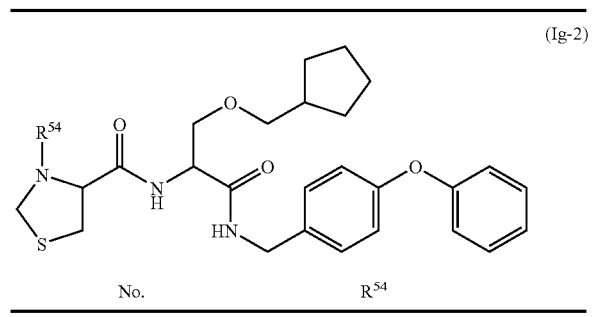
(Ig-2)
| No. | R⁵⁴ |
|---|---|
| 7 | 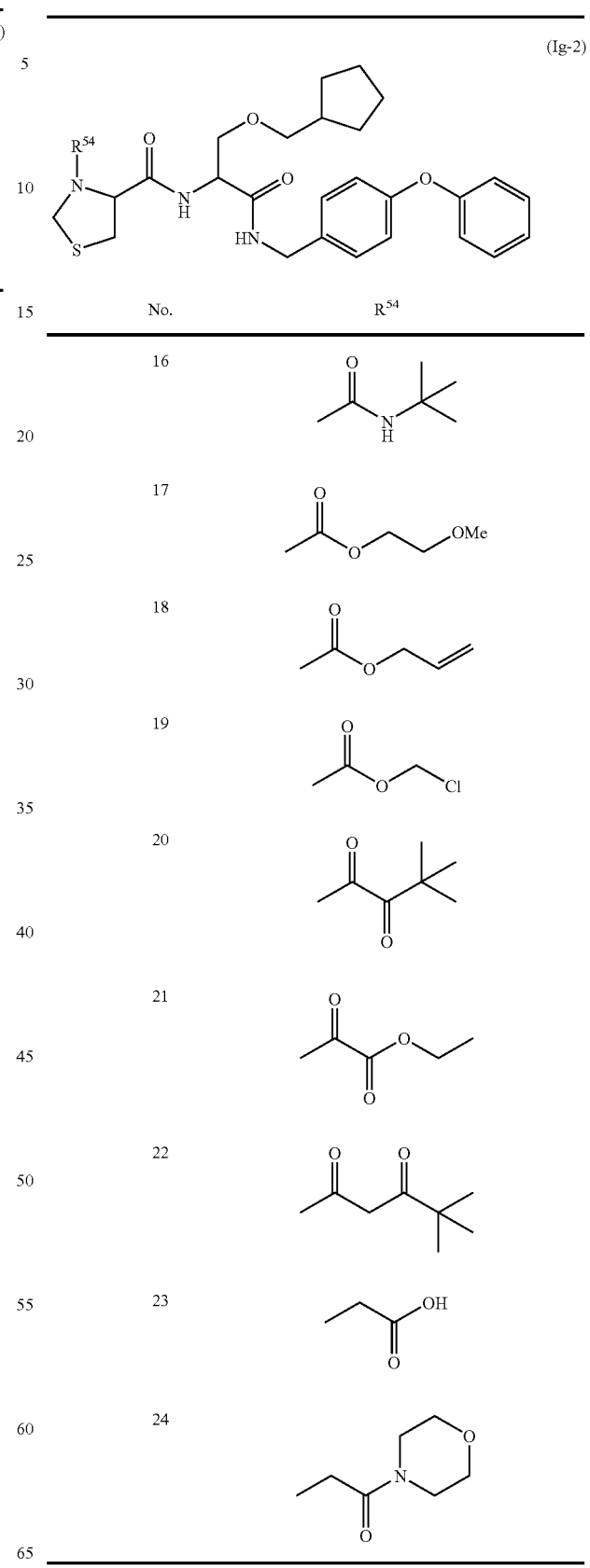 |
| 8 | |
| 9 | |
| 10 | |
| 11 | |
| 12 | |
| 13 | |
| 14 | |
| 15 | |
| 16 | |
| 17 | |
| 18 | |
| 19 | |
| 20 | |
| 21 | |
| 22 | |
| 23 | |
| 24 | |

TABLE 33
(Ig-3)
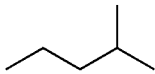
| No. | R[54] |
|---|---|
| 1 | 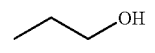 |
| 2 | 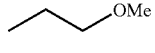 |
| 3 | 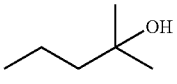 |
| 4 | 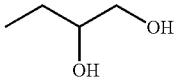 |
| 5 | 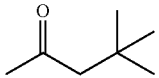 |
| 6 | 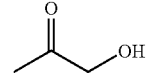 |
| 7 | 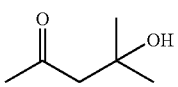 |
| 8 |  |
| 9 | 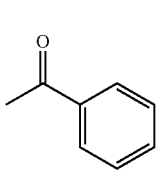 |
| 10 | 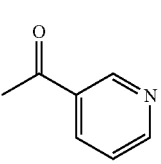 |
| 11 | 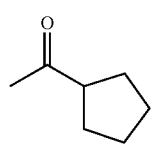 |
| 12 |  |
TABLE 33-continued
(Ig-3)
| No. | R[54] |
|---|---|
| 13 | 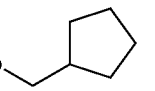 |
| 14 | 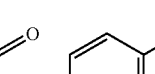 |
| 15 | 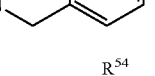 |
| 16 |  |
| 17 | 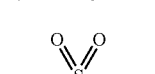 |
| 18 |  |
| 19 | 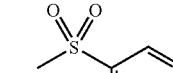 |
| 20 |  |
| 21 | 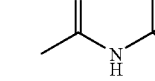 |
| 22 | 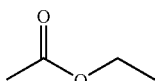 |

TABLE 33-continued
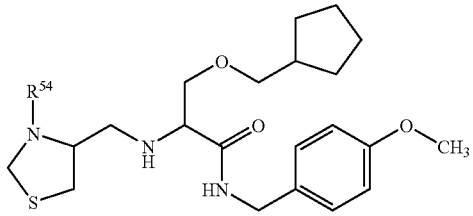
(Ig-3)
| No. | R^54 |
|---|---|
| 23 | 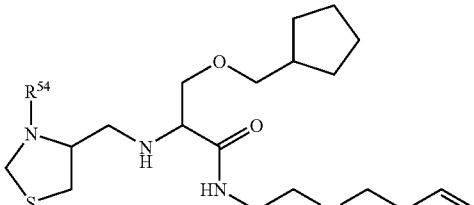 |
| 24 | 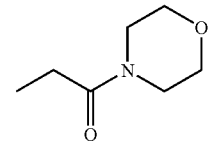 |
TABLE 34
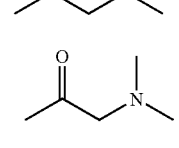
(Ig-4)
| No. | R^54 |
|---|---|
| 1 | 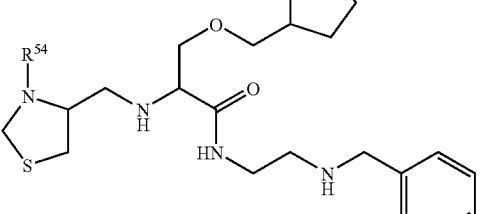 |
| 2 | 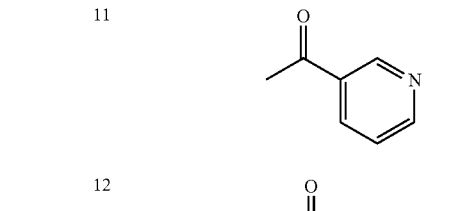 |
| 3 | 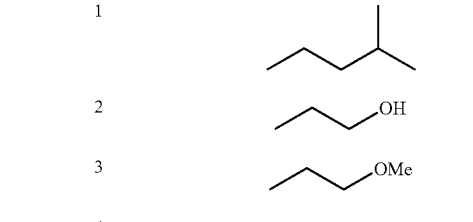 |
| 4 | 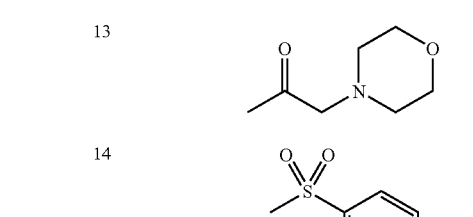 |
| 5 | 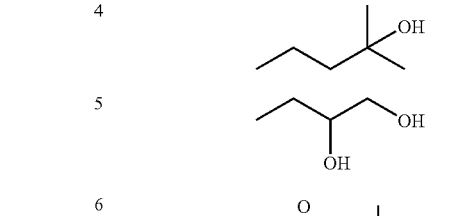 |
| 6 | 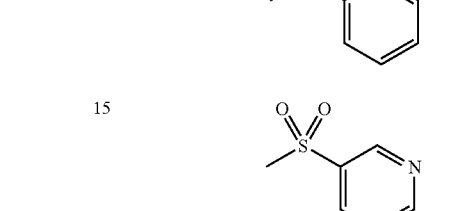 |
| 7 | 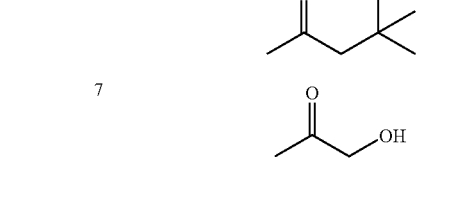 |
TABLE 34-continued
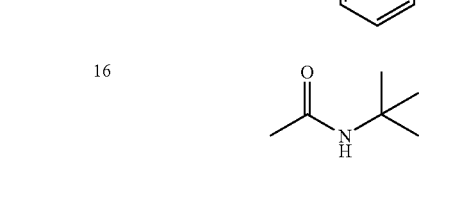
(Ig-4)
| No. | R^54 |
|---|---|
| 8 |  |
| 9 |  |
| 10 | 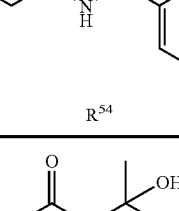 |
| 11 | 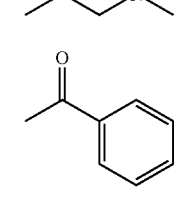 |
| 12 | 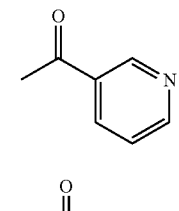 |
| 13 | 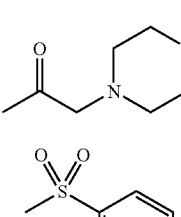 |
| 14 | 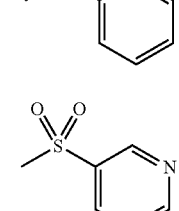 |
| 15 | 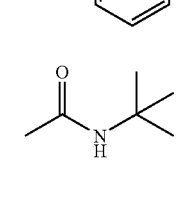 |
| 16 |  |

TABLE 34-continued (Ig-4)

[Structure: R54-N-thiazolidine-CH2-NH-CH(CH2-O-CH2-cyclopentyl)-C(=O)-NH-CH2CH2-NH-CH2-phenyl]

| No. | R54 |
|---|---|
| 17 | CH3-C(=O)-O-CH2CH2-OMe |
| 18 | CH3-C(=O)-O-CH2-CH=CH2 |
| 19 | CH3-C(=O)-O-CH2-Cl |
| 20 | CH3-C(=O)-C(=O)-C(CH3)3 |
| 21 | CH3-C(=O)-C(=O)-O-Et |
| 22 | CH3-C(=O)-CH2-C(=O)-C(CH3)3 |
| 23 | CH3CH2-C(=O)-OH |
| 24 | morpholine-C(=O)-CH2CH3 |

TABLE 35

(Ig-5)

[Structure: R54-N-thiazolidine-CH2-NH-CH(CH2-O-CH2-cyclopentyl)-C(=O)-N(piperidine-4-NH-CH2-phenyl)]

| No. | R54 |
|---|---|
| 1 | (CH3)2CH-CH2-CH2- (isopentyl) |
| 2 | HO-CH2CH2CH2- |
| 3 | MeO-CH2CH2CH2- |
| 4 | (CH3)2C(OH)-CH2-CH2- |
| 5 | CH3CH2-CH(OH)-CH2-OH |
| 6 | CH3-C(=O)-CH2-C(CH3)3 |
| 7 | CH3-C(=O)-CH2-OH |
| 8 | CH3-C(=O)-C(CH3)2-OH |
| 9 | CH3-C(=O)-CH2-N(CH3)2 |
| 10 | CH3-C(=O)-phenyl |
| 11 | CH3-C(=O)-(3-pyridyl) |
| 12 | CH3-C(=O)-cyclopentyl |

TABLE 35-continued
(Ig-5)
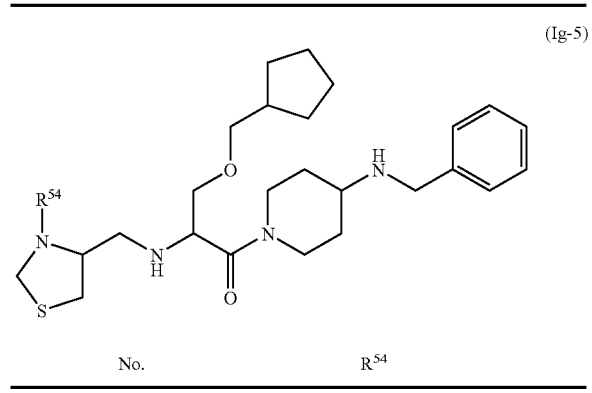
| No. | R⁵⁴ |
|---|---|
| 13 | 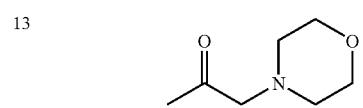 |
| 14 | 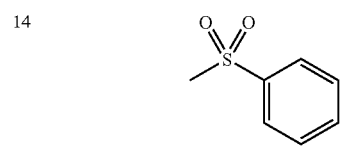 |
| 15 | 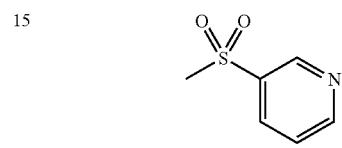 |
| 16 |  |
| 17 | 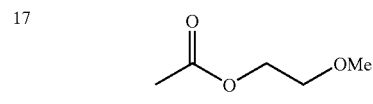 |
| 18 | 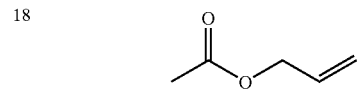 |
| 19 | 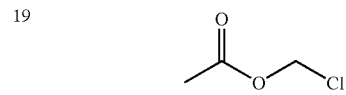 |
| 20 | 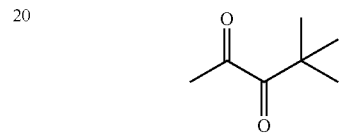 |
| 21 | 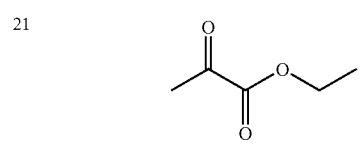 |
TABLE 35-continued
(Ig-5)
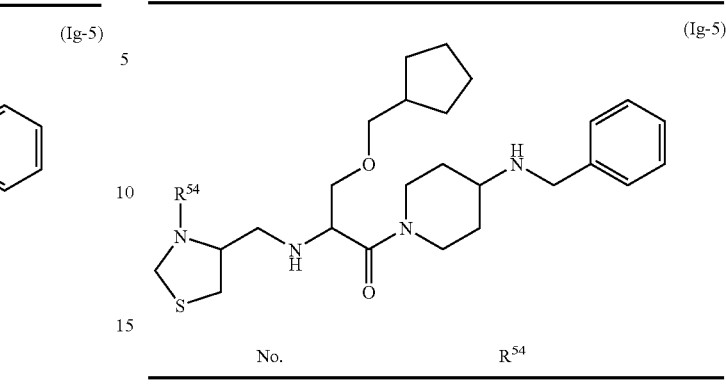
| No. | R⁵⁴ |
|---|---|
| 22 |  |
| 23 |  |
| 24 | 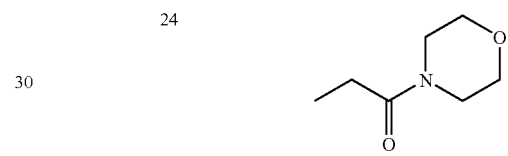 |
TABLE 36
(Ih-1)
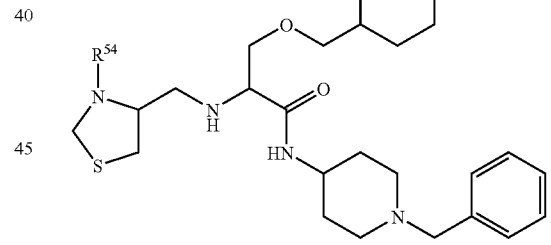
| No. | R⁵⁴ |
|---|---|
| 1 |  |
| 2 |  |
| 3 | 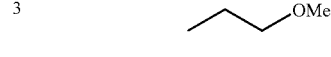 |
| 4 | 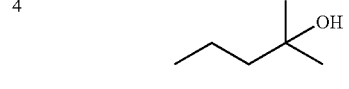 |
| 5 |  |

TABLE 36-continued (Ih-1)

| No. | R$^{54}$ |
|---|---|
| 6 | 3,3-dimethyl-2-oxobutanoyl (tert-butyl methyl ketone acyl) |
| 7 | hydroxyacetyl |
| 8 | 2-hydroxy-2-methylpropanoyl (extra methyl) |
| 9 | (dimethylamino)acetyl |
| 10 | benzoyl |
| 11 | pyridine-3-carbonyl |
| 12 | cyclopentanecarbonyl |
| 13 | 2-morpholinoacetyl |
| 14 | phenylmethanesulfonyl |
| 15 | (pyridin-3-yl)methanesulfonyl |

TABLE 36-continued (Ih-1)

| No. | R$^{54}$ |
|---|---|
| 16 | N-tert-butylcarbamoyl |
| 17 | 2-methoxyethoxycarbonyl |
| 18 | allyloxycarbonyl |
| 19 | chloromethoxycarbonyl |
| 20 | 3,3-dimethyl-2-oxobutanoyl |
| 21 | ethoxyoxalyl |
| 22 | 5,5-dimethyl-2,4-dioxohexanoyl |
| 23 | propanoic acid derivative |
| 24 | 1-morpholinopropan-1-one |

TABLE 37

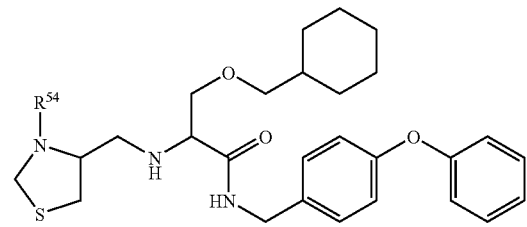

(Ih-2)

| No. | R⁵⁴ |
|---|---|
| 1 | 4-methylpentyl |
| 2 | propyl-OH |
| 3 | propyl-OMe |
| 4 | 2-methyl-2-hydroxybutyl |
| 5 | 2,3-dihydroxybutyl |
| 6 | 4,4-dimethyl-3-oxopentyl |
| 7 | hydroxyacetyl |
| 8 | 3-hydroxy-3-methyl-2-oxobutyl |
| 9 | dimethylaminoacetyl |
| 10 | benzoyl |
| 11 | 3-pyridinylcarbonyl |
| 12 | cyclopentylcarbonyl |

TABLE 37-continued

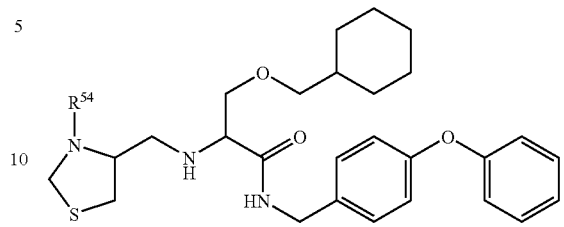

(Ih-2)

| No. | R⁵⁴ |
|---|---|
| 13 | morpholinoacetyl |
| 14 | phenylsulfonylmethyl |
| 15 | 3-pyridinylsulfonylmethyl |
| 16 | tert-butylaminocarbonylmethyl |
| 17 | 2-methoxyethoxycarbonylmethyl |
| 18 | allyloxycarbonylmethyl |
| 19 | chloromethoxycarbonylmethyl |
| 20 | 3,3-dimethyl-2-oxobutanoyl |
| 21 | ethoxyoxalyl |
| 22 | 4,4-dimethyl-2,3-dioxopentyl |

TABLE 37-continued (Ih-2)

| No. | R⁵⁴ |
|---|---|
| 23 | propanoic acid (CH₃CH₂COOH) |
| 24 | 1-(morpholin-4-yl)propan-1-one |

TABLE 38

(Ih-3)

| No. | R⁵⁴ |
|---|---|
| 1 | 3-methylbutyl |
| 2 | 3-hydroxypropyl |
| 3 | 3-methoxypropyl |
| 4 | 2-methyl-2-hydroxypentyl |
| 5 | 2,3-dihydroxybutyl |
| 6 | 4,4-dimethyl-3-oxopentyl (pivaloylmethyl) |
| 7 | 1-hydroxy-2-oxopropyl |
| 8 | 4-hydroxy-4-methyl-2-oxopentyl |

TABLE 38-continued (Ih-3)

| No. | R⁵⁴ |
|---|---|
| 9 | (dimethylamino)acetyl-methyl |
| 10 | benzoyl methyl |
| 11 | (pyridin-3-yl)carbonylmethyl |
| 12 | cyclopentylcarbonylmethyl |
| 13 | (morpholin-4-yl)acetyl-methyl |
| 14 | (phenylsulfonyl)methyl |
| 15 | (pyridin-3-ylsulfonyl)methyl |
| 16 | N-tert-butylacetamide |

TABLE 38-continued
(Ih-3)
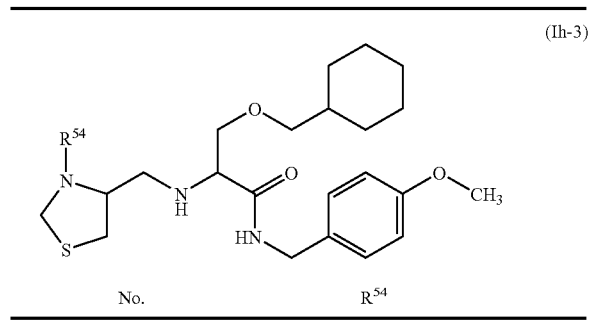
| No. | R^54 |
|---|---|
| 17 | 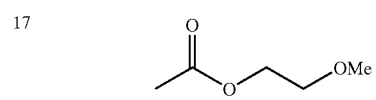 |
| 18 | 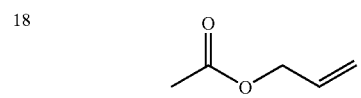 |
| 19 |  |
| 20 | 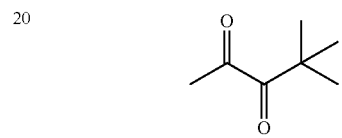 |
| 21 | 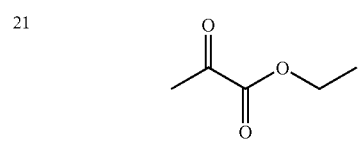 |
| 22 | 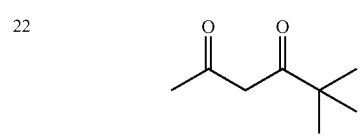 |
| 23 | 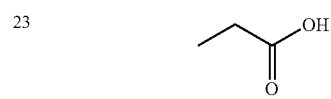 |
| 24 | 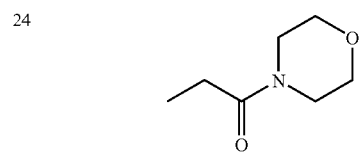 |
TABLE 39
(Ih-4)
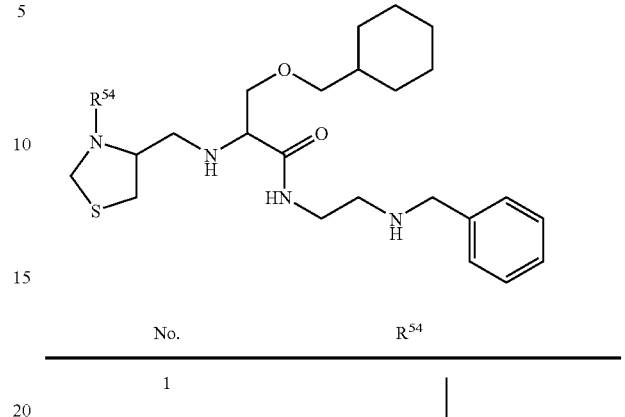
| No. | R^54 |
|---|---|
| 1 |  |
| 2 |  |
| 3 |  |
| 4 |  |
| 5 |  |
| 6 |  |
| 7 |  |
| 8 |  |
| 9 |  |
| 10 | 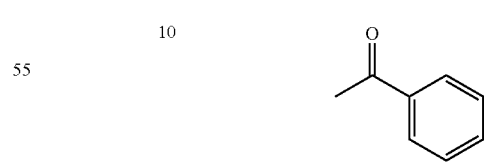 |
| 11 | 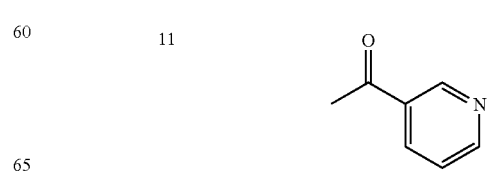 |

TABLE 39-continued (Ih-4)

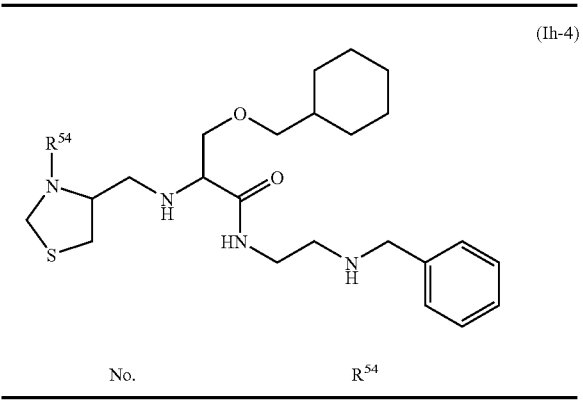

| No. | R⁵⁴ |
|---|---|
| 12 | cyclopentyl methyl ketone |
| 13 | morpholinyl acetone |
| 14 | methylsulfonyl benzene |
| 15 | methylsulfonyl pyridine |
| 16 | N-tert-butyl acetamide |
| 17 | 2-methoxyethyl acetate |
| 18 | allyl acetate |
| 19 | chloromethyl acetate |
| 20 | 1-(tert-butyl)-1,2-propanedione |

TABLE 39-continued (Ih-4)

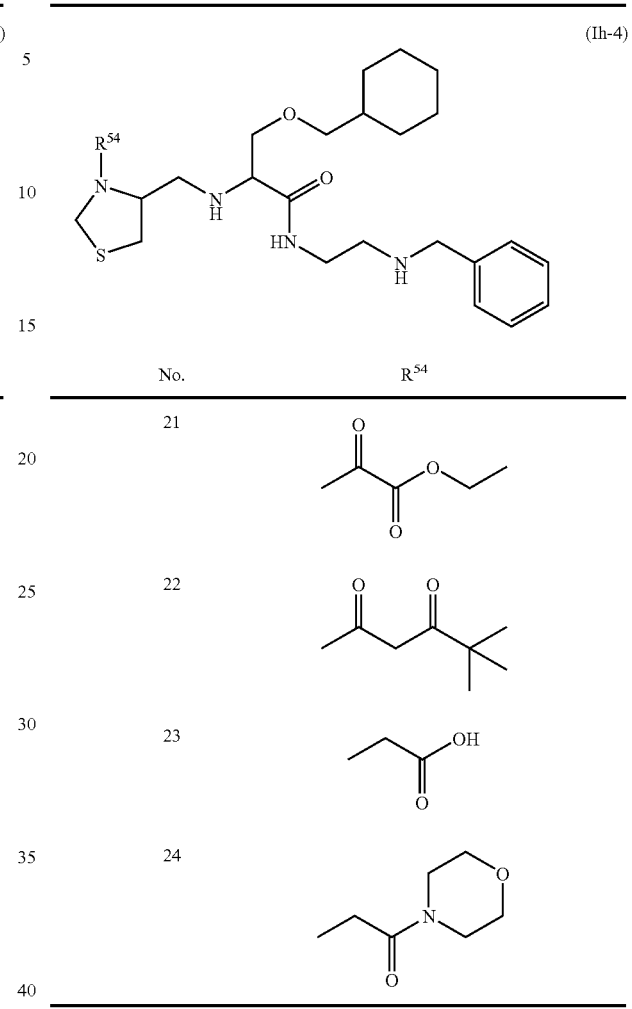

| No. | R⁵⁴ |
|---|---|
| 21 | ethyl pyruvate |
| 22 | 5,5-dimethyl-2,4-hexanedione |
| 23 | propionic acid |
| 24 | 1-morpholinopropan-1-one |

TABLE 40

(Ih-5)

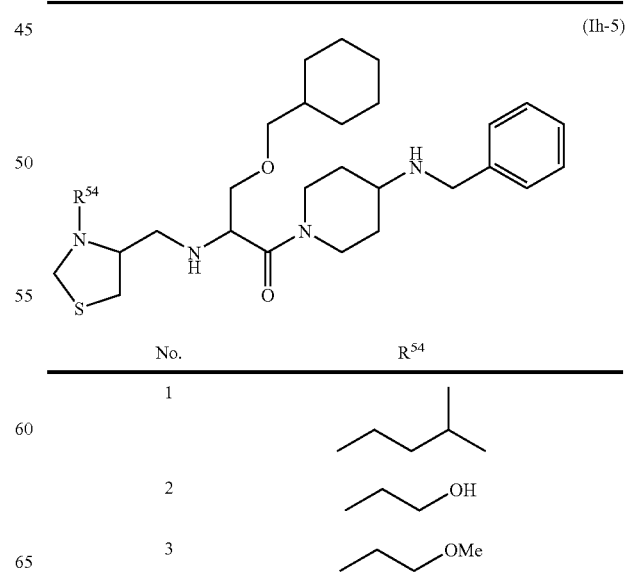

| No. | R⁵⁴ |
|---|---|
| 1 | isopentyl |
| 2 | propanol |
| 3 | methoxypropyl |

TABLE 40-continued (Ih-5)

| No. | R⁵⁴ |
|---|---|
| 4 | 2-methyl-2-hydroxypentyl (CH₃C(OH)(CH₃)CH₂CH₂CH₃) |
| 5 | 1,2-dihydroxybutyl |
| 6 | 3,3-dimethyl-2-oxobutyl |
| 7 | 1-hydroxy-2-oxopropyl |
| 8 | 3-hydroxy-3-methyl-2-oxobutyl |
| 9 | 1-(dimethylamino)-2-oxopropyl |
| 10 | phenacyl |
| 11 | (pyridin-3-yl)carbonylmethyl |
| 12 | cyclopentylcarbonylmethyl |
| 13 | (morpholin-4-yl)acetyl |

TABLE 40-continued (Ih-5)

| No. | R⁵⁴ |
|---|---|
| 14 | phenylsulfonyl-methyl |
| 15 | (pyridin-3-yl)sulfonylmethyl |
| 16 | N-tert-butylacetamide |
| 17 | 2-methoxyethyl acetate |
| 18 | allyl acetate |
| 19 | chloromethyl acetate |
| 20 | 3,3-dimethyl-2,3-dioxobutyl |
| 21 | ethyl 2-oxopropanoate |
| 22 | 4,4-dimethyl-2,3-dioxopentyl |
| 23 | propanoic acid |

TABLE 40-continued (Ih-5)

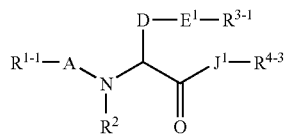

| No. | R⁵⁴ |
|---|---|
| 24 | 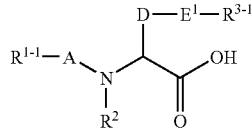 |

[Process for Preparation of the Compounds of the Present Invention]

(a) The compounds of the formula (I), wherein E is —COO—, —OCO—, —CONR²⁶—, —NR²⁷CO—, —O—, —S— or —CO—, i.e., the compounds of the present invention of the formula (I-A)

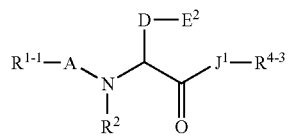

(I-A)

(wherein, $R^{1-1}$ is the same meaning as hereinbefore described for $R^1$, provided that hydroxy, —COOH or amino group in $R^{1-1}$ is protected with protecting group, if necessary, $R^{3-1}$ is the same meaning as hereinbefore described for $R^3$, provided that amino group in $R^{3-1}$ is protected with protecting group, if necessary, $R^{4-3}$ is the same meaning as hereinbefore described for $R^4$, provided that —COOH, hydroxy or amino group in $R^{4-3}$ is protected with protecting group, if necessary, $J^1$ is the same meaning as hereinbefore described for J, provided that amino or hydroxy group in $J^1$ is protected with protecting group, if necessary, $E^1$ is —COO—, —OCO—, —CONR²⁶—, —NR²⁷CO—, —O—, —S— or —CO— and the other symbols are the same meanings as defined hereinbefore) may be prepared by amidation or esterification of the compounds of the formula (II)

(II)

(wherein all the symbols are the same meanings as defined hereinbefore) with the compounds of the formula (III)

$J^2\text{-}R^{4-3}$ (III)

(wherein, $J^2$ is —OH, —NHR³⁴⁻¹ (in which, $R^{32-1}$ is the same meaning as hereinbefore described for $R^{32}$, provided that amino or hydroxy group in $R^{34-1}$ is protected with protecting group if necessary), —NR³⁸—NHR³⁷, —NR⁴⁰—(C1-4 alkylene)-NHR³⁹, —O— (C1-4 alkylene)-NHR⁴¹, —S— (C1-4 alkylene)-NHR⁴² or heterocyclic ring possessing NH (this heterocyclic ring is the same meaning as hereinbefore described for the heterocyclic ring represented by each $R^{4-1}$ and $R^{34}$, $R^{4-1}$ and $R^{36}$, $R^{4-1}$ and $R^{40}$, L and $R^{34}$, L and $R^{38}$, and L and $R^{40}$ taken together with nitrogen atom to which they are attached) (in which all the symbols are the same meanings as defined hereinbefore) and $R^{4-3}$ is the same meaning as hereinbefore described) or by amidation or esterification of the compounds of the formula (IV)

(IV)

(wherein, $E^2$ is —COOH, —NHR²⁷ (in which $R^{27}$ is the same meaning as defined hereinbefore) or —OH and the other symbols are the same meanings as defined hereinbefore) with the compounds of the formula (V)

$E^3\text{-}R^{3-1}$ (V)

(wherein, $E^3$ is —OH, —NHR²⁶ (in which $R^{26}$ is the same meaning as defined hereinbefore) or —COOH and the other symbols are the same meanings as defined hereinbefore).

The amidation is well known. For example, it may be carried out (1) by the method with using acid halide,
(2) by the method with using mixed acid anhydride,
(3) by the method with using conducing agent etc.

Concrete description of these methods are as follows:

(1) Method with using acid halide may be carried out, for example; carboxylic acid is reacted with an acid halide (oxalyl chloride, thionyl chloride or isobutyl chloroformate etc.) in an organic solvent (chloroform, methylene chloride, diethyl ether, tetrahydrofuran or ethyl acetate etc.) or without solvents at from −20° C. to a refluxing temperature to give an acid halide. The obtained acid halide and an amine are reacted in an organic solvent (chloroform, methylene chloride, diethyl ether, tetrahydrofuran etc.) in the presence of tertiary amine (pyridine, triethylamine, dimethylaniline, dimethylaminopyridine or N-methylmorpholine etc.) at 0~40° C.

(2) Method with using mixed acid anhydride may be carried out, for example; carboxylic acid is reacted with an acid halide (pivaloyl chloride, tosyl chloride, mesyl chloride, ethyl chloroformate, isobutyl chloroformate etc.) in an organic solvent (chloroform, methylene chloride, diethyl ether, tetrahydrofuran etc.) or without solvents, in the presence of tertiary amine (pyridine, triethylamine dimethylaniline, dimethylaminopyridine or N-methylmorpholine etc.) at −20~40° C. to give mixed acid anhydride. The obtained mixed acid anhydride and corresponding amine are reacted in an organic solvent (chloroform, methylene chloride, diethyl ether, tetrahydrofuran etc.) at 0~40° C.

(3) Method with using condensing agent (1,3-dicyclohexylcarbodiimido (DCC), 1-ethyl-3-[3-(dimethylamino)propyl]carbodiimido(EDC), 2-chloro-1-methylpyridiniumiodide, 1,1'-carbonydiimidazole (CDI) etc.) may be carried out, for example; a carboxylic acid and an amine are reacted in an organic solvent (chloroform, methylene chloride, dimethylformamide, diethyl ether or tetrahydrofuran etc.) or without solvents in the presence or absence of tertiary amine (pyridine, triethylamine, dimethylaniline or dimethylaminopyridine etc.) using with condensing agent and using or without 1-hydroxybenzotriazole (HoBt) at 0~40° C.

Preferably, the above reactions (1), (2) and (3) described above are carried out under an atmosphere of an inert gas (argon, nitrogen etc.) on anhydrous condition.

The esterification is well known. For example, it may be carried out (1) by the method with using acid halide, (2) by the method with using mixed acid anhydride, (3) by the method with using conducing agent etc.

Concrete description of these methods are as follows:

(1) Method with using acid halide may be carried out, for example; carboxylic acid is reacted with an acid halide (oxalyl chloride, thionyl chloride or isobutyl chloroformate etc.) in an organic solvent (chloroform, methylene chloride, diethyl ether, tetrahydrofuran or ethyl acetate etc.) or without solvents at from −20° C. to a refluxing temperature to give an acid halide. The obtained acid halide and an alcohol are reacted in an organic solvent (chloroform, methylene chloride, diethyl ether, tetrahydrofuran etc.) in the presence of tertiary amine (pyridine, triethylamine, dimethylaniline, dimethylaminopyridine or N-methylmorpholine etc.) at 0~40° C.

(2) Method with using mixed acid anhydride may be carried out, for example; carboxylic acid is reacted with an acid halide (pivaloyl chloride, tosyl chloride, mesyl chloride, ethyl chloroformate, isobutyl chloroformate etc.) in an organic solvent (chloroform, methylene chloride, diethyl ether, tetrahydrofuran etc.) or without solvents, in the presence of tertiary amine (pyridine, triethylamine, dimethylaniline, dimethylaminopyridine or N-methylmorpholine etc.) at −20~40° C. to give mixed acid anhydride. The obtained mixed acid anhydride and corresponding alcohol are reacted in an organic solvent (chloroform, methylene chloride, diethyl ether, tetrahydrofuran etc.) at 0~40° C.

(3) Method with using condensing agent (1,3-dicyclohexylcarbodiimido (DCC), 1-ethyl-3-[3-(dimethylamino)propyl]carbodiimido (EDC), 2-chloro-1-methylpyridiniumiodide, 1,1'-carbonyldiimidazole (CDI) etc.) may be carried out, for example; a carboxylic acid and an alcohol are reacted in an organic solvent (chloroform, methylene chloride, dimethylformamide, diethyl ether or tetrahydrofuran etc.) or without solvents in the presence or absence of tertiary amine (pyridine, triethylamine, dimethylaniline or dimethylaminopyridine etc.) using with condensing agent and using or without 1-hydroxybenzotriazole (HoBt) at 0~40° C.

Preferably, the above reactions (1), (2) and (3) described above are carried out under an atmosphere of an inert gas (argon, nitrogen etc.) on anhydrous condition.

The compounds of the formula (I-A), wherein $E^1$ is —S— i.e., the compounds of the formula (I-A-1)

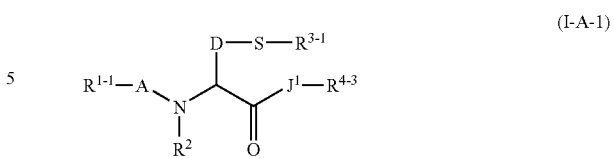

(I-A-1)

(wherein all the symbols are the same meanings as defined hereinbefore) may be prepared by reacting the compounds of the formula (VI)

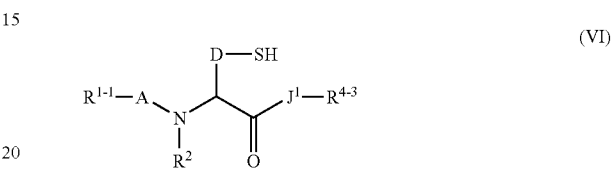

(VI)

(wherein all the symbols are the same meanings as defined hereinbefore) with the compounds of the formula (VII)

(VII)

(wherein, X is halogen and the other symbols are the same meanings as defined hereinbefore).

The reaction of the compounds of the formula (VI) and the compounds of the formula (VII) may be carried out by known methods. For example, it may be carried out in an organic solvent (dimethylformamide, acetone etc.) in the presence of base (potassium carbonate etc.) at 0~40° C.

(b) The compounds of the formula (I), wherein E is —SO—, —SO$_2$—, i.e., the compounds of the formula (I-B)

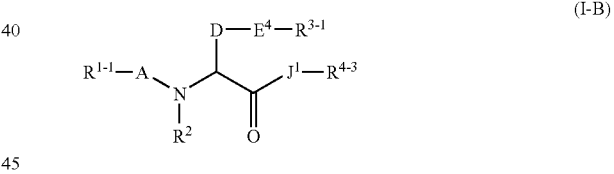

(I-B)

(wherein, $E^4$ is —SO— or —SO$_2$— and the other symbols are the same meanings as defined hereinbefore)

may be prepared by oxidation of the said compounds of the formula (I-A) wherein $E^1$ is —S—.

The oxidation is known per se. In case of oxidation of sulfide into sulfoxide, it may be carried out, for example, in an organic solvent (methylene chloride, chloroform, benzene, hexane, t-butyl alcohol etc.) in the presence of one equivalent of oxidizing agent (hydrogen peroxide, sodium periodate, acyl nitrite, sodium perborate, peracid (e.g., m-chloroperbenzoic acid, peracetic acid etc.) etc.) for a few minutes at −78~40° C.

In case of oxidation of sulfide into sulfon, it may be carried out, for example, in an organic solvent (methylene chloride, chloroform, benzene, hexane, t-butyl alcohol etc.) in the presence of an excessive amount of oxidizing agent (hydrogen peroxide, sodium periodate, potassium permanganate, sodium perbromate, potassium peroxymonosulfate, peracid (e.g., m-chloroperbenzoic acid, peracetic acid etc.) etc.) for a few hours at −78~40° C.

(c) The compounds of the formula (I), wherein E is —NR$^{28}$—, i.e., the compounds of the formula (I-C)

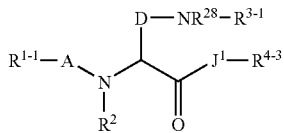 (I-C)

(wherein all the symbols are the same meanings as defined hereinbefore) may be prepared by reacting the compounds of the formula (VIII)

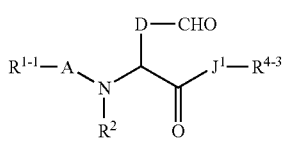 (VIII)

(wherein all the symbols are the same meanings as defined hereinbefore) with the compounds of the formula (IX)

NHR$^{28}$—R$^{3-1}$ (IX)

((wherein all the symbols are the same meanings as defined hereinbefore).

The reaction of the compounds of the formula (VIII) and the compounds of the formula (IX) may be carried out by known methods, for example, by reacting the compounds of the formula (VIII) and the compounds of the formula (IX) in an organic solvent (methanol, ethanol etc.) using reductant (sodium cyanoborohydride, sodium borohydride, etc.) or using pH adjustifying agent (acetic acid etc.) if necessary, at 0~40° C.

(d) The compounds of the formula (I), wherein E is —SO$_2$NR$^{29}$—, i.e., the compounds of the formula (I-D)

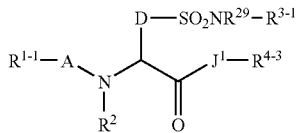 (I-D)

(wherein all the symbols are the same meanings as defined hereinbefore) may be prepared by reacting the compounds of the formula (X)

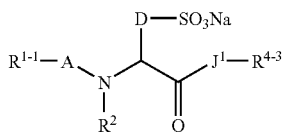 (X)

(wherein all the symbols are the same meanings as defined hereinbefore) with the compounds of the formula (XI)

NHR$^{29}$—R$^{3-1}$ (XI)

(wherein all the symbols are the same meanings as defined hereinbefore).

The reaction of the compounds of the formula (X) and the compounds of the formula (XI) may be carried out by known methods, for example, by reacting the compounds of the formula (X) with base (triphenylphosphine etc.) and acid halide (oxazolyl chloride, thionyl chloride etc.) in an organic solvent (chloroform, methylene chloride, diethyl ether, tetrahydrofran etc.), at from −20° C. to refluxing temperature, and then by reacting thus obtained compounds and the compounds of the formula (XI) in the presence of tertiary amine (pyridine, triethylamine, dimethylaniline, dimethylaminopyridine etc.) in an organic solvent (chloroform, methylene chloride, diethyl ether, tetrahydrofran etc.) at 0~40° C.

(e) The compounds of the formula (I), wherein E is —NR$^{30}$SO$_2$—, i.e., the compounds of the formula (I-E)

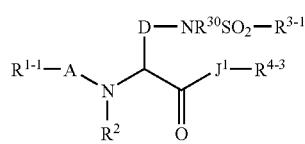 (I-E)

(wherein all the symbols are the same meanings as defined hereinbefore) may be prepared by reacting the compounds of the formula (XII)

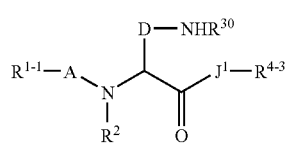 (XII)

(wherein all the symbols are the same meanings as defined hereinbefore) with the compounds of the formula (XIII)

X—SO$_2$—R$^{3-1}$ (XIII)

(wherein, X is halogen and the other symbols are the same meanings as defined hereinbefore).

The reaction of the compounds of the formula (XII) and the compounds of the formula (XIII) may be carried out, for example, by reacting the compounds of the formula (XII) and the compounds of the formula (XIII) in an organic solvent (chloroform, methylene chloride, diethyl ether, tetrahydrofran etc.) in the presence of tertiary amine (pyridine, triethylamine, dimethylaniline, dimethylaminopyridine etc.) at 0~40° C.

(f) The compounds of the formula (I), wherein A is —CO— or —SO$_2$—, i.e., the compounds of the formula (I-F)

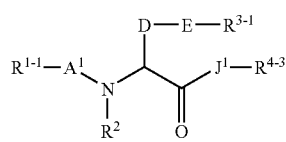 (I-F)

(wherein, A$^1$ is —CO— or —SO$_2$— and the other symbols are the same meanings as defined hereinbefore)

may be prepared by amidation or sulfonamidation of the compounds of the formula (XIV)

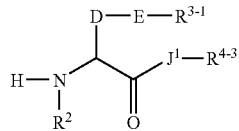
(XIV)

(wherein all the symbols are the same meanings as defined hereinbefore) with the compounds of the formula (XV)

$R^{1-1}-A^2$ (XV)

(wherein, $A^2$ is —COOH or —SO$_3$H and the other symbols are the same meanings as defined hereinbefore).

The sulfonamidation is well known. For example, it may be carried out by reacting sulfonic acid and an acid halide (oxalyl chloride, thionyl chloride, phosphorus pentachloride or phosphorus trichloride etc.) in an organic solvent (chloroform, methylene chloride, diethyl ether or tetrahydrofuran etc.) or without solvents at from −20° C. to a refluxing temperature to give a sulfonyl halide, and then by reacting the obtained sulfonyl halide and an amine in an organic solvent (chloroform, methylene chloride, diethyl ether, tetrahydrofuran etc.) in the presence of tertiary amine (pyridine, triethylamine, dimethylaniline or dimethylaminopyridine etc.) at 0~40° C.

The amidation may be carried out by the same method described hereinbefore.

(g) The compounds of the formula (I), wherein A is single bond and $R^1$ is C1-4 alkyl substituted with phenyl, C3-8 cycloalkyl or heterocyclic ring, i.e., the compounds of the formula (I-G)

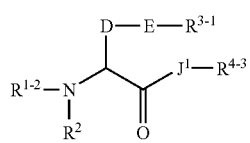
(I-G)

($R^{1-2}$ is C1-4 alkyl substituted with phenyl, C3-8 cycloalkyl or heterocyclic ring (with the proviso that when amino, hydroxy or —COOH group exists as a substituent of each ring, such amino, hydroxy or —COOH group is protected with protecting group, if necessary) and the other symbols are the same meanings as defined hereinbefore)

may be prepared by reacting the compounds of the formula (XIV)

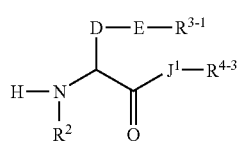
(XIV)

(wherein all the symbols are the same meanings as defined hereinbefore) with the compounds of the formula (XVI)

$R^{1-3}$—CHO (XVI)

(wherein, $R^{1-3}$ is phenyl, C3-8 cycloalkyl, heterocyclic ring or C1-3 alkyl substituted with phenyl, C3-8 cycloalkyl or heterocyclic ring (with the proviso that when amino, hydroxy or —COOH group exists as a substituent of each ring, such amino, hydroxy or —COOH group is protected with protecting group, if necessary)).

This reaction may be carried out by the same procedure as described in the reaction of the compounds of the formula (VIII) and the compounds of the formula (IX).

(h) The compounds of the formula (I) in which, $R^1$ is heterocyclic ring, C1-4 alkyl substituted with heterocyclic ring, and substituent of the said heterocyclic ring is (iii) —COOR$^5$, (v) —CO—R$^7$, (vii) —CO—CO—R$^{13}$, (viii) —CO—(C1-4 alkylene)-CO—R$^{14}$, (ix) —SO$_2$—R$^{15}$, (x) —CONR$^{18}$R$^{19}$, (xix) C2-5 acyl or (xxi) C1-4 alkoxycarbonyl, i.e., compounds of the formula (I-H)

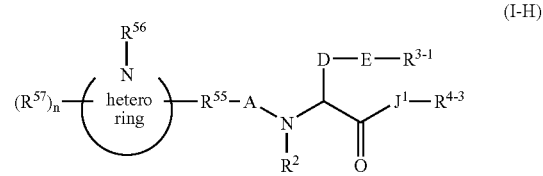
(I-H)

(wherein, $R^{55}$ is single bond or C1-4 alkylene, $R^{56}$ is the same meaning as the said substituent (iii), (v), (vii), (viii), (ix), (x), (xix) or (xxi) of heterocyclic ring, provided that amino, hydroxy or —COOH group exists in the said substituent, such a group is protected with protecting group if necessary, $R^{57}$ is the same meaning as the said substituent (i)-(xxiii) of heterocyclic ring, provided that amino, hydroxy or —COOH group exists in the said substituent, such a group is protected with protecting group if necessary, n is 0-3 and

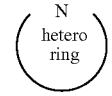

is the same meaning as the said heterocyclic ring in $R^1$, provided that such a ring contains at least one nitrogen atom)

may be prepared by amidation or sulfonamidation of compounds of the formula (XVVII)

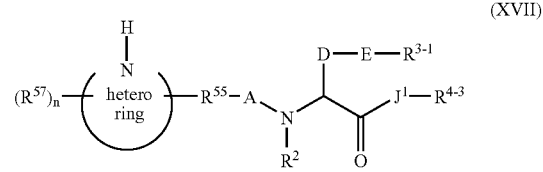
(XVII)

with compounds of the formula (XVIII)

$R^{56}$—OH (XVIII)

(wherein, $R^{56}$ is the same meaning as defined hereinbefore).

The amidation or sulfonamidation may be carried out by the same method described hereinbefore.

(i) The compounds of the formula (I) in which, $R^1$ is heterocyclic ring or C1-4 alkyl substituted with heterocyclic ring, and substituent of the said heterocyclic ring is (ii) C5-8 alkyl, (iv) —(C1-4 alkylene)-COOR$^6$, (vi) —(C1-4 alkylene)-CO—R$^{10}$, (xi) C1-8 alkyl substituted with 1~2 of substituent(s) selected from the group consisting of (1)-(7) or (xiii) C1-4 alkyl, i.e., compounds of the formula (I-I)

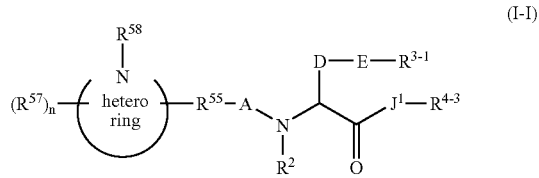

(I-I)

(wherein, R$^{58}$ is the same meaning as the said substituent (ii), (iv), (vi), (xi) or (xiii) of heterocyclic ring, provided that amino, hydroxy or —COOH group exists in the said substituent, such a group is protected with protecting group if necessary and all the symbols are the same meanings as defined hereinbefore)

may be prepared by reacting compounds of the formula (XVII) and compounds of the formula (XVIV)

R$^{59}$—CHO    (XVIV)

(wherein, R$^{59}$ is C4-7 alkyl, —COOR$^6$, —(C1-3 alkylene)-COOR$^6$, —CO—R$^{10}$, —(C1-3 alkylene)-CO—R$^{10}$, (xi) C1-7 alkyl substituted with 1~2 of substituent(s) selected from the group consisting of (1)-(7) or C1-3 alkyl (in which all the symbols are the same meanings as defined hereinbefore, provided that amino, hydroxy or —COOH group exists in the said substituent, such a group is protected with protecting group if necessary).

This reaction may be carried out by the same method as reaction of the said compounds of the formula (VIII) with compounds of the formula (IX).

(j) The compounds of the formula (I) in which, R$^1$ is heterocyclic ring or C1-4 alkyl substituted with heterocyclic ring, and substituent of the said heterocyclic ring is (x) —CONHR$^{19}$, i.e., compounds of the formula (I-J)

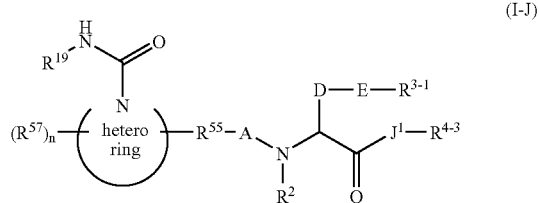

(I-J)

(wherein, all the symbols are the same meaning as defined hereinbefore) may be prepared by reacting the said compounds of the formula (XVII) and compounds of the formula (XVV)

R$^{19}$—N=C=O    (XVV)

(wherein, R$^{19}$ is the same meaning as defined hereinbefore).

This reaction may be carried out by known methods. For example, it may be carried out by reacting compounds of the formula (XVII) and compounds of the formula (XVV) in organic solvent (chloroform, methylene chloride, diethyl ether, tetrahydrofuran etc.), in the presence of base (triethylamine, pyridine, dimethylaniline, dimethylaminopyridine, N-methylmorpholine etc.), at from 0° C. to refluxing temperature.

(k) Among the compounds of the formula (I), the compounds of the formula (I-K)

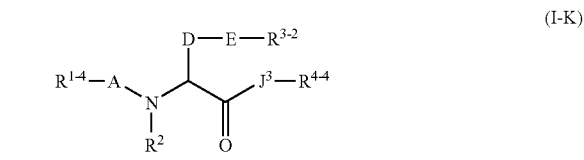

(I-K)

(wherein, R$^{1-4}$, R$^{3-2}$, R$^{4-4}$ and J$^3$ are the same meanings as hereinbefore described for R$^1$, R$^3$, R$^4$ and J respectively, provided that at least one of them is a group containing —COOH, hydroxy or amino and the other symbols are the same meanings as defined hereinbefore)

may be prepared by removal of protecting group according to alkaline hydrolysis, by removal of protecting group in an acidic condition and/or by hydrogenolysis of the compounds of the said formulae (I-A), (I-A-1), (I-B), (I-C), (I-D), (I-E), (I-F), (I-G), (I-H), (I-I) or (I-J).

The removal of a protecting group according to alkaline hydrolysis is well known. For example, it may be carried out in an organic solvent (methanol, tetrahydrofuran, dioxane etc.), using hydroxide of an alkaline metal (sodium hydroxide, potassium hydroxide, lithium hydroxide etc.), hydroxide of an alkaline earth metal (calcium hydroxide etc.) or carbonate (sodium carbonate, potassium carbonate etc.) or an aqueous solution thereof or a mixture thereof at 0~40° C.

The removal of a protecting group in an acidic condition is well known. For example, it may be carried out in an organic solvent (methylene chloride, chloroform, dioxane, ethyl acetate, anisole etc.) or without solvent, in the presence of organic acid (trifluoroacetic acid, methanesulfonic acid, trimethylsilyliodide etc.) or inorganic acid (hydrochloric acid etc.) or a mixture thereof (bromohydroacetic acid etc.) at 0~90° C.

The hydrogenolysis is well known. For example, it may be carried out in an organic solvent (tetrahydrofran, dioxane, diethyl ether, ethyl acetate, methanol, ethanol etc.), in the presence of catalyst to hydrogenate (e.g., Pd—C, palladium, palladium hydroxide, palladium acetate, palladium black, platinum black, Ni, Raney nickel etc.), at an ordinary or increased pressure under an atmosphere of hydrogen gas at 0~80° C.

As well known to the person in the art, a protecting group of carboxy or hydroxy includes, for example, t-butyl, benzyl etc. In addition, such a group includes the other protecting group which is removable selectively and easily, for example, one described in T. W. Greene, Protective Groups in Organic Synthesis, Wiley, New York, 1991. A protecting group of amino includes, for example, benzyloxycarbonyl, t-butoxycarbonyl. In addition, such a group includes the other protecting group which is removable selectively and easily. Further, the aimed compounds of the present invention may be prepared easily by choice of these protecting group.

The compounds of the formula (I) may be prepared by the methods described in Examples or by known methods.

The compounds of the formulae (II), (III), (IV), (V), (VI), (II), (VIII), (IX), (X), (XI), (XII), (XIII), (XIV), (XIV), (XVI), (XVII), (XVIII), (XVIV), (XVV) may be known per se or may be prepared by known methods or the methods described in Examples. But, the above compounds may be prepared by the other methods.

For example, the compounds of the formula (X) may be prepared by the method described in Liebigs Ann. Chem., 776-783, 1979.

For example, the compounds of the formula (XII) may be prepared by the method described in J. Org. Chem., Vol. 44, No. 10, 1979.

For example, the compounds of the formula (XIV), wherein E is —O—, —S—, —SO—, —SO$_2$—, i.e., the compounds of the formula (XIV') and the compounds of the formula (XVII), wherein E is —O—, —S—, —SO—, —SO$_2$—, i.e., the compounds of the formula (XVII') may be prepared by the method shown in the following Reaction Schemes 1 and 2.

In each Reaction Scheme, $E^5$ is —O—, —S—, —SO— or SO$_2$—, Boc is t-butoxycarbonyl, (Boc)$_2$O is di-t-butyl dicarbonate, $R^{60}$ is single bond or C1-3 alkylene and the other symbols are the same meanings as defined hereinbefore.

Reaction Scheme 1

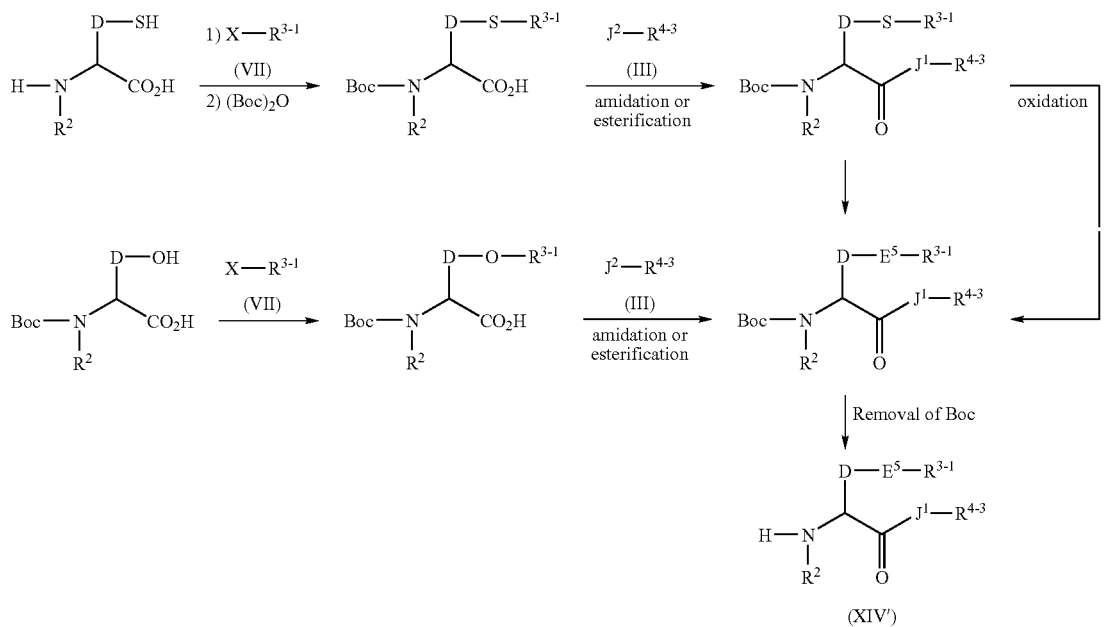

Reaction Scheme 2

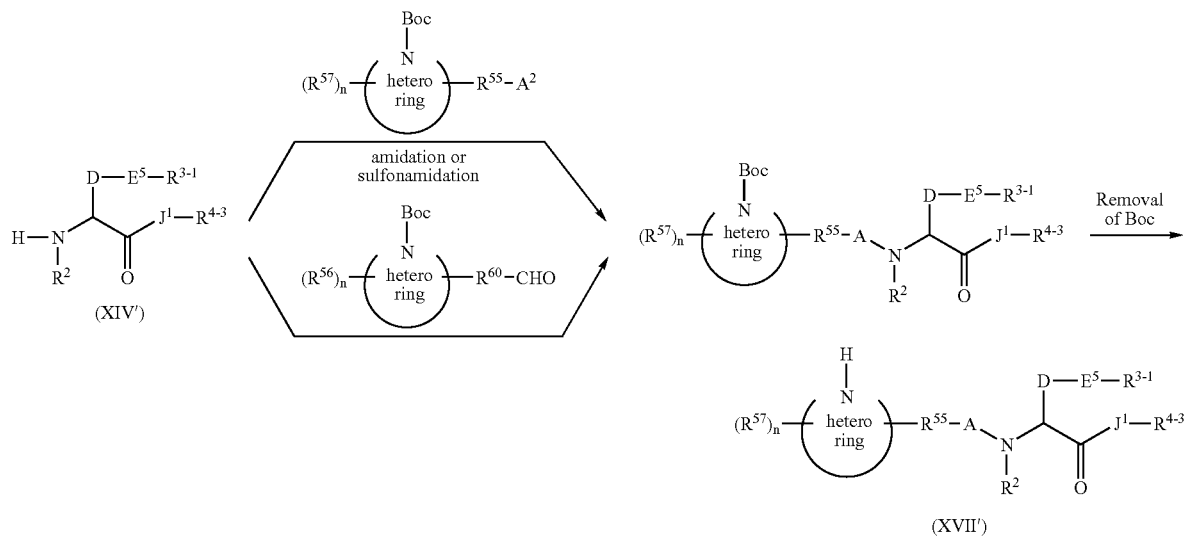

The reactions described in the above-mentioned Schemes may be carried out by known methods. In the above-mentioned Schemes, compounds used for starting materials are may be known per se or may be easily prepared by known methods.

In the present invention, the other starting materials and each reagent are known per se or may be prepared by known methods.

In each reaction in the present specification, products may be purified by a conventional manner. For example, it may be carried out by distillation at atmospheric or reduced pressure, high performance liquid chromatography, thin layer chromatography or column chromatography using silica gel or magnesium silicate, washing or recrystallization. Purification may be carried out after each reaction or after a series of reactions.

[Pharmacological Activity]

It has been confirmed that the compounds of the present invention of the formula (I) possess an inhibitory action on N-type calcium channel according to the following experiment.

Determination of Inhibitory Activity on N-type Calcium Channel:

Cell line was differentiated according to the method described in FEBS Lett. (1988) 235 178-182. The cell was loaded with fluorescent reagent, Fura-2·AM (at the final concentration of 10 μM), at 37° C. for 30 minutes and suspended in Krebs-buffer containing HEPES (25 mM) to obtain the cell suspension. The obtained cell suspension was incubated in the presence or absence of the compounds of the present invention with nifedipine for 5 minutes. The cell was depolarized by adding potassium chloride solution (at the final concentration of 80 mM) thereto and then a fluorescence intensity at the emission wavelength of 500 nm excited by the UV of 340 nm and 380 nm alternately was measured using the intracellular calcium analyzer (Nippon Bunko Co., CAF-110). The inhibitory activity of the compound of the present invention (at the final concentration of 3 μM) on calcium influx into the cell was calculated from the difference in changing the fluorescence intensity at peak (ΔR) according to the following equation.

$$\text{Inhibitory effect (\%) of the compound of the present invention (3 }\mu\text{M) on calcium flow} = \left(1 - \frac{\text{Mean of }\Delta R\text{ in case of a solution containing the compound of the present invention}}{\text{Mean of }\Delta R\text{ in case of a solution not containing the compound of the present invention}}\right) \times 100$$

The results were shown in Table 41.

TABLE 41

| Example No. | Inhibitory effect on calcium flow (%) |
|---|---|
| 11 | 81 |
| 11 (2) | 89 |

From the results of an experiment using the patch-clamp technique described in Pflugers Arch. (1981) 391 85-100, the compounds of the present invention at the concentration of 10 μM showed clearly an inhibitory action on flux of barium ion (calcium current) passed through an N-type calcium channel. The cells used in this experiment had been incubated according to the method described in FEBS Lett. (1988) 235 178-182.

[Toxicity]

The toxicity of the compounds of the present invention is very low and therefore, it may be considered that the compounds of the present invention are safe for pharmaceutical use.

INDUSTRIAL APPLICATION

[Application for Pharmaceuticals]

The compounds of the formula (I) possess an inhibitory action on N-type calcium channel, so they are useful as agent for the prevention and/or treatment of cerebral infarct, transient ischemic attack, encephalomyelopathy after cardiac operation, spinal angiopathy, hypertension with stress, neurosis, epilepsy, asthma and pollakiuria etc. or agent for the treatment of pain (for example, acute pain, chronic pain, pain after operation, cancer pain, neuralgia, pain caused by infection etc.).

For the purpose above described, the compounds of the present invention of the formula (I), non-toxic salts and acid addition salts thereof and hydrates thereof may be normally administered systematically or locally, usually by oral or parenteral administration.

The doses to be administered are determined depending upon age, body weight, symptom, the desired therapeutic effect, the route of administration, and the duration of the treatment etc. In the human adult, the doses per person per dose are generally between 1 mg and 1000 mg, by oral administration, up to several times per day, and between 0.1 mg and 100 mg, by parenteral administration (preferred into vein) up to several times per day, or continuous administration between 1 and 24 hrs. per day into vein.

As mentioned above, the doses to be used depend upon various conditions. Therefore, there are cases in which doses lower than or greater than the ranges specified above may be used.

The compounds of the present invention may be administered as inner solid compositions or inner liquid compositions for oral administration, or as injections, liniments or suppositories etc. for parenteral administration.

Inner solid compositions for oral administration include compressed tablets, pills, capsules, dispersible powders and granules etc. Capsules contain hard capsules and soft capsules.

In such inner solid compositions, one or more of the active compound(s) is or are, admixed with at least one inert diluent (lactose, mannitol, glucose, microcrystalline cellulose, starch etc.), connecting agents (hydroxypropyl cellulose, polyvinylpyrrolidone, magnesium metasilicate aluminate etc.), disintegrating agents (cellulose calcium glycolate etc.), lubricating agents (magnesium stearate etc.), stabilizing agents, assisting agents for dissolving (glutamic acid, asparaginic acid etc.) etc. to prepare pharmaceuticals by known methods. The pharmaceuticals may, if desired, be coated with material such as sugar, gelatin, hydroxypropyl cellulose or hydroxypropyl cellulose phthalate etc., or be coated with two or more films. And further, coating may include containment within capsules of absorbable materials such as gelatin.

Inner liquid compositions for oral administration include pharmaceutically acceptable water-agents, suspensions, emulsions, syrups and elixirs etc. In such liquid compositions, one or more of the active compound(s) is or are comprised in inert diluent(s) commonly used in the art (purified water, ethanol or mixture thereof etc.). Besides inert diluents, such compositions may also comprise adjuvants such as wetting agents, suspending agents, emulsifying agents, sweetening agents, flavoring agents, perfuming agents, preserving agents and buffer agents etc.

Injections for parenteral administration include solutions, suspensions and emulsions and solid injections which are dissolved or suspended in solvent when it is used. One or more active compound(s) is or are dissolved, suspended or emulsified in a solvent when such compositions are used. Aqueous solutions or suspensions include distilled water for injection and physiological salt solution, plant oil, propylene glycol, polyethylene glycol and alcohol such as ethanol etc., and mixture thereof. Such compositions may comprise additional diluents such as stabilizing agent, assisting agents for dissolving (glutamic acid, asparaginic acid, POLYSOLBATE80 (registered trade mark) etc.), suspending agents, emulsifying agents, dispersing agents, buffer agents, preserving agents etc. They may be sterilized for example, by filtration through a bacteria-retaining filter, by incorporation of sterilizing agents in the compositions or by irradiation. They may also be manufactured in the form of sterile solid compositions and which can be dissolved in sterile water or some other sterile diluent for injection immediately before use.

Other compositions for parenteral administration include liquids for external use, ointments, endermic liniments, aerosols, spray compositions, suppositories and pessaries for vaginal administration etc. which comprise one or more of the active compound(s) and may be prepared by known methods.

Spray compositions may comprise additional substances other than inert diluents: e.g. stabilizing agents such as sodium hydrogen sulfate, stabilizing agents to give isotonicity, isotonic buffer such as sodium chloride, sodium citrate, citric acid. For preparation of such spray compositions, for example, the method described in the U.S. Pat. Nos. 2,868,691 or 3,095,355 may be used.

BEST MODE FOR CARRYING OUT THE INVENTION

The following Reference Examples and Examples are intended to illustrate, but do not limit the present invention.

The solvents in parenthesis show the developing or eluting solvents and the ratios of the solvents used are by volume in chromatographic separations and TLC.

The solvents in parentheses in NMR show the solvents used for measurement.

REFERENCE EXAMPLE 1

(2R)-2-t-butoxycarbonylamino-3-cyclohexylmethylthiopropanoic acid

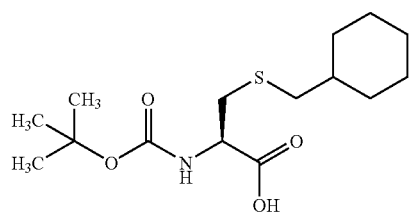

To a solution of L-cystein (133 mg) in ethanol (10 ml), an aqueous solution of 2N—NaOH (1.1 ml) and (bromomethyl)cyclohexane (0.17 ml) were added. The mixture was stirred for 2.5 hours at room temperature. To the reaction mixture, an aqueous solution of 2N—NaOH (0.6 ml) and di-t-butyl dicarbonate (0.28 ml) were added. The mixture was stirred for 1 hour. After ethanol was distilled off, the mixture was acidified by addition of 1N—HCl and extracted with ethyl acetate. The extract was washed by saturated solution of sodium chloride, dried over anhydrous magnesium sulfate and concentrated. The residue was purified with column chromatography on silica gel (chloroform:methanol=19:1) to obtain the title compound (135 mg) having the following physical data.

TLC: Rf 0.21 (ethyl acetate:acetic acid:water=9:1:1); NMR(CDCl$_3$): δ 4.42-4.28 (1H,m), 3.01 (1H,dd,J=14.2, 5.2 Hz), 2.92 (1H, dd,J=14.2, 3.4 Hz), 2.45 (2H,d,J=7.0 Hz), 1.91-0.81 (20H,m).

REFERENCE EXAMPLE 2

(2R)-N-(4-phenoxybenzyl)-2-t-butoxycarbonylamino-3-cyclohexylmethylthiopropanamide

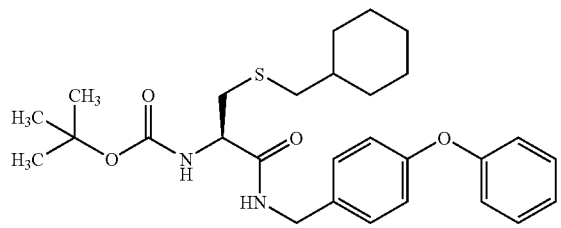

To a solution of a compound prepared in Reference Example 1 (4.64 g), 4-phenoxybenzylamine.hydrochloride (3.51 g) and triethylamine (2.1 ml) in methylene chloride (50 ml), 1-hydroxybenzotriazole (2.91 g) and 1-ethyl-3-(3-dimethylaminopropyl)-carbodiimide.hydrochloride (3.63 g) were added under cooling with ice successively. The mixture was stirred for 5 hours. The reaction mixture was washed by saturated solution of sodium hydrogen carbonate, 1N HCl, water and saturated solution of sodium chloride, successively, dried over anhydrous magnesium sulfate and concentrated. The residue was purified with column chromatography on silica gel (ethyl acetate:hexane=1:4) to obtain the title compound (5.26 g) having the following physical data.

TLC: Rf 0.67 (ethyl acetate:hexane=1:2); NMR(CDCl$_3$): δ 7.39-7.22 (m,4H), 7.15-7.06 (m,1H), 7.03-6.93 (m,4H), 6.70 (t,J=5.3 Hz,1H), 5.35 (d,J=6.8 Hz,1H), 4.44 (d,J=6.0 Hz,2H), 4.30-4.20 (m,1H), 2.99 (dd,J=14.0, 5.6 Hz,1H), 2.83 (dd, J=14.0, 7.0 Hz,1H), 2.52-2.36 (m,2H), 1.88-0.79 (m,20H).

REFERENCE EXAMPLE 3

(2R)-N-(4-phenoxybenzyl)-2-amino-3-cyclohexylmethylthiopropanamide.hydrochloride

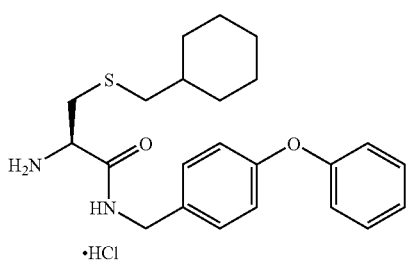

·HCl

To a solution of a compound prepared in Reference Example 2 (5.24 g) in dioxane (10 ml), a solution of 4N HCl-dioxane (50 ml) was added at room temperature. The mixture was stirred for 1 hour at room temperature. The reaction mixture was concentrated to obtain the crude title compound (4.36 g). The obtained crude compound was used in the next reaction without purification.

REFERENCE EXAMPLE 4

(2R)-N-(4-phenoxybenzyl)-3-cyclohexylmethylthio-2-((4R)-3-t-butoxycarbonylthiazolidin-4-ylcarbonylamino)propanamide

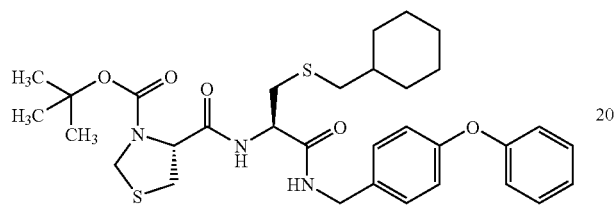

To a solution of a compound prepared in Reference Example 3 (814 mg), (4R)-3-t-butoxycarbonylthiazolidin-4-yl carboxylic acid (459 mg) and triethylamine (0.27 ml) in methylene chloride, 1-hydroxybenzotriazole and 1-ethyl-3-(3-dimethylaminopropyl)-carbodiimide.hydrochloride (431 mg) were added under cooling with ice successively. The mixture was stirred for 4 hours. The reaction mixture was washed by saturated solution of sodium hydrogen carbonate, 1N HCl, water and saturated solution of sodium chloride, successively, dried over anhydrous magnesium sulfate and concentrated. The residue was purified with column chromatography on silica gel (ethyl acetate:chloroform=1:9) to obtain the title compound (1.08 g) having the following physical data.

TLC: Rf 0.58 (ethyl acetate:hexane=1:1); NMR(CDCl$_3$): δ 7.36-7.23 (5H,m), 7.15-7.07 (2H,m), 7.01-6.91 (4H,m), 4.65-4.32 (6H,m), 3.33-3.13 (3H,m), 2.79 (1H,dd,J=14.1, 6.3 Hz), 2.45-2.30 (2H,m), 1.83-0.78 (20H,m).

REFERENCE EXAMPLE 5

(2R)-N-(4-phenoxybenzyl)-3-cyclohexylmethylthio-2-((4R)-thiazolidin-4-ylcarbonylamino)propanamide.hydrochloride

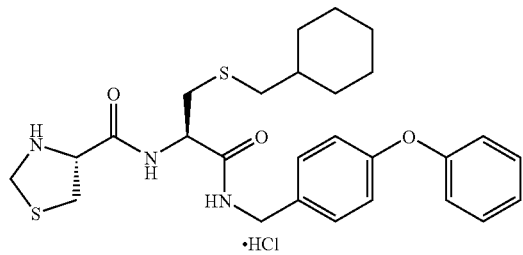

To a compound prepared in Reference Example 4 (322 mg), a solution of 4N HCl-dioxane (3 ml) was added at room temperature. The mixture was stirred for 1 hour. The reaction mixture was concentrated to obtain the title compound (263 mg) having the following physical data.

TLC: Rf 0.65 (ethyl acetate); NMR(CD$_3$OD): δ 8.71 (1H, t,J=5.7 Hz), 7.36-7.28 (4H,m), 7.09 (1H,t,J=7.2 Hz), 6.96-6.89 (4H,m), 4.59-4.51 (2H,m), 4.44-4.30 (4H,m), 3.55 (1H, dd,J=11.7,7.5 Hz), 3.24 (1H,dd,J=11.7, 6.9 Hz), 2.93 (1H,dd, J=13.5, 6.3 Hz), 2.81 (1H,dd,J=13.5, 7.5 Hz), 2.46 (1H,dd, J=12.6, 6.9 Hz), 2.42 (1H,dd,J=12.6, 6.6 Hz), 1.88-1.79 (2H, m), 1.74-1.61 (3H,m), 1.53-1.36 (1H,m), 1.31-1.08 (3H,m), 1.00-0.88 (2H,m).

REFERENCE EXAMPLE 6

(2R)-N-(4-phenoxybenzyl)-3-cyclohexylmethylthio-2-((4R)-thiazolidin-4-ylcarbonylamino)propanamide

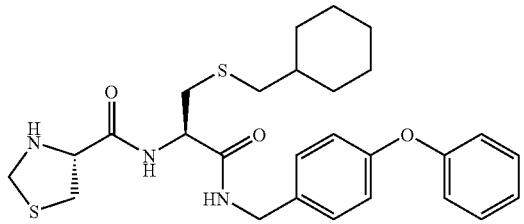

A solution of a compound prepared in Reference Example 5 (107 mg) in ethyl acetate (10 ml) was washed by saturated solution of sodium hydrogen carbonate (5 ml) and saturated solution of sodium chloride, successively, dried over anhydrous magnesium sulfate and concentrated to obtain the title compound (96 mg) having the following physical data.

TLC: Rf 0.39 (ethyl acetate:hexane=1:1); NMR(CDCl$_3$): δ 7.88 (d,J=7.5 Hz,1H), 7.37-7.30 (m,2H), 7.25-7.21 (m,2H), 7.14-7.08 (m,1H), 7.02-6.94 (m,4H), 6.84-6.80 (m,1H), 4.49-4.36 (m,3H), 4.26 (d,J=9.9 Hz,1H), 4.19-4.15 (m,1H), 4.05 (d,J=9.9 Hz,1H), 3.42 (dd, J=11.1, 4.2 Hz,1H), 3.10 (dd, J=11.1, 7.5 Hz,1H), 2.93 (dd,J=13.8, 6.3 Hz,2H), 2.83 (dd, J=13.8, 7.2 Hz,m), 2.45 (d,J=6.6 Hz,2H), 1.86-1.58 (m,5H), 1.51-1.36 (m,1H), 1.29-1.05 (3H,m), 0.98-0.85 (m,2H).

EXAMPLE 1

(2R)-N-(4-phenoxybenzyl)-3-cyclohexylmethylthio-2-((4R)-3-methoxymethylcarbonylthiazolidin-4-ylcarbonylamino)propanamide

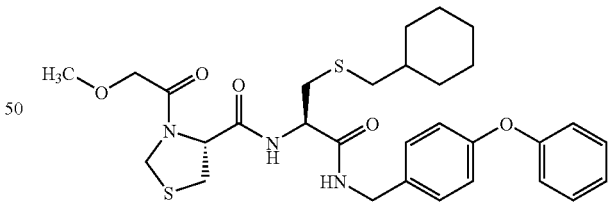

A compound prepared in Reference Example 6 (170 mg) and triethylamine (55 μl) were dissolved into methylene chloride (4 ml). Thereto, methoxyacetyl chloride (37 μl) was added. The mixture was stirred for 2.5 hours at room temperature. The reaction mixture was concentrated. The residue was purified with column chromatography on silica gel (chloroform:methanol=50:1) to obtain the compound (172 mg) of the present invention having the following physical data.

TLC: Rf 0.44 (chloroform:methanol=19:1); NMR (DMSO-d$_6$): δ 8.11 (br,1H), 7.89 (br,1H), 7.38-7.34 (m,2H), 7.29-7.27 (m,2H), 7.13-7.09 (m,1H), 6.99-6.93 (m,4H), 4.89 (dd,J=7.5, 4.0 Hz,1H), 4.78 (d,J=9.5 Hz,1H), 4.48-4.42 (m,2H), 4.29 (d,J=6.0 Hz,2H), 4.12-4.01 (m,2H), 3.30 (s,3H), 3.34-3.27 (m,1H), 3.17-3.07 (m,1H), 2.89 (dd,J=13.5, 6.3 Hz,1H), 2.76 (dd,J=13.5, 7.5 Hz,1H), 246-2.39 (m,2H), 1.78-1.72 (m,2H), 1.68-1.56 (m,3H), 1.47-1.38 (m,1H), 1.26-1.08 (m,3H), 0.99-0.90 (m,2H).

EXAMPLE 1 (1)~EXAMPLE 1 (14)

By the same procedure described in Example 1, using a compound prepared in Reference Example 6 and (2R)-N-(4-methoxybenzyl)-3-cyclohexylmethylthio-2-((4R)-thiazolidin-4-ylcarbonylamino)propanamide, (2R)-N-(4-nitrobenzyl)-3-cyclohexylmethylthio-2-((4R)-thiazolidin-4-ylcarbonylamino)propanamide and (2R)-N-(1-benzylpiperidin-4-yl)-3-cyclohexylmethylthio-2-((4R)-thiazolidin-4-ylcarbonylamino)propanamide prepared by the same procedures described in Reference Example 1→Reference Example 2→Reference Example 3→Reference Example 4→Reference Example 5→Reference Example 6, the following compounds of the present invention were obtained.

EXAMPLE 1 (1)

(2R)-N-(4-nitrobenzyl)-3-cyclohexylmethylthio-2-((4R)-3-(dimethylaminomethylcarbonyl)thiazolidin-4-ylcarbonylamino)propanamide

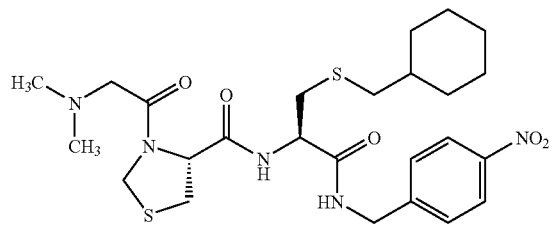

TLC: Rf 0.45 (methanol:chloroform=5:95); NMR (CDCl$_3$): δ 8.17 (2H,d,J=8.5 Hz), 7.49-7.44 (3H,m), 6.98 (1H,d,J=7.5 Hz), 4.88 (1H,d,J=9.5 Hz), 4.83 (1H,t,J=6.0 Hz), 4.80 (1H,d,J=9.5 Hz), 4.65-4.61 (1H,m), 4.58 (1H,dd,J=15.5, 6.0 Hz), 4.49 (1H,dd,J=15.5, 5.5 Hz), 3.30 (2H,d,J=6.0 Hz), 3.23 (1H,dd,J=14.0, 5.0 Hz), 3.20 (1H,d,J=6.0 Hz), 3.12 (1H,d,J=14.5 Hz), 2.82 (1H,dd, J=14.0, 5.5 Hz), 2.38 (1H,dd, J=13.0, 7.0 Hz), 2.30 (1H,dd,J=13.0, 6.5 Hz), 2.28 (6H,s), 1.82-1.62 (5H,m), 1.46-1.34 (1H,m), 1.27-1.06 (3H,m), 0.98-0.80 (2H,m).

EXAMPLE 1 (2)

(2R)-N-(4-methoxybenzyl)-3-cyclohexylmethylthio-2-((4R)-3-acetyloxymethylcarbonylthiazolidin-4-ylcarbonylamino)propanamide

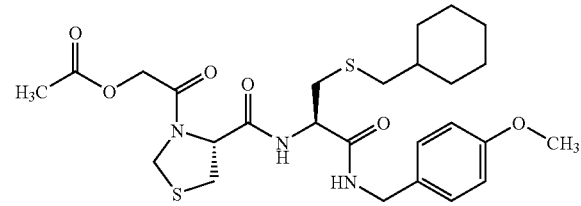

TLC: Rf 0.45 (hexane:ethyl acetate=1:8); NMR(CD$_3$OD): δ 7.24-7.19 (m,2H), 6.87-6.83 (m,2H), 4.95-4.40 (m,6H), 4.36 (d,J=16.0 Hz,1H), 4.26 (d,J=16.0 Hz,1H), 3.76 (s,3H), 3.40-3.30 (m,1H), 3.19-3.10 (m,1H), 2.97 (dd,J=14.0, 6.2 Hz,1H), 2.77 (dd,J=14.0, 8.4 Hz,1H), 2.41 (d, J=7.0 Hz,2H), 2.08 (s,3H), 1.90-1.55 (m,5H), 1.55-0.80 (m,6H).

EXAMPLE 1 (3)

(2R)-N-(1-benzylpiperidin-4-yl)-3-cyclohexylmethylthio-2-((4R)-3-(pyridin-3-ylcarbonyl)thiazolidin-4-ylcarbonylamino)propanamide

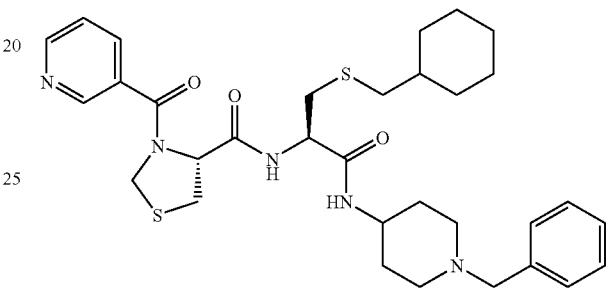

TLC: Rf 0.43 (chloroform:methanol=9:1); NMR (CD$_3$OD): δ 8.85-8.64 (m,2H), 8.15-7.95 (m,1H), 7.60-7.45 (m,1H), 7.33-7.18 (m,5H), 5.10-4.60 (m,3H), 4.52-4.35 (m,1H), 3.75-3.35 (m,2H), 3.51 (s,2H), 3.30-3.17 (m,1H), 3.00-2.70 (m,4H), 2.44 (d,J=6.6 Hz,2H), 2.22-2.04 (m,2H), 1.90-0.81 (m,15H).

EXAMPLE 1 (4)

(2R)-N-(1-benzylpiperidin-4-yl)-3-cyclohexylmethylthio-2-((4R)-3-acetyloxymethylcarbonylthiazolidin-4-ylcarbonylamino)propanamide

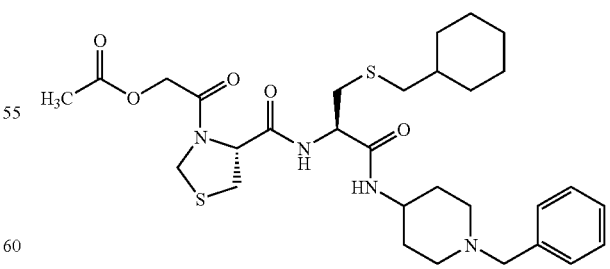

NMR(CD$_3$OD): δ 7.37-7.23 (m,5H), 4.90-4.35 (m,6H), 3.79-3.60 (m,1H), 3.64 (s,2H), 3.45-3.31 (m,1H), 3.22-3.09 (m,1H), 3.04-2.84 (m,3H), 2.75 (dd, J=13.7, 8.7 Hz,1H), 2.44 (d,J=6.6 Hz,2H), 2.37-2.20 (m,2H), 2.11 (s,3H), 1.96-0.82 (m,15H).

EXAMPLE 1 (5)

(2R)-N-(4-phenoxybenzyl)-3-cyclohexylmethylthio-2-((4R)-3-acetyloxymethylcarbonylthiazolidin-4-ylcarbonylamino)propanamide

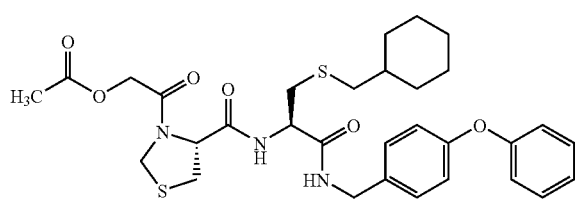

TLC: Rf 0.56 (chloroform:methanol=19:1); NMR (CD$_3$OD): δ 7.37-7.27 (m,4H), 7.13-7.02 (m,1H), 7.00-6.87 (m,4H), 4.90-4.44 (m,6H), 4.41 (d,J=15.6 Hz,1H), 4.12 (d,J=15.6 Hz,1H), 4.42-3.30 (m,1H), 3.20-3.10 (m,1H), 2.98 (dd,J=13.8, 6.2 Hz,1H), 2.79 (dd,J=13.8, 8.2 Hz,1H), 2.43 (d,J=7.0 Hz,2H), 2.08 (s,3H), 1.90-0.80 (m,11H).

EXAMPLE 1 (6)

(2R)-N-(4-phenoxybenzyl)-3-cyclohexylmethylthio-2-((4R)-3-(2-methoxyethoxymethylcarbonyl)thiazolidin-4-ylcarbonylamino)propanamide

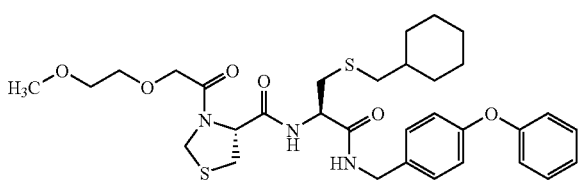

TLC: Rf 0.48 (chloroform:methanol=19:1); NMR (CD$_3$OD): δ 7.38-7.25 (m,4H), 7.13-7.04 (m,1H), 6.98-6.88 (m,4H), 4.87-4.10 (m,8H), 3.70-3.58 (m,2H), 3.58-3.48 (m,2H), 3.40-3.30 (m,1H), 3.33 (s,3H), 3.16-2.92 (m,2H), 2.80 (dd,J=13.6, 8.0 Hz,1H), 2.42 (d,J=7.0 Hz,2H), 1.90-0.80 (m,11H).

EXAMPLE 1 (7)

(2R)-N-(4-phenoxybenzyl)-3-cyclohexylmethylthio-2-((4R)-3-(pyridin-3-ylcarbonyl)thiazolidin-4-ylcarbonylamino)propanamide

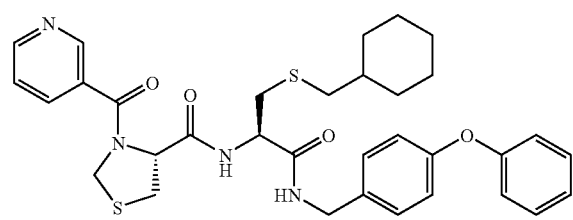

TLC: Rf 0.52 (chloroform:methanol=19:1); NMR (CD$_3$OD): δ 8.84-8.70 (m,1H), 8.69-8.63 (m,1H), 8.11-7.95 (m,1H), 7.58-7.44 (m,1H), 7.38-7.25 (m,4H), 7.13-7.05 (m,1H), 6.97-6.86 (m,4H), 5.10-4.41 (m,4H), 4.37 (s,2H), 3.51-3.40 (m,1H), 3.26-3.17 (m,1H), 3.10-2.70 (m,2H), 2.42 (d,J=7.0 Hz,2H), 1.90-0.80 (m,11H).

EXAMPLE 1 (8)

(2R)-N-(4-methoxybenzyl)-3-cyclohexylmethylthio-2-((4R)-3-(2-methyoxyacetyl)thiazolidin-4-ylcarbonylamino)propanamide

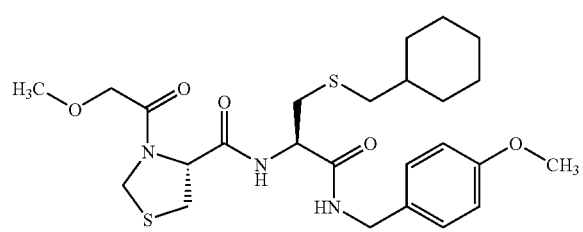

TLC: Rf 0.43 (chloroform:methanol=14:1); NMR (DMSO-d$_6$): δ 8.05 (brs,1H), 7.88 (brs,1H), 7.20-7.17 (m,2H), 6.87-6.84 (m,2H), 4.89 (dd,J=7.5, 4.0 Hz,1H), 4.79 (d,J=9.5 Hz,1H), 4.46-4.41 (m,2H), 4.23 (d,J=6.0 Hz,2H), 4.11 (d,J=15.0 Hz,1H), 4.06-4.01 (m,1H), 3.74 (s,3H), 3.33-3.28 (m,1H), 3.31 (s,3H), 3.15-3.11 (m,1H), 2.88 (dd,J=13.5, 5.8 Hz,1H), 2.75 (dd, J=13.5, 7.8 Hz,1H), 2.42 (d,J=6.0 Hz,2H), 1.79-1.70 (m,2H), 1.70-1.56 (m,3H), 1.47-1.37 (m,1H), 1.27-1.10 (m,3H), 1.00-0.89 (m,2H).

EXAMPLE 1 (9)

(2R)-N-(1-benzylpiperidin-4-yl)-3-cyclohexylmethylthio-2-((4R)-3-(2-methoxyacetyl)thiazolidin-4-ylcarbonylamino)propanamide

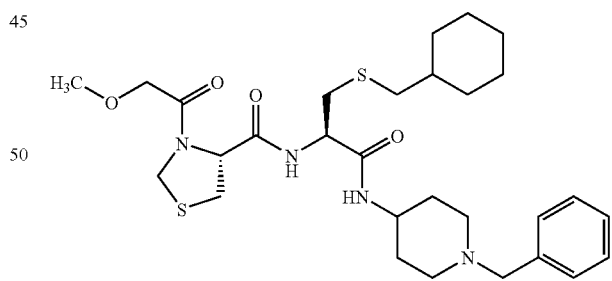

TLC: Rf 0.36 (chloroform:methanol=14:1); NMR (DMSO-d$_6$): δ 7.80 (brs,1H), 7.44 (brs,1H), 7.32-7.26 (m,4H), 7.24-7.20 (m,1H), 4.87 (dd,J=7.3, 4.3 Hz,1 H), 4.79 (d,J=9.5 Hz,1H), 4.46 (d,J=9.5 Hz,1H), 4.39-4.34 (m,1H), 4.12 (d,J=14.0 Hz,1H), 4.08-4.02 (m,1H), 3.60-3.51 (m,1H, 3.46 (s,2H), 3.33 (s,3H), 3.31 (dd,J=11.8, 7.3 Hz,1H), 3.13 (dd,J=11.8, 4.3 Hz,1H), 2.85 (dd,J=13.0, 6.3 Hz,1H), 2.72 (dd,J=13.0, 8.0 Hz,1H), 2.76-2.70 (m,2H), 2.43 (d, J=6.5 Hz,2H), 2.11-2.05 (m,2H), 1.80-1.56 (m,7H), 1.52-1.38 (m,3H), 1.27-1.09 (m,3H), 1.00-0.90 (m,2H).

EXAMPLE 1 (10)

(2R)-N-(1-benzylpiperidin-4-yl)-3-cyclohexylmethylthio-2-((4R)-3-allyloxycarbonylthiazolidin-4-ylcarbonylamino)propanamide

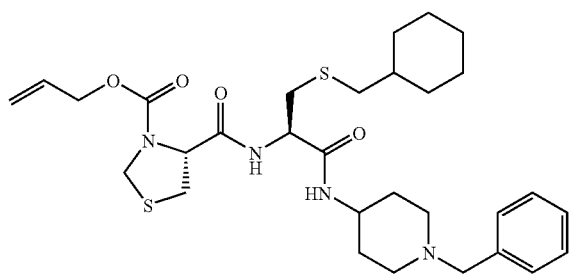

TLC: Rf 0.48 (chloroform:methanol=9:1); NMR (CD$_3$OD): δ 7.33-7.22 (m,5H), 6.05-5.85 (br,1H), 5.38-5.14 (br,2H), 4.72-4.49 (m,5H), 4.45 (dd,J=7.8, 6.3 Hz,1H), 3.70-3.60 (m,1H), 3.52 (s,2H), 3.39 (dd,J=11.7,7.2 Hz,1H), 3.16 (dd,J=11.7, 4.8 Hz,1H), 2.99-2.69 (br,4H), 2.44 (d, J=7.2 Hz,2H), 2.17-2.09 (m,2H), 1.85-1.36 (m,10H), 1.33-1.09 (m,3H), 1.01-0.87 (m,2H).

EXAMPLE 1 (11)

(2R)-N-(4-phenoxybenzyl)-3-cyclohexylmethylthio-2-((4R)-3-allyloxycarbonylthiazolidin-4-ylcarbonylamino)propanamide

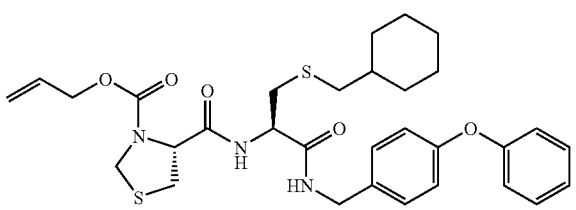

TLC: Rf 0.26 (hexane:ethyl acetate=2:1); NMR(CDCl$_3$): δ 7.37-6.93 (m,11H), 5.93-5.80 (m,1H), 5.32-5.21 (m,2H), 4.74-4.28 (m,8H), 3.32 (dd,J=12.0, 3.9 Hz,1H), 3.29 (dd, J=12.0, 6.6 Hz,1H), 3.22-3.04 (br,1H), 2.81 (dd,J=14.1, 6.6 Hz,1H), 2.47-2.34 (m,2H), 1.80-1.52 (m,5H), 1.48-1.04 (m,4H), 0.96-0.80 (m,2H).

EXAMPLE 1 (12)

(2R)-N-(4-methoxybenzyl)-3-cyclohexylmethylthio-2-((4R)-3-allyloxycarbonylthiazolidin-4-ylcarbonylamino)propanamide

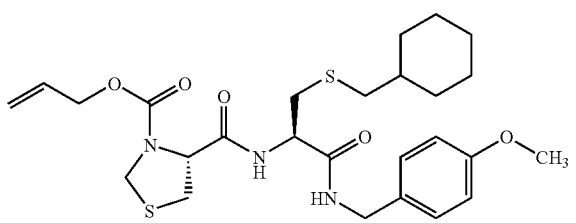

TLC: Rf 0.39 (hexane:ethyl acetate=1:1); NMR(CDCl$_3$): δ 7.20 (d,J=8.7 Hz,2H), 7.08 (d,J=7.8 Hz,2H), 6.84 (d, J=8.7 Hz,2H), 5.92-5.79 (m,1H), 5.30-5.20 (m,2H), 4.73-4.22 (m,8H), 3.78 (s,3H), 3.32 (dd,J=12.3, 4.2 Hz,1H), 3.28 (dd, J=12.3, 6.6 Hz,1H), 3.23-3.05 (br,1H), 2.80 (dd,J=13.8, 6.6 Hz,1H), 2.46-2.32 (m,2H), 1.78-1.58 (m,5H), 1.48-1.04 (m,4H), 0.95-0.81 (m,2H).

EXAMPLE 1 (13)

(2R)-N-(1-benzylpiperidin-4-yl)-3-cyclohexylmethylthio-((4R)-3-(2-ethoxy-1,2-dioxoethyl)thiazolidin-4-ylcarbonylamino)propanamide

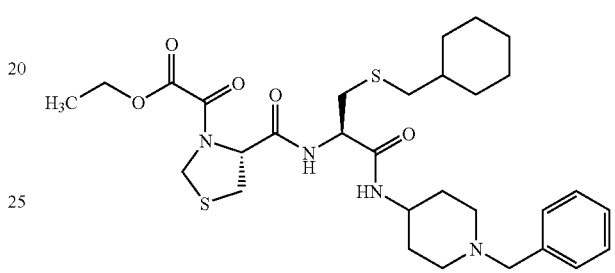

TLC: Rf 0.23 (methylene chloride:methanol=19:1).

EXAMPLE 1 (14)

(2R)-N-(1-benzylpiperidin-4-yl)-3-cyclohexylmethylthio-((4R)-3-phenylsulfonylthiazolidin-4-ylcarbonylamino)propanamide

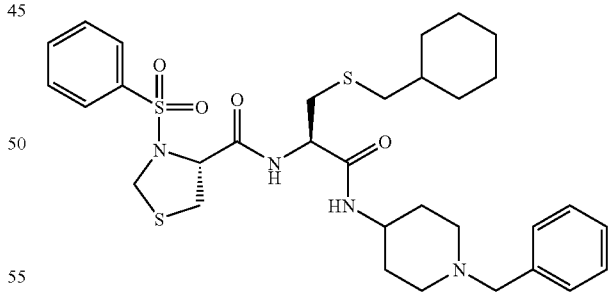

TLC: Rf 0.36 (methylene chloride:methanol=19:1); NMR (CD$_3$OD): δ 7.97-7.92 (m,2H), 7.78-7.57 (m,3H), 7.32-7.21 (m,5H), 4.75 (d,J=10.5 Hz,1H), 4.61 (d,J=10.5 Hz,1H), 4.52-4.46 (m,2H), 3.74-3.64 (m,1H), 3.51 (s,2H), 3.18 (dd,J=12.0, 5.4 Hz,1H), 3.03-2.77 (m,5H), 2.49-2.38 (m,2H), 2.18-2.09 (m,2H), 1.94-1.37 (m,10H), 1.33-1.08 (m,3H), 1.00-0.87 (m,2H).

EXAMPLE 2

(2R)-N-(4-phenoxybenzyl)-3-cyclohexylmethylthio-2-((4R)-3-(3-hydroxy-3-methylbutyryl)thiazolidin-4-ylcarbonylamino)propanamide

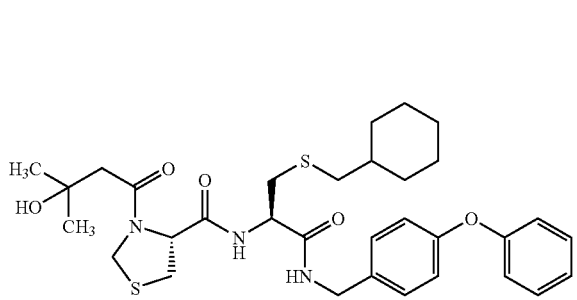

To a solution of 3-hydroxy-3-methylbutanoic acid (106 mg) in methylene chloride (5 ml), 1-hydroxy-7-azabenzotriazole (124 mg), a compound prepared in Reference Example 6 (231 mg) and 1-ethyl-3-(3-dimethylaminopropyl)-carbodiimide.hydrochloride (178 mg) were added under cooling with ice successively. The mixture was stirred overnight at room temperature. To the reaction mixture, saturated solution of sodium hydrogen carbonate (10 ml) was added. The mixture was extracted with methylene chloride (10 ml). The extract was washed by saturated solution of sodium chloride (15 ml), dried over anhydrous magnesium sulfate and concentrated. The residue was purified with column chromatography on silica gel (hexane:ethyl acetate=1:2) to obtain the compound (174 mg) of the present invention having the following physical data.

TLC: Rf 0.22 (hexane:ethyl acetate=1:2); NMR(DMSO-$d_6$,100° C.): δ 8.16-8.05 (br,1H), 7.92-7.76 (br,1H), 7.38-7.34 (m,2H), 7.28 (d,J=9.0 Hz,2H), 7.11 (t,J=7.5 Hz,1H), 6.99-6.92 (m,4H), 4.97-4.90 (br,1H), 4.85 (d,J=8.5 Hz,1H), 4.61-4.41 (br,2H), 4.29 (d,J=6.0 Hz,2H), 3.34-3.26 (br,1H), 3.18-3.12 (m,1H), 2.89 (dd,J=13.0, 5.5 Hz,1H), 2.75 (dd,J=13.0, 7.0 Hz,1H), 2.57-2.40 (m,4H), 1.77-1.74 (m,2H), 1.68-1.57 (m,3H), 1.47-1.38 (m,1H), 1.26-1.09 (m,9H), 0.98-0.91 (m,2H).

EXAMPLE 2 (1)~EXAMPLE 2 (7)

By the same procedure described in Example 2, using a compound prepared in Reference Example 6 and (2R)-N-(4-methoxybenzyl)-3-cyclohexylmethylthio-2-((4R)-thiazolidin-4-ylcarbonylamino)propanamide and (2R)-N-(1-benzylpiperidin-4-yl)-3-cyclohexylmethylthio-2-((4R)-thiazolidin-4-ylcarbonylamino)propanamide prepared by the same procedures described in Reference Example 1→Reference Example 2→Reference Example 3→Reference Example 4→Reference Example 5→Reference Example 6, the following compounds of the present invention were obtained.

EXAMPLE 2 (1)

(2R)-N-(4-methoxybenzyl)-3-cyclohexylmethylthio-2-((4R)-3-(2-hydroxy-2-methylpropionyl)thiazolidin-4-ylcarbonylamino)propanamide

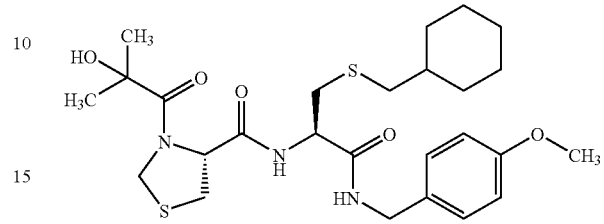

TLC: Rf 0.45 (chloroform:methanol=14:1); NMR (CD$_3$OD): δ 7.23-7.20 (2H,m), 6.87-6.83 (2H,m), 5.42-5.18 (1H,m), 4.93-4.62 (2H,m), 4.49-4.45 (1H,m), 4.40-4.23 (2H,m), 3.76 (3H,s), 3.38-2.80 (4H,m), 2.39 (2H,d,J=6.9 Hz), 1.84-1.59 (5H,m), 1.50-1.07 (4H,m), 1.39 (3H,s), 1.37 (3H,s), 0.98-0.83 (2H,m).

EXAMPLE 2 (2)

(2R)-N-(1-benzylpiperidin-4-yl)-3-cyclohexylmethylthio-2-((4R)-3-dimethylaminomethylcarbonylthiazolidin-4-ylcarbonylamino)propanamide

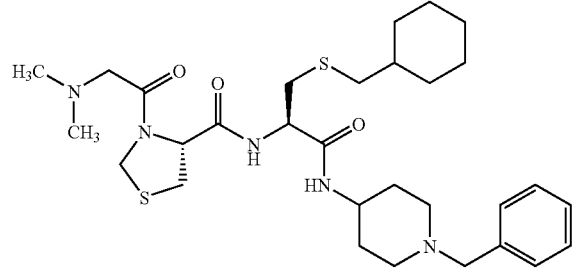

TLC: Rf 0.38 (chloroform:methanol=9:1); NMR (CD3OD): δ 7.35-7.20 (m,5H), 5.16-4.63 (m,4H), 4.54-4.35 (m,2H), 3.73-3.55 (m,1H), 3.52 (s,2H), 3.45-3.05 (m,2H), 2.96-2.70 (m,4H), 2.47-2.40 (m,2H), 2.32 and 2.27 (s,6H), 2.23-2.05 (m,2H), 1.90-0.80 (m,15H).

EXAMPLE 2 (3)

(2R)-N-(1-benzylpiperidin-4-yl)-3-cyclohexylmethylthio-2-((4R)-3-(morpholin-4-ylmethylcarbonyl)thiazolidin-4-ylcarbonylamino)propanamide

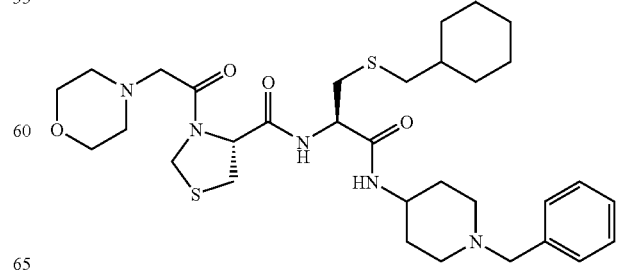

TLC: Rf 0.52 (chloroform:methanol=9:1); NMR(DMSO-$d_6$): δ 7.60 (br,1H), 7.36-7.20 (m,6H), 5.03-4.96 (m,1H), 4.92 (d,J=9.5 Hz,1H), 4.56-4.50 (m,1H), 4.40-4.35 (m,1H), 3.63-3.54 (m,5H), 3.49 (s,2H), 3.32-3.25 (m,2H), 3.18-3.14 (m,2H), 2.86 (dd,J=13.5, 6.0 Hz,1H), 2.80-2.72 (m,3H), 2.56-2.44 (m,4H), 2.44 (d,J=7.0 Hz,2H), 2.16-2.09 (m,2H), 1.80-1.56 (m,7H), 1.56-1.37 (m,3H), 1.28-1.10 (m,3H), 1.04-0.93 (m,2H).

EXAMPLE 2 (4)

(2R)-N-(1-benzylpiperidin-4-yl)-3-cyclohexylmethylthio-2-((4R)-3-(3-hydroxy-3-methylbutyryl)thiazolidin-4-ylcarbonylamino)propanamide

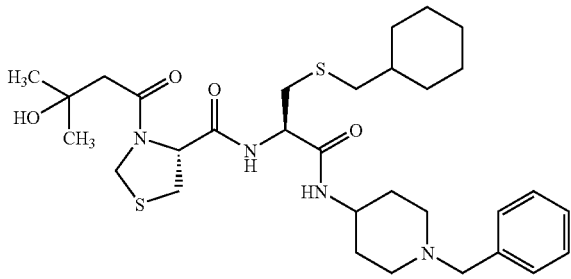

TLC: Rf 0.63 (chloroform:methanol=9:1); NMR(DMSO-$d_6$): δ 7.63 (br,1H), 7.34-7.20 (m,6H), 4.94 (dd,J=7.2, 4.0 Hz,1H), 4.86 (d,J=8.5 Hz,1H), 4.58-4.50 (m,1H), 4.40-4.33 (m,2H), 3.62-3.53 (m,1H), 3.49 (s,2H), 3.31 (dd,J=12.0, 7.2 Hz,1H), 3.17 (dd,J=12.0, 4.0 Hz,1H), 2.86 (dd, J=13.0, 6.0 Hz,1H), 2.78-2.72 (m,3H), 2.63-2.53 (m,2H), 2.45 (d,J=6.5 Hz,2H), 2.16-2.10 (m,2H), 1.80-1.56 (m,7H), 1.56-1.40 (m,3H), 1.30-1.10 (m,3H), 1.25 (s,6H), 1.03-0.94 (m,2H).

EXAMPLE 2 (5)

(2R)-N-(4-phenoxybenzyl)-3-cyclohexylmethylthio-2-((4R)-3-(2-dimethylaminoacetyl)thiazolidin-4-ylcarbonylamino)propanamide

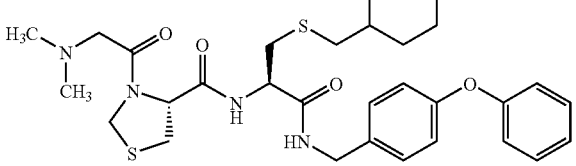

TLC: Rf 0.44 (chloroform:methanol=9:1); NMR(DMSO-$d_6$): δ 8.63-8.45 and 8.16-8.14 (m,2H), 7.39-7.25 (m,4H), 7.13-7.08 (m,1H), 6.97-6.92 (m,4H), 5.17-5.14 and 4.91-4.74 (m,2H), 4.56-4.21 (m,4H), 3.38-3.14 (m,2H), 3.05-2.92 (m,2H), 2.85-2.76 (m,1H), 2.70-2.59 (m,1H), 2.43-2.34 (m,2H), 2.16-2.14 (m,6H), 1.74-1.54 (m,5H), 1.43-1.29 (m,1H), 1.21-0.99 (m,3H), 0.92-0.79 (m,2H).

EXAMPLE 2 (6)

(2R)-N-(4-phenoxybenzyl)-3-cyclohexylmethylthio-2-((4R)-3-(2-hydroxy-2-methylpropionyl)thiazolidin-4-ylcarbonylamino)propanamide

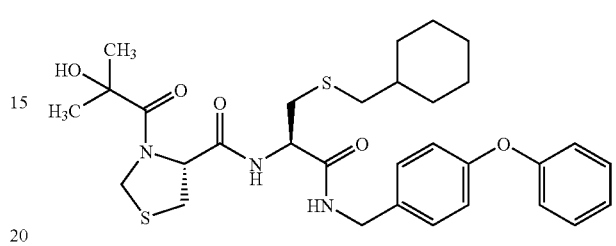

TLC: Rf 0.28 (hexane:ethyl acetate=1:2); NMR(DMSO-$d_6$,100° C.): δ 7.38-7.33 (m,2H), 7.28 (d,J=8.5 Hz,2H), 7.11 (t,J=7.5 Hz,1H), 6.98-6.91 (m,4H), 5.28 (d,J=10.0 Hz,1H), 5.21-5.12 (br,1H), 4.54 (d,J=10.0 Hz,1H), 4.43 (t,J=6.5 Hz,1H), 4.28 (s,2H), 3.22 (dd,J=11.5, 7.0 Hz,1H), 3.12 (dd, J=11.5, 4.5 Hz,1H), 2.88 (dd,J=13.5, 6.0 Hz,1H), 2.80 (dd, J=13.5, 7.0 Hz,1H), 2.44-2.40 (m,2H), 1.77-1.72 (m,2H), 1.68-1.56 (m,3H), 1.47-1.33 (m,7H), 0.98-0.89 (m,2H).

EXAMPLE 2 (7)

(2R)-N-(4-phenoxybenzyl)-3-cyclohexylmethylthio-2-((4R)-3-(morpholin-4-ylmethylcarbonyl)thiazolidin-4-ylcarbonylamino)propanamide

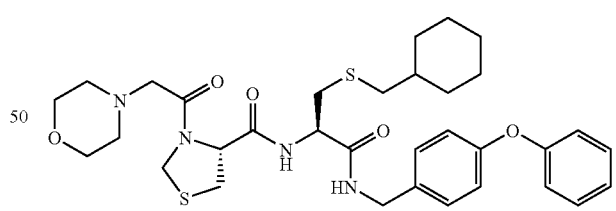

TLC: Rf 0.46 (chloroform:methanol=9:1); NMR(DMSO-$d_6$,100° C.): δ 8.18-8.10 (br,1H), 7.90-7.77 (br,1H), 7.38-7.34 (m,2H), 7.29 (d,J=8.5 Hz,2H), 7.11 (t,J=7.5 Hz,1H), 6.99-6.92 (m,4H), 5.12-4.90 (br,2H), 4.57-4.43 (br,2H), 4.29 (d,J=6.0 Hz,2H), 3.56 (t,J=5.0 Hz,4H), 3.31-3.22 (m,2H), 3.15-3.10 (m,2H), 2.88 (dd,J=13.5, 6.0 Hz,1H), 2.76 (dd, J=13.5, 7.5 Hz,1H), 2.47-2.41 (m,6H), 1.77-1.74 (m,2H), 1.68-1.57 (m,3H), 1.47-1.38 (m,1H), 1.25-1.09 (m,3H), 0.98-0.91 (m,2H).

EXAMPLE 3

(2R)-N-(4-phenoxybenzyl)-3-cyclohexylmethylthio-2-((4R)-3-carboxymethylthiazolidin-4-ylcarbonylamino)propanamide.hydrochloride

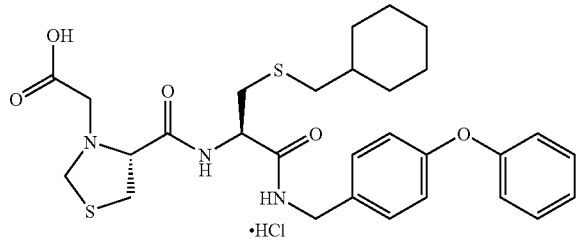

A compound prepared in Reference Example 6 (300 mg) and 40% glyoxalic acid (1.0 ml) were dissolved into a mixture solution of methylene chloride (4 ml) and ethanol (10 ml). Thereto, sodium cyanoboro hydride (124 mg) was added. The mixture was adjustified to pH 5.5 by addition of an aqueous solution of 1N—NaOH and then stirred for 3 hours at room temperature. The reaction mixture was concentrated. The residue was purified with column chromatography on silica gel (chloroform:methanol=20:1). The purified product was dissolved into ethyl acetate (5 ml). Thereto, a solution of 4N HCl-ethyl acetate (0.25 ml) was added. After stirring the mixture, a solvent was distilled off to obtain the compound (260 mg) of the present invention having the following physical data.

NMR(CD$_3$OD): δ 7.38-7.26 (m,4H), 7.13-7.04 (m,1H), 6.97-6.88 (m,4H), 4.64 (d,J=10.6 Hz,1H), 4.55 (dd,J=8.2, 6.0 Hz,1H), 4.48 (dd,J=7.7, 5.4 Hz,1H), 4.38-4.32 (m,3H), 4.12 (d,J=17.2 Hz,1H), 4.00 (d,J=17.2 Hz,1H), 3.50 (dd,J=11.7, 7.7 Hz,1H), 3.34 (dd,J=11.7, 5.4 Hz 1H), 2.96 (dd,J=13.6, 6.0 Hz,1H), 2.82 (dd,J=13.6, 8.2 Hz,1H), 2.44 (d,J=6.8 Hz,2H), 1.90-0.80 (m,11H).

EXAMPLE 3 (1)~EXAMPLE 3 (13)

By the same procedure described in Example 3, using a compound prepared in Reference Example 6 and (2R)-N-(4-methoxybenzyl)-3-cyclohexylmethylthio-2-((4R)-thiazolidin-4-ylcarbonylamino)propanamide and (2R)-N-(1-benzylpiperidin-4-yl)-3-cyclohexylmethylthio-2-((4R)-thiazolidin-4-ylcarbonylamino)propanamide prepared by the same procedures described in Reference Example 1→Reference Example 2→Reference Example 3→Reference Example 4→Reference Example 5→Reference Example 6 (provided that the procedure to obtain hydrochloride was not carried out), the following compounds of the present invention were obtained.

EXAMPLE 3 (1)

(2R)-N-(4-nitrobenzyl)-3-cyclohexylmethylthio-2-((4R)-3-(3-methylbutyl)thiazolidin-4-ylcarbonylamino)propanamide

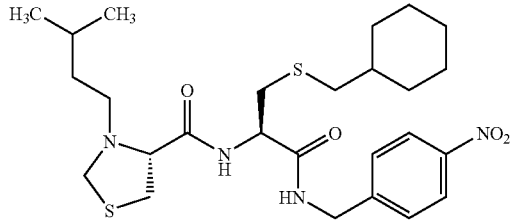

TLC: Rf 0.66 (ethyl acetate:hexane 1:1); NMR(CDCl$_3$): δ 8.22-8.16 (2H,m), 7.96 (1H,d,J=7.4 Hz), 7.48-7.42 (2H,m), 7.13 (1H,t,J=6.6 Hz), 4.60 (1H,dd,J=15.8, 5.8 Hz), 4.51 (1H, dd,J=15.8, 6.4 Hz), 4.50-4.39 (1H,m), 4.11 (1H,d,J=10.4 Hz) 3.99 (1H,dd,J=10.4, 0.6 Hz), 3.90 (1H,dd,J=7.4, 2.4 Hz), 3.51 (1H,dd,J=11.0, 2.4 Hz), 3.07 (1H,dd,J=11.0, 7.4 Hz), 2.96 (1H,dd,J=13.6, 6.6 Hz), 2.84 (1H,dd,J=13.6, 7.0 Hz), 2.70-2.41 (4H,m), 1.88-0.80 (20H,m).

EXAMPLE 3 (2)

(2R)-N-(4-methoxybenzyl)-3-cyclohexylmethylthio-2-((4R)-3-(2-hydroxyethyl)thiazolidin-4-ylcarbonylamino)propanamide

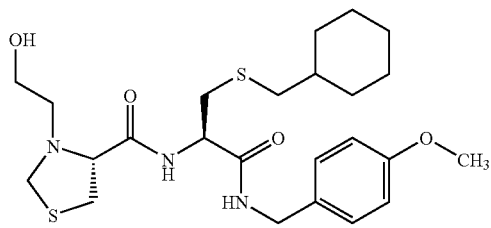

TLC: Rf 0.61 (chloroform:methanol=9:1); NMR (CD$_3$OD): δ 7.22-7.19 (2H,m), 6.87-6.84 (2H,m), 4.49 (1H, dd,J=8.6, 5.1 Hz), 4.37-4.24 (3H,m), 4.11-4.06 (2H,m), 3.77-3.62 (2H,m), 3.76 (3H,s), 3.42 (1H,dd,J=10.8, 2.6 Hz), 3.07 (1H,dd,J=10.8, 7.5 Hz), 2.96 (1H, dd,J=14.1, 5.1 Hz), 2.80 (1H,dd,J=14.1, 8.6 Hz), 2.80-2.61 (2H,m), 2.44-2.33 (2H,m), 1.80-1.60 (5H,m), 1.50-1.07 (4H,m), 0.99-0.83 (2H,m).

EXAMPLE 3 (3)

(2R)-N-(1-benzylpiperidin-4-yl)-3-cyclohexylmethylthio-2-((4R)-3-(2-hydroxyethyl)thiazolidin-4-ylcarbonylamino)propanamide

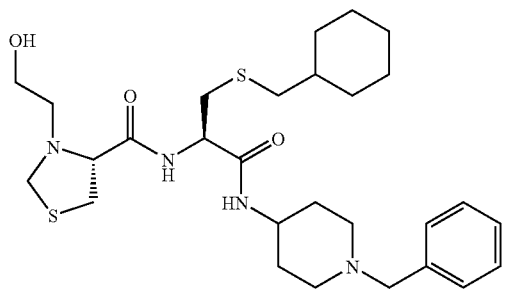

TLC: Rf 0.48 (chloroform:methanol=9:1); NMR (CD$_3$OD): δ 7.34–7.20 (m,5H), 4.44 (dd,J=8.4, 5.4 Hz,1H), 4.24 (d,J=10.2 Hz,1H), 4.09–4.04 (m,2H), 3.80–3.57 (m,3H), 3.52 (s,2H), 3.39 (dd, J=10.8, 2.3 Hz,1H), 3.09 (dd,J=10.8, 7.4 Hz,1H), 2.96–2.60 (m,6H), 2.42 (d,J=7.0 Hz,2H), 2.20–2.04 (m,2H), 1.90–0.82 (m,15H).

EXAMPLE 3 (4)

(2R)-N-(4-methoxybenzyl)-3-cyclohexylmethylthio-2-((4R)-3-(3-hydroxy-3-methylbutyl)thiazolidin-4-ylcarbonylamino)propanamide

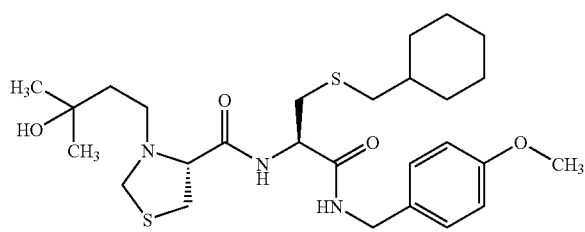

TLC: Rf 0.40 (chloroform:methanol=19:1); NMR (CD$_3$OD): δ 7.24–7.19 (m,2H), 6.88–6.83 (m,2H), 4.47 (dd, J=7.5, 5.7 Hz,1H), 4.39–4.23 (m,2H), 4.20 (d,J=10.2 Hz,1H), 4.12–4.02 (m,2H), 3.76 (s,3H), 3.42 (dd,J=10.6, 2.6 Hz,1H), 3.07 (dd,J=10.6, 7.6 Hz,1H), 3.00–2.60 (m,4H), 2.38 (d,J=7.0 Hz,2H), 1.87–0.80 (m,13H), 1.21 (s,6H).

EXAMPLE 3 (5)

(2R)-N-(1-benzylpiperidin-4-yl)-3-cyclohexylmethylthio-2-((4R)-3-(3-hydroxy-3-methylbutyl)thiazolidin-4-ylcarbonylamino)propanamide

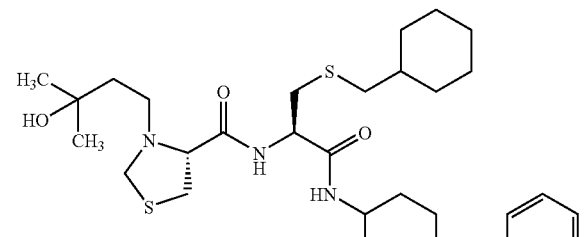

TLC: Rf 0.69 (chloroform:methanol=9:1); NMR (CD$_3$OD): δ 7.34–7.20 (m,5H), 4.42 (dd,J=7.4, 5.6 Hz,1H), 4.19 (d,J=10.2 Hz,1H), 4.07–4.02 (m,2H), 3.74–3.56 (m,1H), 3.53 (s,2H), 3.41 (dd,J=10.6, 2.6 Hz,1H), 3.07 (dd,J=10.6, 7.4 Hz,1H), 2.95–2.60 (m,6H), 2.41 (d,J=7.0 Hz,2H), 2.22–2.05 (m,2H), 1.91–0.82 (m,17H), 1.21 (s,6H).

EXAMPLE 3 (6)

(2R)-N-(1-benzylpiperidin-4-yl)-3-cyclohexylmethylthio-2-((4R)-3-(3-hydroxypropyl)thiazolidin-4-ylcarbonylamino)propanamide

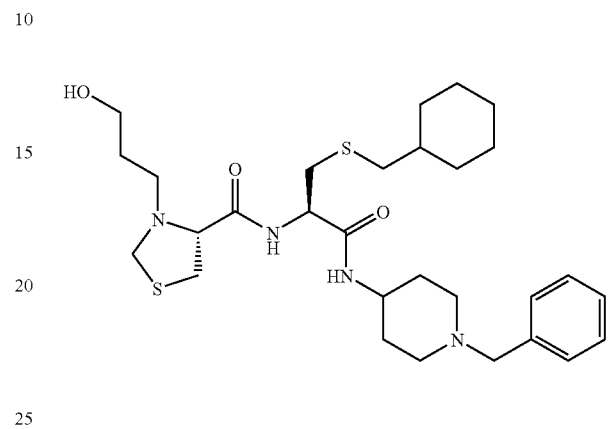

TLC: Rf 0.46 (chloroform:methanol=9:1); NMR (CD$_3$OD): δ 7.35–7.20 (m,5H), 4.42 (dd,J=7.4, 5.8 Hz,1H), 4.21–4.16 (m,1H), 4.06–4.01 (m,2H), 3.76–3.56 (m,3H), 3.53 (s,2H), 3.40 (dd, J=10.6, 2.5 Hz,1H), 3.07 (dd,J=10.6, 7.4 Hz,1H), 2.96–2.58 (m,6H), 2.41 (d,J=7.0 Hz,2H), 2.21–2.05 (m,2H), 1.90–0.82 (m,17H).

EXAMPLE 3 (7)

(2R)-N-(1-benzylpiperidin-4-yl)-3-cyclohexylmethylthio-2-((4R)-3-carboxymethylthiazolidin-4-ylcarbonylamino)propanamide

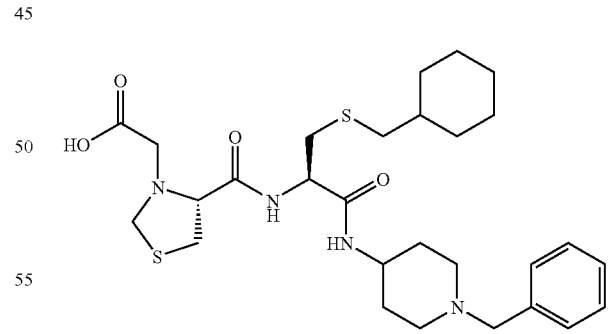

TLC: Rf 0.22 (chloroform:methanol=9:1), NMR (CD$_3$OD): δ 7.55–7.43 (m,5H), 4.47 (dd,J=8.0, 5.2 Hz,1H), 4.28 (s,2H), 4.24 (d,J=10.2 Hz,1H), 4.04 (d,J=10.2 Hz,1H), 4.00–3.89 (m,2H), 3.56–3.22 (m,6H), 3.14–2.86 (m,4H), 2.42 (d,J=6.6 Hz,2H), 2.10–0.80 (m,15H).

EXAMPLE 3 (8)

(2R)-N-(4-phenoxybenzyl)-3-cyclohexylmethylthio-2-((4R)-3-(2-hydroxyethyl)thiazolidin-4-ylcarbonylamino)propanamide

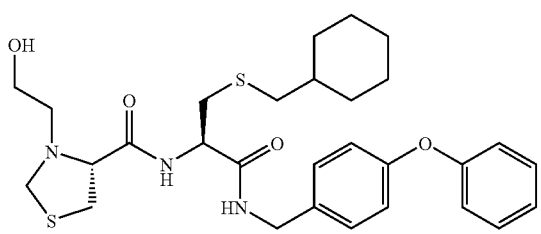

TLC: Rf 0.41 (chloroform:methanol=19:1); NMR (CD$_3$OD): δ 7.33-7.09 (m,4H), 7.13-7.04 (m,1H), 6.97-6.89 (m,4H), 4.50 (dd,J=8.4, 5.3 Hz,1H), 4.36 (s,2H), 4.26 (d,J=10.0 Hz,1H), 4.13-4.05 (m,2H), 3.80-3.60 (m,2H), 3.43 (dd,J=10.7, 2.8 Hz,1H), 3.08 (dd,J=10.7, 7.5 Hz,1H), 2.99 (dd, J=14.0, 5.3 Hz,1H), 2.81 (dd,J=14.0, 8.4 Hz,1H), 2.82-2.58 (m,2H), 2.40 (d,J=7.0 Hz,2H), 1.88-0.80 (m, 11H).

EXAMPLE 3 (9)

(2R)-N-(4-phenoxybenzyl)-3-cyclohexylmethylthio-2-((4R)-3-(2,3-dihydroxypropyl)thiazolidin-4-ylcarbonylamino)propanamide

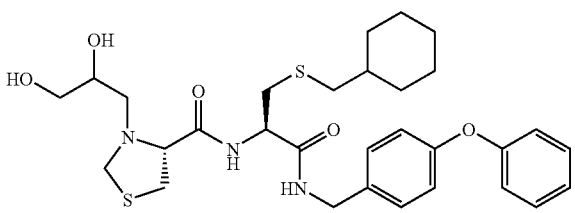

TLC: Rf 0.27 (chloroform:methanol=19:1); NMR (CDCl$_3$): δ 8.27 (brt,J=9.3 Hz,1H), 7.38-6.94 (m,10H), 4.58-4.39 (m,3H), 4.22-4.14 (m,1H), 4.00-3.12 (m,7H), 3.00-2.55 (m,4H), 2.44 (d,J=7.0 Hz,2H), 1.87-0.80 (m,11H).

EXAMPLE 3 (10)

(2R)-N-(4-phenoxybenzyl)-3-cyclohexylmethylthio-2-((4R)-3-(2-methoxyethyl)thiazolidin-4-ylcarbonylamino)propanamide

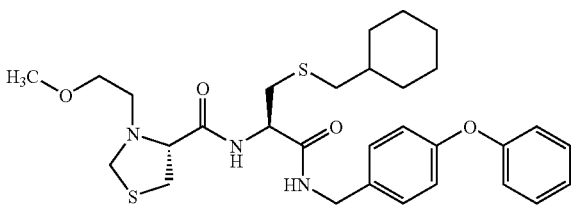

TLC: Rf 0.46 (chloroform:methanol=19:1); NMR (CD$_3$OD): δ 7.38-7.26 (m,4H), 7.14-7.05 (m,1H), 6.97-6.90 (m,4H), 4.49 (dd,J=7.6, 5.7 Hz,1H), 4.37 (s,2H), 4.20 (d,J=10.0 Hz,1H), 4.12-4.06 (m,2H), 3.61-3.54 (m,2H), 3.42-3.35 (m,1H), 3.34 (s,3H), 3.08 (dd,J=11.0, 7.6 Hz,1H), 2.96 (dd, J=13.7, 5.7 Hz,1H), 2.90-2.73 (m,3H), 2.41 (d,J=6.8 Hz,2H), 1.90-0.80 (m,11H).

EXAMPLE 3 (11)

(2R)-N-(4-phenoxybenzyl)-3-cyclohexylmethylthio-2-((4R)-3-(2,3-dimethyoxypropyl)thiazolidin-4-yl-carbonylamino)propanamide

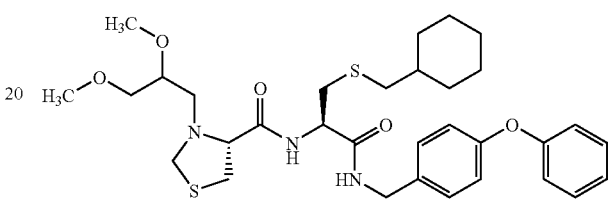

TLC: Rf 0.63 (chloroform:methanol=19:1); NMR (CD$_3$OD): δ 7.38-7.25 (m,4H), 7.13-7.05 (m,1H), 6.98-6.88 (m,4H), 4.55-4.46 (m,1H), 4.37 (s,2H), 4.21-4.04 (m,3H), 3.62-3.46 (m,3H), 3.42 and 3.41 (s,3H), 3.40-3.30 (m,1H), 3.35 and 3.34 (s,3H), 3.16-2.60 (m,5H), 2.40 (d, J=6.6 Hz,2H), 1.87-0.80 (m,11H).

EXAMPLE 3 (12)

(2R)-N-(4-phenoxybenzyl)-3-cyclohexylmethylthio-2-((4R)-3-(3-hydroxy-3-methylbutyl)thiazolidin-4-ylcarbonylamino)propanamide

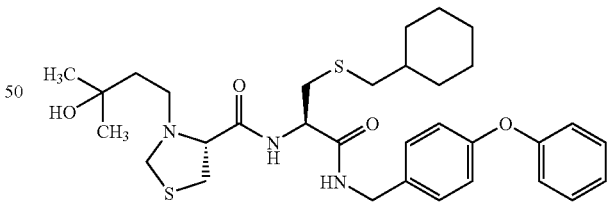

TLC: Rf 0.51 (chloroform:methanol=19:1); NMR (CD$_3$OD): δ 7.37-7.27 (m,4H), 7.14-7.05 (m,1H), 6.97-6.90 (m,4H), 4.48 (dd,J=7.5, 5.7 Hz,1H), 4.40 (d,J=14.9 Hz,1H), 4.33 (d,J=14.9 Hz,1H), 4.19 (d, J=9.9 Hz,1H), 4.10-4.03 (m,2H), 3.42 (dd,J=10.8, 2.6 Hz,1H), 3.07 (dd,J=10.8, 7.8 Hz,1H), 2.97 (dd,J=13.8, 5.7 Hz,1H), 2.83 (dd,J=13.8, 7.5 Hz,1H), 2.78-2.61 (m,2H), 2.39 (d,J=6.9 Hz,2H), 1.21 (s,3H), 1.20 (s,3H), 1.86-0.84 (m,13H).

EXAMPLE 3 (13)

(2R)-N-(4-phenoxybenzyl)-3-cyclohexylmethylthio-2-((4R)-3-(3-hydroxypropyl)thiazolidin-4-ylcarbonylamino)propanamide

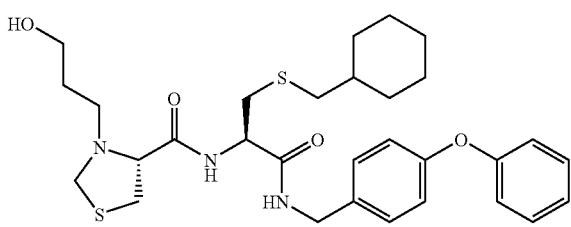

TLC: Rf 0.51 (chloroform:methanol=19:1); NMR (CD₃OD): δ 7.38-7.27 (m,4H), 7.14-7.04 (m,1H), 6.98-6.90 (m,4H), 4.49 (dd,J=7.4, 5.6 Hz,1H), 4.45-4.28 (m,2H), 4.19 (d,J=10.2 Hz,1H), 4.10-4.02 (m,2H), 3.75-3.67 (m,2H), 3.42 (dd,J=10.7, 2.5 Hz,1H), 3.07 (dd,J=10.7, 7.6 Hz,1H), 2.96 (dd, J=13.8, 5.6 Hz,1H), 2.84 (dd,J=13.8, 7.4 Hz,1H), 2.76-2.57 (m,2H), 2.39 (d,J=7.0 Hz,2H), 1.90-0.80 (m,13H).

EXAMPLE 4

(2R)-N-((1R)-1-(4-nitrophenyl)ethyl)-3-cyclohexylmethylthio-2-((4R)-3-t-butylcarbamoylthiazolidin-4-ylcarbonylamino)propanamide

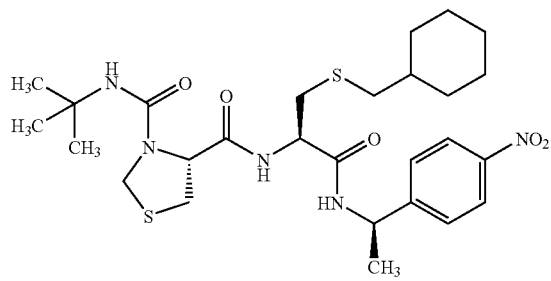

A solution of (2R)-N-((1R)-1-(4-nitrophenyl)ethyl)-3-cyclohexylmethylthio-2-((4R)-thiazolidin-4-ylcarbonylamino)propanamide.hydrochloride (109 mg) prepared by the same procedures described in Reference Example 1→Reference Example 2→Reference Example 3→Reference Example 4→Reference Example 5, t-butyl isocyanate (0.027 ml) and triethylamine (0.03 ml) in methylene chloride (3 ml) was refluxed overnight. The reaction mixture was washed by 1N HCl, water and saturated solution of sodium chloride, successively, dried over anhydrous magnesium sulfate and concentrated. The residue was purified with column chromatography on silica gel (ethyl acetate:hexane=1:2) to obtain the compound (86 mg) of the present invention having the following physical data.

TLC: Rf 0.31 (ethyl acetate:hexane=1:1); NMR(CDCl₃): δ 8.18-8.11 (2H,m), 7.78 (1H,d,J=7.4 Hz), 7.60-7.53 (2H,m), 7.22 (1H,d,J=8.8 Hz), 5.20-5.06 (1H,m), 4.75 (1H,q,J=3.2 Hz), 4.65 (1H,ddd, J=8.8, 5.6, 3.6 Hz) 4.50 (1H,s), 4.43 (1H,d,J=7.4 Hz), 4.38 (1H,d,J=7.4 Hz), 3.38 (1H, dd,J=12.2, 2.8 Hz), 3.29 (1H,dd,J=12.2, 6.2 Hz), 3.24 (1H,dd,J=13.6, 4.0 Hz), 2.77 (1H, dd,J=13.6, 5.6 Hz), 2.23 (1H,dd,J=12.4, 6.6 Hz), 2.13 (1H,dd,J=12.4, 7.0 Hz), 1.80-0.64 (23H,m).

EXAMPLE 5~EXAMPLE 5 (10)

By the same procedure described in Reference Example 1→Reference Example 2→Reference Example 3→Reference Example 4, the following compounds of the present invention were obtained.

With the proviso that, the compound of Example 5 (4) was prepared by the procedure comprising oxidation after reaction of Reference Example 2.

EXAMPLE 5

(2R)-N-(4-methoxybenzyl)-3-cyclohexylmethylthio-2-((2RS)-3-t-butoxycarbonyl-1-oxothiazolidin-2-ylcarbonylamino)propanamide

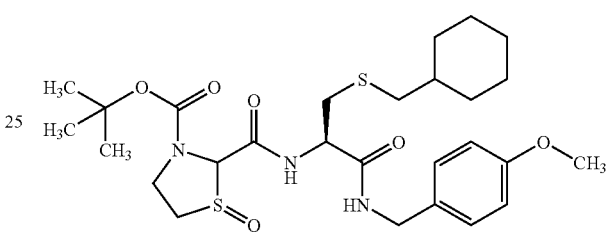

TLC: Rf 0.61, 0.52 (ethyl acetate); NMR(CD₃OD): δ 7.22-7.19 (2H,m), 6.87-6.83 (2H,m), 5.56-5.43 (1H,m), 4.53-4.46 (1H,m), 4.35-4.25 (2H,m), 4.18-4.09 (2H,m), 3.76-3.75 (3H, m), 3.36-3.22 (2H,m), 3.10-2.85 (2H,m), 2.79-2.69 (1H,m), 2.46-2.34 (2H,m), 1.86-0.84 (20H,m).

EXAMPLE 5 (1)

(2R)-N-(4-methoxybenzyl)-3-cyclohexylmethylthio-2-((2RS)-3-t-butoxycarbonyl-1,1-dioxothiazolidin-2-ylcarbonylamino)propanamide

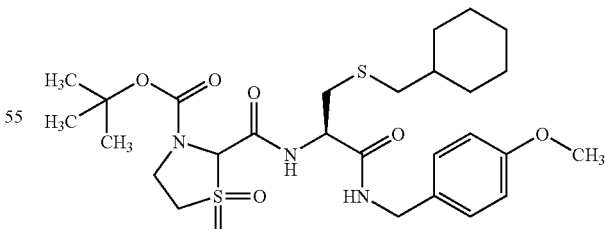

TLC: Rf 0.59 (methylene chloride:ethyl acetate=3:1); NMR(CD₃OD): δ 7.25-7.18 (2H,m), 6.87-6.80 (2H,m), 5.16-5.07 (1H,m), 4.58-4.50 (1H,m), 4.33-4.30 (2H,m), 4.07-3.96 (1H,m), 3.86-3.68 (1H,m), 3.75 (3H,s), 3.60-3.20 (2H,m), 3.07-2.73 (2H,m), 2.42 (2H,d,J=7.0 Hz), 1.89-1.60 (5H,m), 1.50-1.11 (4H,m), 1.46-1.39 (9H,m), 1.01-0.82 (2H,m).

EXAMPLE 5 (2)

(2R)-N-(4-methoxybenzyl)-3-cyclohexylmethylthio-2-((4R)-3-t-butoxycarbonyl-1,1-dioxothiazolidin-4-ylcarbonylamino)propanamide

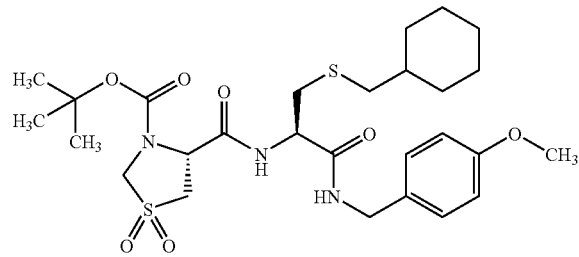

TLC: Rf 0.53 (methylene chloride:ethyl acetate=3:1); NMR(CD$_3$OD): δ 7.24-7.19 (2H,m), 6.88-6.83 (2H,m), 5.07-4.85 (1H,m), 4.75 (1H,dd,J=12.0, 1.7 Hz), 4.49 (1H,t,J=6.8 Hz), 4.37-4.30 (3H,m), 3.76 (3H,s), 3.75-3.50 (1H,m), 3.50-3.30 (1H,m), 2.97-2.73 (2H,m), 2.41 (2H,d,J=6.6 Hz), 1.87-1.55 (5H,m), 1.50-1.08 (4H,m), 1.47 (9H,s), 1.04-0.81 (2H, m).

EXAMPLE 5 (3)

(2R)-N-(4-methoxybenzyl)-3-cyclohexylmethylthio-2-((4R)-3-t-butoxycarbonyl-1-oxothiazolidin-4-ylcarbonylamino)propanamide

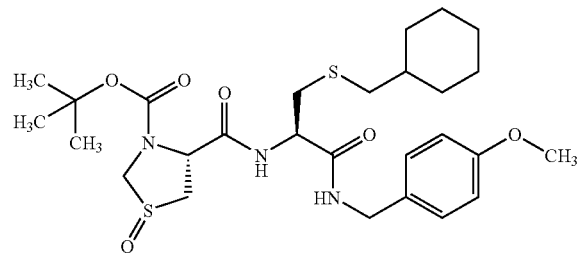

TLC: Rf 0.40 (chloroform:methanol=19:1); NMR (CD$_3$OD): δ 7.23-7.20 (2H,m), 6.87-6.82 (2H,m), 5.13-4.83 (1H,m), 4.70-4.20 (5H,m), 3.76 and 3.75 (3H,s), 3.60-3.30 (2H,m), 3.12-2.72 (2H,m), 2.43-2.38 (2H,m), 1.85-1.60 (5H, m), 1.50-1.09 (4H,m), 1.45 and 1.47 (9H,s), 1.00-0.83 (2H, m).

EXAMPLE 5 (4)

(2R)-N-(4-methoxybenzyl)-3-cyclohexylmethylsulfinyl-2-((4R)-3-t-butoxycarbonyl-1-oxothiazolidin-4-ylcarbonylamino)propanamide

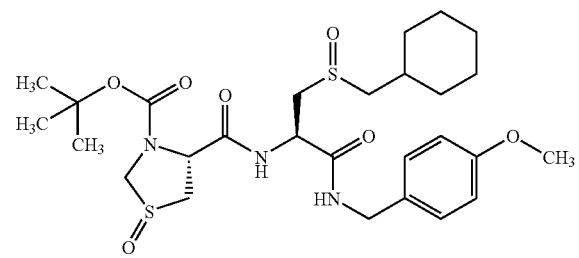

TLC: Rf 0.40 (chloroform:methanol=14:1); NMR (CD$_3$OD): δ 7.23-7.17 (2H,m), 6.88-6.81 (2H,m), 5.10-4.70 (1H,m), 4.65-4.50 (2H,m), 4.41-4.10 (3H,m), 3.75 (3H,s), 3.67-2.85 (4H,m), 2.85-2.57 (2H,m), 2.02-1.00 (11H,m), 1.48-1.45 (9H,m).

EXAMPLE 5 (5)

(2R)-N-(4-methoxybenzyl)-3-cyclohexylmethylthio-2-((2RS,4R)-3-t-butoxycarbonyl-2-methoxymethylthiazolidin-4-ylcarbonylamino)propanamide

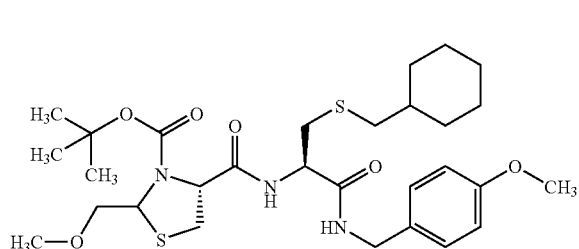

TLC: Rf 0.24 (ethyl acetate:hexane=2:3); NMR(CD$_3$OD): δ 7.26-7.20 (m,2H), 6.88-6.82 (m,2H), 5.26 (t,J=5 Hz,1H), 4.57-4.44 (m,2H), 4.38-4.23 (m,2H), 3.84 (dd,J=10, 5 Hz,1H), 3.76 (s,3H), 3.58 (dd,J=10, 3 Hz,1H), 3.47 (s,3H), 3.35-3.29 (m,2H), 2.97-2.63 (m,2H), 2.41 (bd,J=6 Hz,2H), 1.86-1.60 (m,5H), 1.51-1.07 (m,13H), 0.99-0.83 (m,2H).

EXAMPLE 5 (6)

(2R)-N-(4-methoxybenzyl)-3-cyclohexylmethylthio-2-((2RS,4R)-3-t-butoxycarbonyl-2-hydroxymethylthiazolidin-4-ylcarbonylamino)propanamide

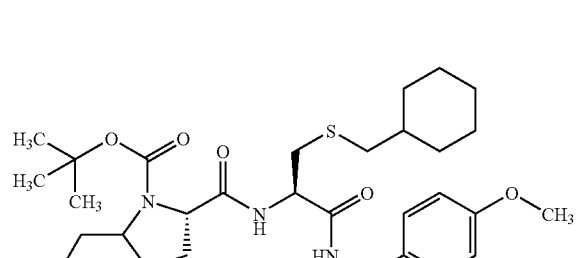

TLC: Rf 0.32 (ethyl acetate:methylene chloride=1:2); NMR(CDCl$_3$): δ 7.75-7.53 (b,1H), 7.25-7.15 (m,3H), 6.83-6.80 (m,2H), 5.30-5.10 (m,1H), 4.70-4.62 (m,1H), 4.62-4.46 (m,1H), 4.46-4.28 (m,2H), 4.20-3.98 (m,1H), 3.79 (s,3H), 3.67 (dd,J=11, 3 Hz,1H), 3.39 (dd,J=12, 6 Hz,1H), 3.33 (dd, J=12, 8 Hz,1H), 3.05-2.85 (b,2H), 2.49-2.32 (m,2H), 1.83-1.57 (m,6H), 1.50-1.30 (m,10H), 1.30-1.03 (m,3H), 1.00-0.81 (m,2H).

EXAMPLE 5 (7)

(2R)-N-(4-methoxybenzyl)-3-cyclohexylmethylthio-2-((2RS,4R)-3-t-butoxycarbonyl-2-(2-methylthioethyl)thiazolidin-4-ylcarbonylamino)propanamide

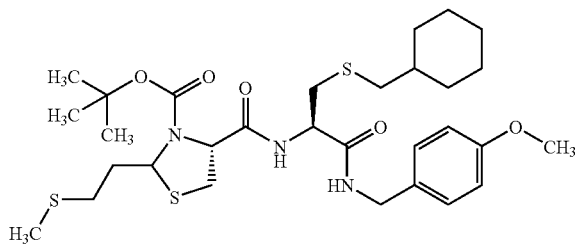

TLC: Rf 0.57 (ethyl acetate:hexane=1:1); NMR(CDCl$_3$): δ 7.35-7.13 (m,4H), 6.88-6.80 (m,2H), 5.28 (dd,J=9, 6 Hz,1H), 4.64 (t,J=8 Hz,1H)., 4.61-4.51 (m,1H), 4.42 (dd,J=15, 6 Hz,1H), 4.33 (dd,J=15, 6 Hz,1H), 3.78 (s,3H), 3.37-3.29 (m,2H), 3.25-3.10 (m,1H), 2.80 (dd,J=14, 6 Hz, 1H), 2.69-2.50 (m,2H), 2.48-2.20 (m,3H), 2.12 (s,3H), 2.03-1.87 (m,1H), 1.82-1.55 (m,5H), 1.51-1.33 (m,10H), 1.30-1.03 (m,3H), 1.00-0.78 (m,2H).

EXAMPLE 5 (8)

(2R)-N-(1-benzylpiperidin-4-yl)-3-cyclohexylmethylthio-2-((4R)-3-t-butoxycarbonyl-1,1-dioxothiazolidin-4-ylcarbonylamino)propanamide

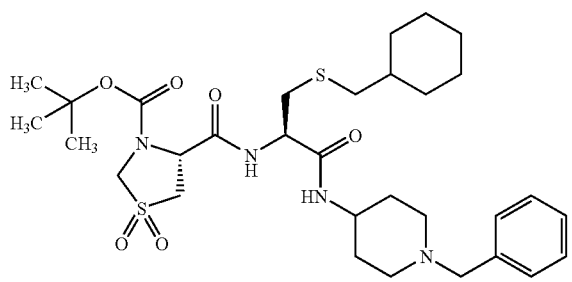

TLC: Rf 0.33 (chloroform:methanol=19:1); NMR (CD$_3$OD): δ 7.35-7.20 (m,5H), 5.07-4.86 (m,1H), 4.74 (dd, J=11.8, 1.6 Hz,1H), 4.43 (t,J=7.0 Hz,1H), 4.34 (d,J=11.8 Hz,1H), 3.74-3.56 (m,2H), 3.55 (s,2H); 3.50-3.35 (m,1H), 2.95-2.70 (m,4H), 2.45 (d,J=6.6 Hz,2H), 2.26-208 (m,2H), 1.92-0.83 (m,15H), 1.48 (m,9H).

EXAMPLE 5 (9)

(2R)-N-(1-benzylpiperidin-4-yl)-3-cyclohexylmethylthio-2-((4R)-3-t-butoxycarbonyl-1-oxothiazolidin-4-ylcarbonylamino)propanamide

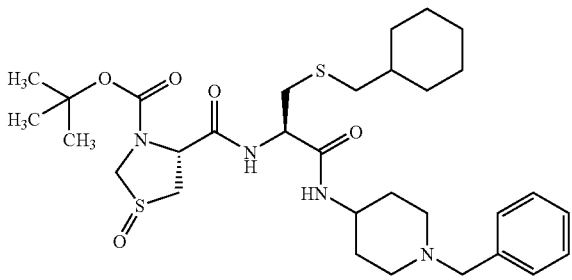

TLC: Rf 0.40 (chloroform:methanol=9:1); NMR (CD$_3$OD): δ 7.35-7.20 (m,5H), 5.16-4.90 (m,1H), 4.70-4.18 (m,3H), 3.74-3.40 (m,3H), 3.52 (s,2H), 3.20-2.70 (m,4H), 2.47-2.40 (m,2H), 2.23-2.04 (m,2H), 1.93-0.80 (m,15H), 1.50 (s,9H).

EXAMPLE 5 (10)

(2R)-N-(1-benzylpiperidin-4-yl)-3-cyclohexylmethylthio-((4S)-3-t-butoxycarbonyl-2-oxooxazolidin-4-ylcarbonylamino)propanamide

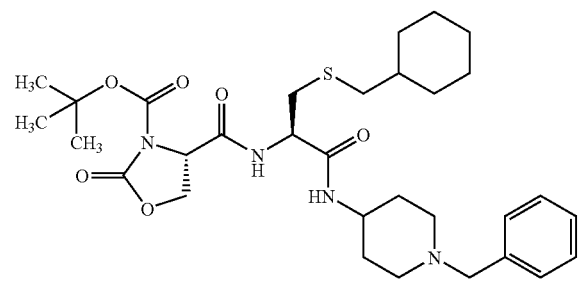

TLC: Rf 0.28 (methanol:chloroform=1:19); NMR (CDCl$_3$): δ 7.32-7.25 (m,5H), 7.19 (d,J=6.9 Hz,1H), 6.46 (d,J=8.1 Hz,1H), 4.70 (dd,J=8.4, 5.4 Hz,1H), 4.50-4.37 (m,3H), 3.86-3.72 (m,1H), 3.51 (s,2H), 2.95 (dd,J=14.1, 4.8 Hz,1H), 2.82-2.78 (m,2H), 2.69 (dd,J=13.8, 8.1 Hz,1H), 2.54 (dd,J=12.9, 6.9 Hz,1H), 2.47 (dd,J=12.9, 6.9 Hz,1H), 2.20-2.13 (m,2H), 1.96-1.38 (m,19H), 1.32-1.06 (m,3H), 1.02-0.84 (m,2H).

EXAMPLE 6~EXAMPLE 6 (2)

By the same procedures described in Reference Example 5→Reference Example 6, using compounds prepared in Example 5 (5)~Example 5 (7), the following compounds of the present invention were obtained.

EXAMPLE 6

(2R)-N-(4-methoxybenzyl)-3-cyclohexylmethylthio-2-((2RS,4R)-2-methoxymethylthiazolidin-4-ylcarbonylamino)propanamide

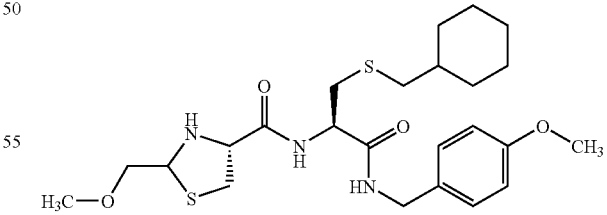

TLC: Rf 0.42 and 0.38 (methanol:methylene chloride=1:19); NMR(CD$_3$OD): δ 7.25-7.18 (m,2H), 6.89-6.83 (m,2H), 4.77 and 4.72 (t,J=6 Hz,1H), 4.54-4.45 (m,1H), 4.34 (d,J=15 Hz,1H), 4.30 (d,J=15 Hz,1H), 4.26-4.20 (m) and 4.02 (t,J=6 Hz)(1H), 3.76 (s,3H), 3.64-3.45 (m,2H), 3.40 and 3.39 (s,3H), 3.29-3.15 (m,1H), 3.09-3.00 (m,1H), 2.98-2.77 (m,2H), 2.43-2.37 (m,2H), 1.86-1.60 (m,5H), 1.50-1.34 (m,1H), 1.34-1.06 (m,3H), 0.99-0.84 (m,2H).

EXAMPLE 6 (1)

(2R)-N-(4-methoxybenzyl)-3-cyclohexylmethylthio-2-((2RS,4R)-2-hydroxymethylthiazolidin-4-ylcarbonylamino)propanamide

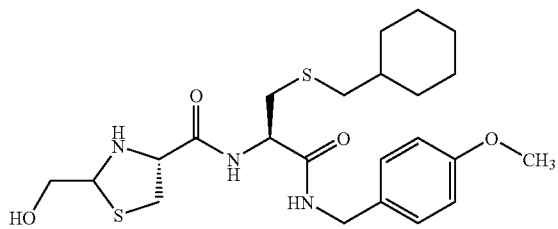

TLC: Rf 0.39 (methanol:methylene chloride=1:19); NMR (CD₃OD): δ 7.26-7.18 (m,2H), 6.90-6.83 (m,2H), 4.70 (t,J=5 Hz) and 4.63 (t,J=6 Hz)(1H), 4.53-4.46 (m,1H), 4.34 (d,J=15 Hz,1H), 4.29 (d,J=15 Hz,1H), 4.26-4.21 (m) and 4.03 (t,J=8 Hz)(1H), 3.76 (s,3H), 3.75-3.56 (m,2H), 3.28-3.14 (m,1H), 3.05 (dd,J=10, 7 Hz,1H), 2.97-2.88 (m,1H), 2.86-2.76 (m,1H), 2.39 and 2.41 (d,J=7 Hz,2H), 1.83-1.57 (m,5H), 1.50-1.30 (m,1H), 1.30-1.03 (m,3H), 1.00-0.81 (m,2H).

EXAMPLE 6 (2)

(2R)-N-(4-methoxybenzyl)-3-cyclohexylmethylthio-2-((2RS,4R)-2-(2-methylthioethyl)thiazolidin-4-ylcarbonylamino)propanamide

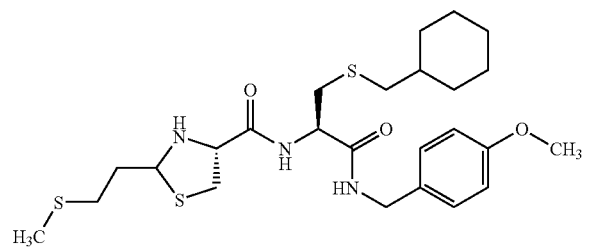

TLC: Rf 0.31 (methanol:methylene chloride=1:99); NMR (CD₃OD): δ 7.25-7.18 (m,2H), 6.90-6.83 (m,2H), 4.65 (t,J=6 Hz,1H), 4.58-4.45 (m,1H), 4.39-4.25 (m,2H), 4.30-4.25 (m) and 3.92 (t,J=8 Hz)(1H), 3.77 (s,3H), 3.41-2.78 (m,4H), 2.71-2.58 (m,2H), 2.39 and 2.41 (d,J=7 Hz,2H), 2.23-2.08 (m,1H), 2.10 (s,3H), 2.05-1.92 (m,1H), 1.86-1.58 (m,5H), 1.50-1.34 (m,1H), 1.34-1.06 (m,3H), 1.00-0.84 (m,2H).

EXAMPLE 7

(2R)-N-(4-phenoxybenzyl)-3-cyclohexylmethylthio-2-((4R)-3-hydroxymethylcarbonylthiazolidin-4-ylcarbonylamino)propanamide

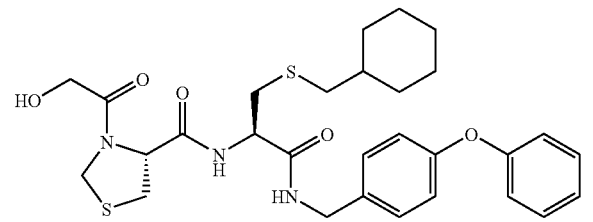

A compound prepared in Example 1 (5) (185 mg) was dissolved into methanol (10 ml). Thereto, an aqueous solution of 1N—NaOH (0.4 ml) was added. The mixture was stirred for 2.5 hours at room temperature. The reaction mixture was centurifized by addition of 1N HCl and concentrated. To the residue, water was added. The mixture was extracted with methylene chloride. The extract was washed by saturated solution of sodium chloride, dried over anhydrous sodium sulfate and concentrated to obtain the compound (172 mg) of the present invention having the following physical data.

TLC: Rf 0.41 (chloroform:methanol=19:1); NMR (CD₃OD): δ 7.37-7.29 (m,4H), 7.13-7.04 (m,1H), 7.00-6.89 (m,4H), 4.95-4.14 (m,8H), 3.43-3.30 (m,1H), 3.23-3.08 (m,1H), 2.97 (dd,J=13.8, 6.3 Hz,1H), 2.79 (dd,J=13.8, 7.8 Hz,1H), 2.44-2.40 (m,2H), 1.90-0.80 (m,11H).

EXAMPLE 7 (1)~Example 7 (2)

By the same procedure described in Example 7, using compounds prepared in Example 1 (2) and Example 1 (4), the following compounds of the present invention were obtained.

EXAMPLE 7(1)

(2R)-N-(4-methoxybenzyl)-3-cyclohexylmethylthio-2-((4R)-3-hydroxymethylcarbonylthiazolidin-4-ylcarbonylamino)propanamide

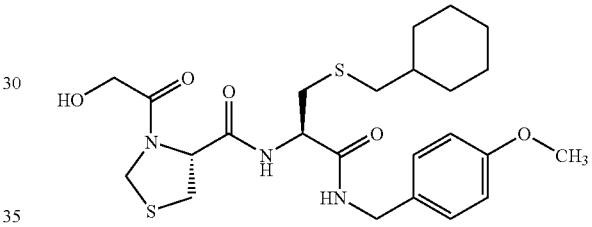

TLC: Rf 0.51 (chloroform:methanol=9:1); NMR (CD₃OD): δ 7.24-7.21 (2H,m), 6.86-6.83 (2H,m), 4.86-4.45 (4H,m), 4.40-4.10 (4H,m), 3.76 (3H,s), 3.45-2.92 (3H,m), 2.81-2.71 (1H,m), 2.42-2.39 (2H,m), 1.85-1.60 (5H,m), 1.50-1.08 (4H,m), 0.99-0.84 (2H,m).

EXAMPLE 7 (2)

(2R)-N-(1-benzylpiperidin-4-yl)-3-cyclohexylmethylthio-2-((4R)-3-hydroxymethylcarbonylthiazolidin-4-ylcarbonylamino)propanamide

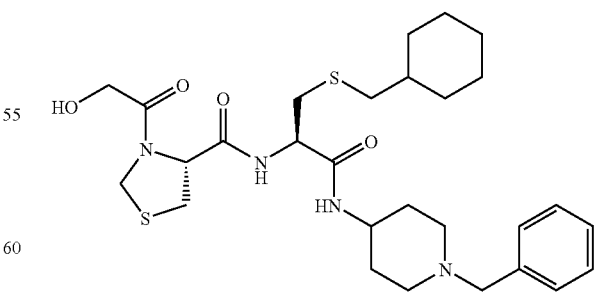

TLC: Rf 0.48 (chloroform:methanol=9:1); NMR (CD₃OD): δ 7.35-7.20 (m,5H), 4.90-4.00 (m,6H), 3.75-3.53 (m,1H), 3.53 (s,2H), 3.45-2.66 (m,6H), 2.43 (d,2H,J=6.8 Hz), 2.20-2.05 (m,2H), 1.90-0.80 (m,15H).

EXAMPLE 8~EXAMPLE 8 (1)

By the same procedure described in Example 2, using compounds prepared in Example 3 and 3 (7), the following compounds of the present invention were obtained.

EXAMPLE 8

(2R)-N-(4-phenoxybenzyl)-3-cyclohexylmethylthio-2-((4R)-3-(morpholin-4-ylcarbonylmethyl)thiazolidin-4-ylcarbonylamino)propanamide

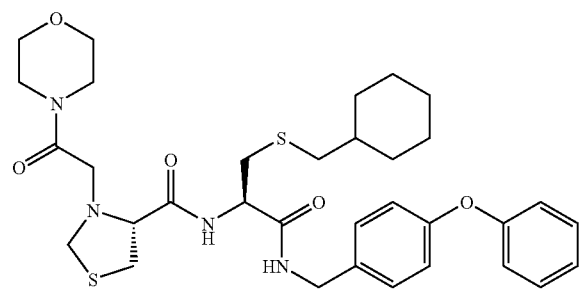

TLC: Rf 0.41 (chloroform:methanol=19:1); NMR (CD$_3$OD): δ 7.38-7.23 (m,4H), 7.12-7.04 (m,1H), 6.99-6.87 (m,4H), 4.55 (dd,J=7.6, 5.3 Hz,1H), 4.43 (d,J=15.0 Hz,1H), 4.35 (d,J=15.0 Hz,1H), 4.25 (d,J=10.5 Hz,1H), 4.06 (d,J=10.5 Hz,1H), 4.05-4.00 (m,1H), 3.72-3.42 (m,10H), 3.39-3.31 (m,1H), 3.20 (dd,J=11.0, 8.0 Hz,1H), 3.00 (dd, J=13.8, 5.3 Hz,1H), 2.90 (dd,J=13.8, 7.6 Hz,1H), 2.40 (d,J=6.6 Hz,2H), 1.90-0.80 (m,1H).

EXAMPLE 8 (1)

(2R)-N-(1-benzylpiperidin-4-yl)-3-cyclohexylmethylthio-2-((4R)-3-(morpholin-4-ylcarbonylmethyl)thiazolidin-4-ylcarbonylamino)propanamide

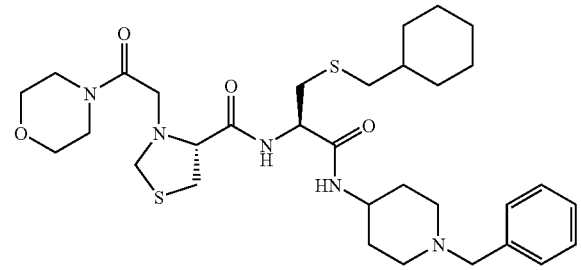

TLC: Rf 0.48 (chloroform:methanol=9:1); NMR (CD$_3$OD): δ 7.35-7.20 (m,5H), 4.46 (dd,J=7.5, 5.0 Hz,1H), 4.25 (d, J=10.0 Hz,1H), 4.07 (d,J=10.0 Hz,1H), 4.06-4.00 (m,1H), 3.76-3.48 (m,11H), 3.51 (s,2H), 3.37 (dd,J=11.0, 3.4 Hz,1H), 3.18 (dd,J=11.0, 8.0 Hz,1H), 2.99-2.77 (m,4H), 2.42 (d,J=7.0 Hz,2H), 2.20-2.04 (m,2H), 1.90-0.80 (m,15H).

EXAMPLE 9

(2R)-N-(4-phenoxybenzyl)-3-cyclohexylmethylthio-2-((4R)-3-(2-(tetrahydropyran-2-yloxy)ethyl)thiazolidin-4-ylcarbonylamino)propanamide A compound prepared in Example 3 (8) (165 mg) and dihydropyran (68 mg) were dissolved into anhydrous tetrahydrofuran (6 ml). Thereto, p-toluene sulfonic acid (63 mg) and pyridium p-toluene sulfonate (amount of catalyst) were added. The mixture was stirred for 3.5 hours at room temperature. To the reaction mixture, triethylamine (a few drops) was added. The mixture was concentrated. The residue was purified with column chromatography on silica gel (chloroform:methanol=50:1) to obtain the compound (70 mg) of the present invention having the following physical data.

TLC: Rf 0.39 (chloroform:methanol=19:1); NMR (CD$_3$OD): δ 7.38-7.25 (m,4H), 7.14-7.05 (m,1H), 6.98-6.90 (m,4H), 5.16-5.09 (m,1H), 4.52-4.45 (m,1H), 4.37 (s,2H), 4.26-4.08 (m,3H), 4.00-3.50 (m,4H), 3.46-3.35 (m,1H), 3.14-2.70 (m,5H), 2.40 (d,J=7.0 Hz,2H), 2.00-0.80 (m,17H).

EXAMPLE 10

(2R)-N-(4-phenoxybenzyl)-3-cyclohexylmethylthio-2-((4R)-3-(2-methoxyethyl)thiazolidin-4-ylcarbonylamino)propanamide.hydrochloride A compound prepared in Example 3 (10) (45 mg) was dissolved into ethyl acetate (2 ml). Thereto, a solution of 4N HCl-ethyl acetate (0.05 ml) was added. The mixture was stirred at room temperature. The solvent was distilled off. The reside was washed by a mixture solvent of ethyl acetate and hexane to obtain the compound (30 mg) having the following physical data.

TLC: Rf 0.53 (chloroform:methanol=19:1); NMR (CD$_3$OD): δ 7.38-7.25 (m,4H), 7.14-7.05 (m,1H), 6.97-6.88 (m,4H), 4.70 (d,J=10.2 Hz,1H), 4.57-4.49 (m,2H), 4.39-4.34 (m,3H), 3.72-3.25 (m,6H), 3.35 (s,3H), 2.95 (dd,J=13.5, 6.3 Hz,1H), 2.80 (dd,J=13.5, 8.0 Hz,1H), 2.45 (d, J=6.6 Hz,2H), 1.90-0.80 (m, 11H).

EXAMPLE 10 (1)~EXAMPLE 10 (2)

By the same procedure described in Example 10 using compounds prepared in Example 3 (1) and Example 8, the following compounds of the present invention were obtained.

EXAMPLE 10 (1)

(2R)-N-(4-nitrobenzyl)-3-cyclohexylmethylthio-2-((4R)-3-(3-methylbutyl)thiazolidin-4-ylcarbonylamino)propanamide.hydrochloride

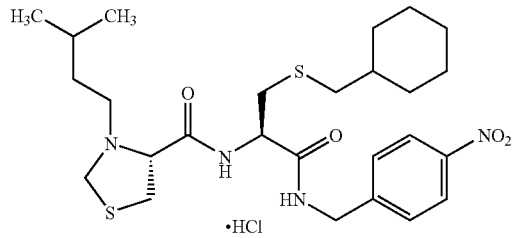

TLC: Rf 0.60 (ethyl acetate:hexane=1:1); NMR(CD₃OD): δ 8.24-8.15 (2H,m), 7.59-7.51 (2H,m), 4.74 (1H,d,J=10.2 Hz), 4.62 (1H,dd,J=8.8, 5.8 Hz), 4.51 (2H,s), 4.47-4.43 (1H, m) 4.37 (1H,d,J=10.2 Hz), 3.67 (1H,dd,J=12.0, 8.0 Hz), 3.49-3.22 (3H,m), 3.00 (1H,dd,J=13.6, 5.6 Hz), 2.81 (1H, dd,J=13.6, 8.8 Hz), 2.48 (2H,d,J=7.0 Hz), 1.90-0.84 (20H, m).

EXAMPLE 10(2)

(2R)-N-(4-phenoxybenzyl)-3-cyclohexylmethylthio-2-((4R)-3-(morpholin-4-ylcarbonylmethyl)thiazolidin-4-ylcarbonylamino)propanamide.hydrochloride

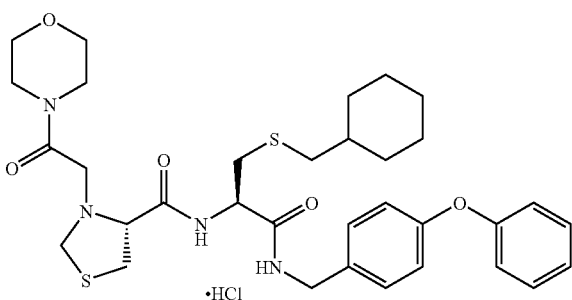

TLC: Rf 0.37 (methylene chloride:methanol=19:1); NMR (CD₃OD): δ 7.36-7.28 (m,4H), 7.12-7.06 (m,1H), 6.97-6.89 (m,4H), 4.60-4.52 (m,2H), 4.43-4.31 (m,4H), 4.20 (d,J=16.5 Hz,1H), 4.16 (d,J=16.5 Hz,1H), 3.73-3.32 (m,10H), 2.96 (dd, J=13.8, 6.3 Hz,1H), 2.89 (dd,J=13.8, 7.8 Hz,1H), 2.43 (d,J=6.6 Hz,2H), 1.83-1.59 (m,5H), 1.50-1.36 (m,1H), 1.30-1.08 (m,3H), 0.98-0.86 (m,2H).

EXAMPLE 11~EXAMPLE 11 (4)

By the same procedures described in Example 1→Example 10, using (2R)-N-(1-benzylpiperidin-4-yl)-3-cyclohexylmethylthio-2-((4R)-thiazolidin-4-ylcarbonylamino)propanamide prepared by the same procedures described in Reference Example 1→Reference Example 2→Reference Example 3→Reference Example 4→Reference Example 5→Reference Example 6, the following compounds of the present invention were obtained.

EXAMPLE 11

(2R)-N-(1-benzylpiperidin-4-yl)-3-cyclohexylmethylthio-2-((4R)-3-(2-methoxyethoxycarbonyl)thiazolidin-4-ylcarbonylamino)propanamide.hydrochloride

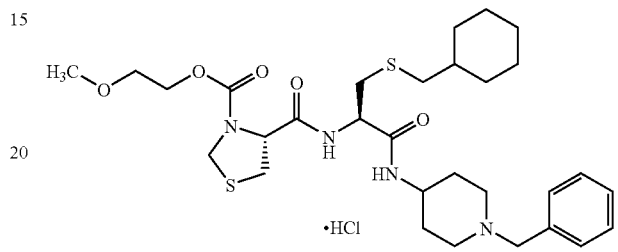

TLC: Rf 0.58 (methanol:chloroform 1:9); NMR(CD₃OD): δ 7.38-7.24 (m,5H), 4.71-4.42 (m,4H), 4.27 (br. s,2H), 3.74-3.52 (m,5H), 3.38 (dd,J=12.3, 7.5 Hz,1H), 3.36 (s,3H), 3.17 (dd,J=12.3, 4.8 Hz,1H), 2.96-2.92 (m,3H), 2.77 (dd,J=13.5, 8.1 Hz,1H), 2.44 (d,J=6.9 Hz,2H), 2.30-2.23 (m,2H), 1.92-1.78 (m,4H), 1.76-1.36 (m,6H), 1.34-1.08 (m,3H), 1.02-0.86 (m,2H).

EXAMPLE 11 (1)

(2R)-N-(1-benzylpiperidin-4-yl)-3-cyclohexylmethylthio-2-((4R)-3-chloromethoxycarbonylthiazolidin-4-ylcarbonylamino)propanamide.hydrochloride

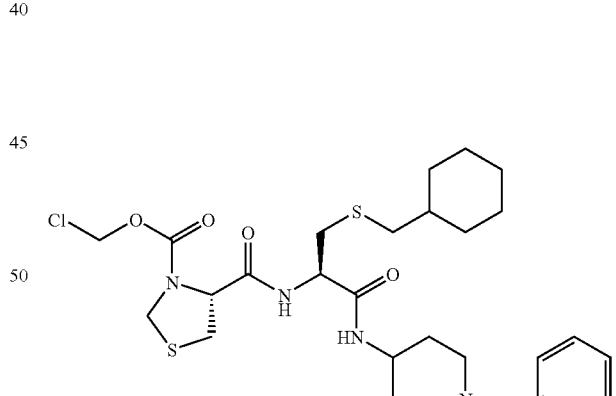

TLC: Rf 0.53 (methanol:chloroform=1:9); NMR (CD₃OD): δ 7.41-7.23 (m,5H), 5.89-5.79 (m,2H), 4.71-4.66 (m,2H), 4.59-4.51 (m,1H), 4.44 (t,J=6.6 Hz,1H), 3.77-3.52 (m,3H), 3.44-3.37 (m,1H), 3.17 (dd,J=12.0, 4.5 Hz,₁H), 3.01-2.68 (m,4H), 2.44 (d,J=6.3 Hz,2H), 2.36-2.12 (m,2H), 1.94-1.08 (m,12H), 1.01-0.85 (m,3H).

EXAMPLE 11 (2)

(2R)-N-(1-benzylpiperidin-4-yl)-3-cyclohexylmethylthio-2-((4R)-3-(3,3-dimethylbutyryl)thiazolidin-4-ylcarbonylamino)propanamide.hydrochloride

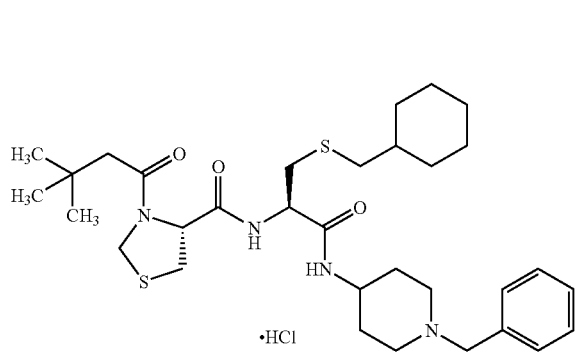

TLC: Rf 0.52 (chloroform:methanol=9:1); NMR(DMSO-$d_6$,100° C.): δ 11.01-10.73 (br,1H), 8.03-7.73 (br,2H), 7.62-7.60 (m,2H), 7.44-7.43 (m,3H), 4.88 (dd,J=7.5, 4.0 Hz,1H), 4.83 (d,J=9.5 Hz,1H), 4.57-4.35 (br,2H), 4.32-4.15 (br,2H), 4.02-3.71 (br,1H), 3.36-3.24 (br,3H), 3.14-2.92 (m,3H), 2.87-2.79 (br,2H), 2.43 (d,J=7.0 Hz,2H), 2.33-1.86 (br,6H), 1.77-1.59 (m,5H), 1.47-1.38 (m,1H), 1.26-0.89 (m,14H).

EXAMPLE 11 (3)

(2R)-N-(1-benzylpiperidin-4-yl)-3-cyclohexylmethylthio-2-((4R)-3-cyclopentylcarbonylthiazolidin-4-ylcarbonylamino)propanamide.hydrochloride

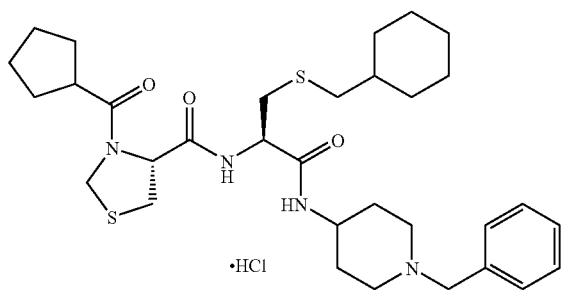

TLC: Rf 0.57 (chloroform:methanol=9:1); NMR (CD$_3$OD): δ 7.53-7.47 (m,5H), 4.90-4.65 (m,2H), 4.60-4.37 (m,2H), 4.31 (s,2H), 4.06-3.83 (m,1H), 3.60-3.00 (m,5H), 3.00-2.80 (m,2H), 2.44 (d,J=7.0 Hz,2H), 2.20-2.00 (m,2H), 2.00-1.50 (m,16H), 1.50-1.40 (m,1H), 1.38-1.12 (m,4H), 1.00-0.90 (m,2H).

EXAMPLE 11 (4)

(2R)-N-(1-benzylpiperidin-4-yl)-3-cyclohexylmethylthio-2-((4R)-3-benzoylthiazolidin-4-ylcarbonylamino)propanamide.hydrochloride

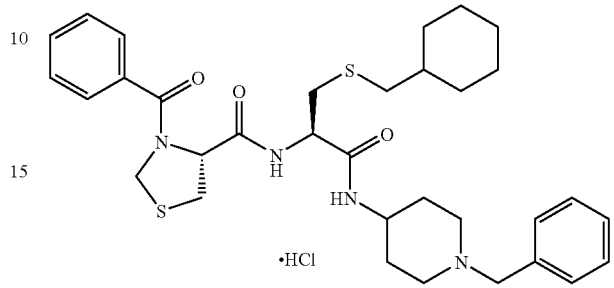

TLC: Rf 0.57 (chloroform:methanol=9:1); NMR (CD$_3$OD): δ 7.70-7.30 (m,10H), 5.00-4.60 (m,3H), 4.40 (t,J=6.8 Hz,1H), 4.35-4.15 (m,2H), 4.14-3.85 (m,1H), 3.60-2.70 (m,8H), 2.44 (d,J=7.0 Hz,2H), 2.20-1.90 (m,2H), 1.90-1.73 (m,3H), 1.73-1.60 (m,3H), 1.50-1.40 (m,1H), 1.37-1.10 (m,4H), 1.00-0.88 (m,2H).

EXAMPLE 12

(2R)-N-(1-benzylpiperidin-4-yl)-3-cyclohexylmethylthio-((4R)-3-(3,3-dimethyl-1,2-dioxobutyl)thiazolidin-4-ylcarbonylamino)propanamide.hydrochloride

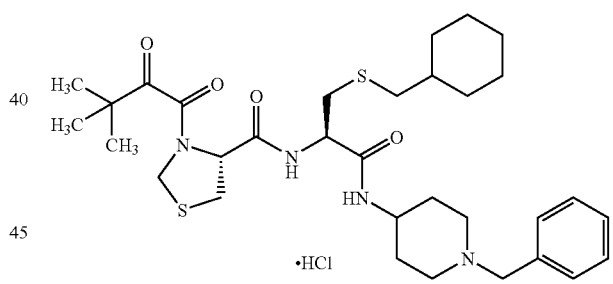

A solution of a compound prepared in Example 1 (13) (400 mg) in tetrahydrofuran (5 ml) was cooled to −78° C. Thereto, t-butyl magnesium chloride (1.0 ml, 2.0M in tetrahydrofuran) was added. The mixture was stirred for 2 hours at −78° C., and then for 30 minutes at room temperature. The reaction mixture was quenched by saturated solution of ammonium chloride and extracted with ethyl acetate. The extract was washed by saturated solution of sodium chloride, dried over anhydrous sodium sulfate and concentrated. The residue was purified with column chromatography on silica gel (ethyl acetate:hexane=2:1→3:1). The purified product was dissolved into ethyl acetate. Thereto, a solution of 4N HCl-ethyl acetate was added. The mixture was concentrated. The residue was washed by diethyl ether to obtain the compound (184.9 mg) of the present invention having the following physical data.

TLC: Rf 0.24 (ethyl acetate:hexane=3:1); NMR(CD$_3$OD): δ 7.58-7.43 (m,5H), 4.92-4.76 (m,1H), 4.60-4.51 (m,2H), 4.44-4.35 (m,1H), 4.31 (s,2H), 4.02-3.84 (m,1H), 3.60-3.00

(m,6H), 2.96-2.70 (m,2H), 2.48-2.41 (m,2H), 2.22-2.02 (m,2H), 1.90-1.61 (m,7H), 1.55-1.35 (m,1H), 1.35-1.01 (m,12H), 1.04-0.87 (m,2H).

EXAMPLE 13~EXAMPLE 13 (2)

By the same procedures described in Example 5→Example 10, the following compounds of the present invention were obtained.

EXAMPLE 13

(2R)-N-(1-benzylpiperidin-4-yl)-3-cyclohexylmethylthio-((4R)-2,2,5,5-tetramethylthiazolidin-4-ylcarbonylamino)propanamide.2hydrochloride

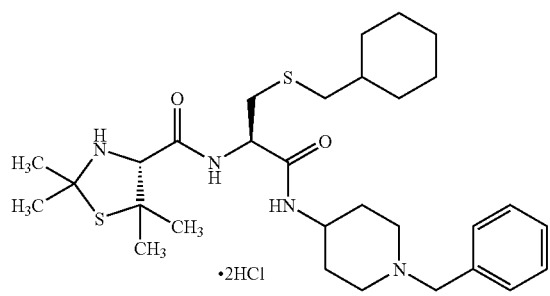

TLC: Rf 0.38 (methylene chloride:methanol=93:7); NMR (CD$_3$OD): δ 7.60-7.45 (m,5H), 4.66-4.49 (m,2H), 4.41 and 4.31 (s,2H), 4.12-4.05 and 3.97-3.85 (m,1H), 3.56-3.46 and 3.42-3.23 (m,2H), 3.42-3.23 and 3.17-3.05 (m,2H), 3.02-2.79 (m,2H), 2.53 and 2.48 (d,J=7 Hz,2H), 2.18-2.02 (m, 2H), 1.95-1.60 (m,16H), 1.53-1.37 (m,4H), 1.35-1.09 (m,3H), 1.05-0.88 (m,2H).

EXAMPLE 13 (1)

(2R)-N-(1-benzylpiperidin-4-yl)-3-cyclohexylmethylthio-((2S)-1-t-butoxycarbonyl-4-oxopyrrolidin-2-ylcarbonylamino)propanamide.hydrochloride

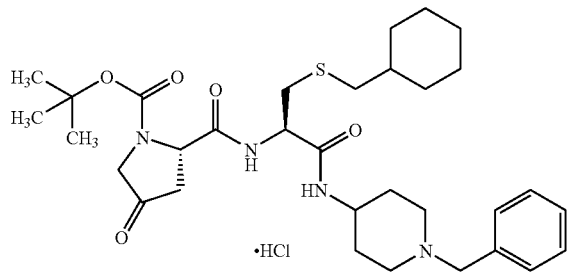

TLC: Rf 0.34 (methanol:chloroform=1:19); NMR (CD$_3$OD): δ 7.55-7.45 (m,5H), 4.72 (dd,J=9.9, 6.0 Hz,1H), 4.39-4.28 (m,3H), 4.02-3.74 (m,3H), 3.58-2.66 (m,7H), 2.55-2.38 (m,3H), 2.18-0.86 (m,24H).

EXAMPLE 13 (2)

(2R)-N-(1-benzylpiperidin-4-yl)-3-cyclohexylmethylthio-((2S, 4R)-1-t-butoxycarbonyl-4-hydroxypyrrolidin-2-ylcarbonylamino)propanamide.hydrochloride

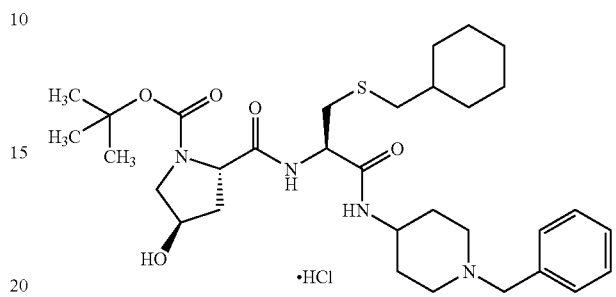

TLC: Rf 0.34 (methanol:chloroform=1:9); NMR (CD$_3$OD): δ 7.56-7.46 (m,5H), 4.43-4.25 (m,5H), 3.99-3.84 (m,1H), 3.62-3.44 (m,4H), 3.24-3.04 (m,2H), 2.91-2.70 (m,2H), 2.47-2.41 (m,2H), 2.28-1.08 (m,22H), 1.04-0.86 (m,2H).

EXAMPLE 14~EXAMPLE 4 (2)

By the same procedures described in Reference Example 4→Example 10 using (2R)-N-(1-benzylpiperidin-4-yl)-2-amino-3-cyclohexylmethylthiopropanamide.2hydrochloride prepared by the same procedures described in Reference Example 1→Reference Example 2→Reference Example 3, the following compounds of the present invention were obtained.

EXAMPLE 14

(2R)-N-(1-benzylpiperidin-4-yl)-3-cyclohexylmethylthio-2-((4R)-3-isopropylsulfonylthiazolidin-4-ylcarbonylamino)propanamide.hydrochloride

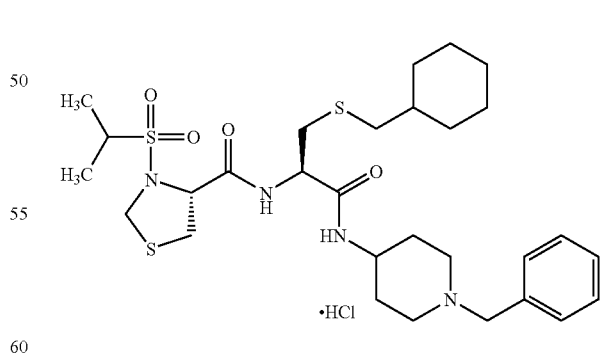

TLC: Rf 0.51 (methanol:chloroform=1:9); NMR (DMSO-d$_6$): δ 10.64-10.46 (br, 1H), 8.33-8.22 (m, 2H), 7.61-7.53 (br, 2H), 7.45-7.43 (m, 3H), 4.88-4.75 (m, 2H), 4.42-4.21 (m, 4H), 3.98-3.75 (br, 1H), 3.50-2.92 (m, 7H), 2.78-2.60 (m, 2H), 2.39 (d, J=6.6 Hz, 2H), 2.05-1.53 (m, 9H), 1.47-1.01 (m, 10H), 0.99-0.81 (m, 2H).

EXAMPLE 14 (1)

(2R)-N-(1-benzylpiperidin-4-yl)-3-cyclohexylmethylthio-2-((4R)-3-cyclopentylsulfonylthiazolidin-4-ylcarbonylamino)propanamide.hydrochloride

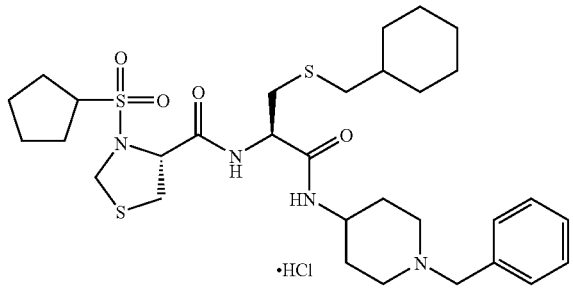

TLC: Rf 0.46 (methanol:chloroform=1:9); NMR (DMSO-$d_6$): δ 10.57-10.41 (br, 1H), 8.35-8.14 (m, 2H), 7.61-7.53 (br, 2H), 7.45-7.43 (m, 3H), 4.89-4.76 (m, 2H), 4.44-4.21 (m, 4H), 3.97-3.68 (m, 2H), 3.39-2.92 (m, 6H), 2.78-2.61 (m, 2H), 2.39 (d, J=6.9 Hz, 2H), 1.97-1.53 (m, 17H), 1.41-1.00 (m, 4H), 0.92-0.81 (m, 2H).

EXAMPLE 14 (2)

(2R)-N-(1-benzylpiperidin-4-yl)-3-cyclohexylmethylthio-2-((4R)-3-isobutylsulfonylthiazolidin-4-ylcarbonylamino)propanamide.hydrochloride

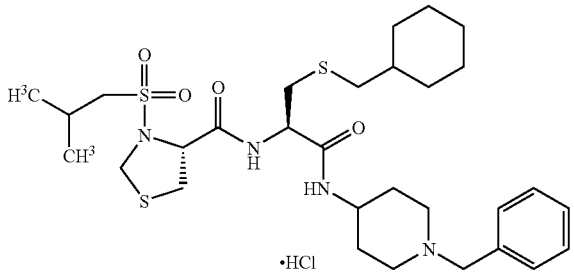

TLC: Rf 0.56 (methanol:chloroform=1:9); NMR (DMSO-$d_6$): δ 10.45-10.31 (br, 1H), 8.30-8.08 (m, 2H), 7.57-7.44 (m, 5H), 4.83-4.72 (m, 2H), 4.44-4.20 (m, 4H), 3.98-3.65 (m, 1H), 3.41-2.94 (m, 8H), 2.86-2.64 (m, 2H), 2.38 (d, J=6.9 Hz, 2H), 2.20-2.08 (m, 1H), 2.00-1.56 (m, 9H), 1.41-1.28 (m, 1H), 1.23-1.00 (m, 9H), 0.91-0.80 (m, 2H).

EXAMPLE 15

(2R)-N-(1-benzylpiperidin-4-yl)-3-cyclohexylmethylthio-2-((4R)-3-allyloxycarbonylthiazolidin-4-ylcarbonylamino)propanamide.hydrochloride

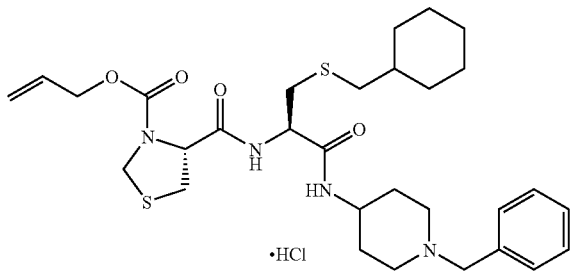

By the same procedures described in Example 10 using a compound prepared in Example 1 (10), the compound having the following physical data.

TLC: Rf 0.39 (methanol:methylene chloride=1:19); NMR (CD$_3$OD): δ 7.58-7.45 (m, 5H), 6.07-5.87 (m, 1H), 5.41-5.14 (m, 2H), 4.74-4.39 (m, 6H), 4.31 (s, 2H), 4.10-3.84 (m,1 H), 3.55-3.33 (m, 3H), 3.22-3.05 (m, 3H), 3.02-2.70 (m, 2H), 2.50-2.40 (m, 2H), 2.20-2.00 (m, 2H), 1.90-1.60 (m, 7H), 1.53-1.35 (m, 1H), 1.35-1.08 (m, 3H), 1.05-0.85 (m, 2H).

FORMULATION EXAMPLE

FORMULATION EXAMPLE 1

The following compounds were admixed in conventional method and punched out to obtain 100 tablets each containing 50 mg of active ingredient.

| | |
|---|---|
| (2R)-N-(1-benzylpiperidin-4-yl)-3-cyclohexylmethylthio-2-((4R)-3-(3,3-dimethylbutyryl)thiazolidin-4-ylcarbonylamino)propanamide | 5.0 g |
| Carboxymethylcellulose calcium (disintegrating agent) | 0.2 g |
| Magnesium stearate (lubricating agent) | 0.1 g |
| Micro crystalline cellulose | 4.7 g |

FORMULATION EXAMPLE 2

The following components were admixed in a conventional method, and the solution was sterilized in a conventional method, placed 5 ml portions into ampoules and freeze-dried in a conventional method to obtain 100 ampoules each containing 20 mg of active ingredient.

| | |
|---|---|
| (2R)-N-(1-benzylpiperidin-4-yl)-3-cyclohexylmethylthio-2-((4R)-3-(3,3-dimethylbutyryl)thiazolidin-4-ylcarbonylamino)propanamide | 2.00 g |
| Mannitol | 20 g |
| Distilled water | 500 ml |

The invention claimed is:

1. An amino acid compound of the formula (I)

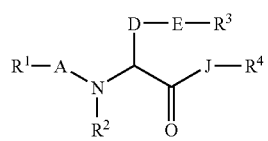

(wherein,

R$^1$ is thiazolidinyl, which is substituted with (a) four C1-4 alkyl or (b) one substituent selected from the following (i)-(xii) essentially, and which may be substituted with 1 to 3 substituent(s) selected from the group consisting of (i)-(xxiii):

(i) oxo, (ii) C5-8 alkyl, (iii) —COO—R$^5$ (in which, R$^5$ is hydrogen, C5-8 alkyl, C2-8 alkenyl, or C1-4 alkyl substituted with 1 to 3 of halogen or C1-4 alkoxy), (iv) —(C1-4 alkylene)-COOR$^6$ (in which, R$^6$ is hydrogen, C1-8 alkyl, C2-8 alkenyl or C1-4 alkyl substituted with 1 to 3 of halogen), (v) —CO—R$^7$ (in which, R$^7$ is C5-8 alkyl, C2-4 alkenyl, carbocyclic ring, heterocyclic ring or C1-8 alkyl substituted with one substituent selected from the following (1)-(8):
  (1) carbocyclic ring,
  (2) heterocyclic ring,
  (3) hydroxy,
  (4) C1-4 alkoxy,
  (5) —OCO—(C1-4 alkyl),
  (6) —O—(C1-4 alkylene)-O—(C1-4 alkyl),
  (7) NR$^8$R$^9$ (in which, R$^8$ and R$^9$ each, independently, is hydrogen or C1-4 alkyl),
  (8) halogen),
(vi) —(C1-4 alkylene)-CO—R$^{10}$ (in which, R$^{10}$ is C1-8 alkyl, C2-4 alkenyl, carbocyclic ring, heterocyclic ring or C1-8 alkyl substituted with one substituent selected from the following (1)-(8):
  (1) carbocyclic ring,
  (2) heterocyclic ring,
  (3) hydroxy,
  (4) C1-4 alkoxy,
  (5) —OCO—(C1-4 alkyl),
  (6) —O—(C1-4 alkylene)-O—(C1-4 alkyl),
  (7) NR$^{11}$R$^{12}$ (in which, R$^{11}$ and R$^{12}$ each, independently, is hydrogen or C1-4 alkyl),
  (8) halogen),
(vii) —CO—CO—R$^{13}$,
(viii) —CO—(C1-4 alkylene)-CO—R$^{14}$,
(ix) —SO$_2$—R$^{15}$ (in which, R$^{13}$, R$^{14}$ and R$^{15}$ each, independently, is C1-8 alkyl, C2-4 alkenyl, carbocyclic ring, heterocyclic ring, hydroxy, C1-4 alkoxy or C1-8 alkyl substituted with one substituent selected from the following (1)-(8):
  (1) carbocyclic ring,
  (2) heterocyclic ring,
  (3) hydroxy,
  (4) C1-4 alkoxy,
  (5) —OCO—(C1-4 alkyl),
  (6) —O—(C1-4 alkylene)-O—(C1-4 alkyl),
  (7) NR$^{16}$R$^{17}$ (in which, R$^{16}$ and R$^{17}$ each, independently, is hydrogen or C1-4 alkyl),
  (8) halogen),
(x) —CONR$^{18}$R$^{19}$ (in which, R$^{18}$ is hydrogen or C1-4 alkyl which may be substituted with one phenyl, R$^{19}$ is C1-8 alkyl or C2-4 alkenyl),
(xi) C1-8 alkyl substituted with 1 to 2 of substituent(s) selected from the group consisting of the following (1)-(7):
  (1) hydroxy,
  (2) C1-4 alkoxy,
  (3) —O—(C1-4 alkylene)-O—(C1-4 alkyl),
  (4) tetrahydropyran-2-yloxy,
  (5) —SR$^{20}$ (in which, R$^{20}$ is hydrogen or C1-4 alkyl),
  (6) halogen,
  (7) NR$^{21}$R$^{22}$ (in which, R$^{21}$ and R$^{22}$ each, independently, is hydrogen or C1-4 alkyl),
(xii) hydroxy,
(xiii) C1-4 alkyl,
(xiv) C1-4 alkoxy,
(xv) phenyl,
(xvi) phenoxy,
(xvii) benzyloxy,
(xviii) —SR$^{23}$ (in which, R$^{23}$ is hydrogen or C1-4 alkyl),
(xix) C2-5 acyl,
(xx) halogen,
(xxi) C1-4 alkoxycarbonyl,
(xxii) nitro,
(xxiii) —NR$^{24}$R$^{25}$ (in which, R$^{24}$ and R$^{25}$ each, independently, is hydrogen, C1-4 alkyl or C1-4 alkoxycarbonyl, or R$^{24}$ and R$^{25}$ taken together with nitrogen atom to which is attached represents 5 to 7-membered saturated heterocyclic ring necessary containing one nitrogen atom and optionally further containing one nitrogen atom or one oxygen atom), A is —CO—,
R$^2$ is hydrogen or C1-4 alkyl which may be substituted with one phenyl,
D is C1-4 alkylene,
E is,
R$^3$ is C1-4 alkyl substituted with C3-10 cycloalkyl, which may be substituted with 1 to 3 substituent(s) selected from the group consisting of the following (i)-(xi):
  (i) C1-4 alkyl,
  (ii) C1-4 alkoxy,
  (iii) phenyl,
  (iv) phenoxy,
  (v) benzyloxy,
  (vi) —SR$^{31}$ (in which, R$^{31}$ is hydrogen or C1-4 alkyl),
  (vii) C2-5 acyl,
  (viii) halogen,
  (ix) C1-4 alkoxycarbonyl,
  (x) nitro,
  (xi) —NR$^{32}$R$^{33}$ (in which, R$^{32}$ and R$^{33}$ each, independently, is hydrogen, C1-4 alkyl or C1-4 alkoxycarbonyl, or R$^{32}$ and R$^{33}$ taken together with nitrogen atom to which is attached represents 5 to 7-membered saturated heterocyclic ring necessary containing one nitrogen atom and optionally further containing one nitrogen atom or one oxygen atom), J is
1) —O—,
2) —NR$^{34}$— (in which, R$^{34}$ is hydrogen, C1-4 alkyl which may be substituted with one phenyl, NR$^{35}$R$^{36}$ (in which, R$^{35}$ and R$^{36}$ each, independently, is hydrogen or C1-4 alkyl), hydroxy, C1-4 alkoxy, —(C1-4 alkylene)-OH, —(C1-4 alkylene)-O—(C1-4 alkyl) or —(C1-4 alkylene)-O—(C2-5 acyl)),
3) —NR$^{37}$—NR$^{38}$— (in which, R$^{37}$ and R$^{38}$ each, independently, is hydrogen or C1-4 alkyl which may be substituted with one phenyl),
4) —NR$^{39}$—(C1-4 alkylene)-NR$^{40}$— (in which, R$^{39}$ and R$^{40}$ each, independently, is hydrogen or C1-4 alkyl which may be substituted with one phenyl),
5) —NR$^{41}$—(C1-4 alkylene)-O— (in which, R$^{41}$ is hydrogen or C1-4 alkyl which may be substituted with one phenyl) or
6) —NR$^{42}$—(C1-4 alkylene)-S— (in which, R$^{42}$ is hydrogen or C1-4 alkyl which may be substituted with one phenyl), R$^4$ is R$^{4-1}$ or R$^{4-2}$,
R$^{4-1}$ is C1-8 alkyl substituted with which may be substituted with 1 to 3 substituent(s) selected from the group consisting of the following (i)-(x):
  (i) C1-4 alkyl,
  (ii) C1-4 alkoxy,
  (iii) —SR$^{46}$ (in which, R$^{46}$ is hydrogen or C1-4 alkyl),
  (iv) C2-5 acyl,
  (v) halogen,
  (vi) C1-4 alkoxycarbonyl,
  (vii) nitro,
  (viii) —NR$^{47}$R$^{48}$ (in which, R$^{47}$ and R$^{48}$ each, independently, is hydrogen, C1-4 alkyl or C1-4 alkoxycarbonyl),
  (ix) hydroxy, (x) —(C1-4 alkylene)-O—(C1-4 alkyl),
$R^{4-2}$ is -L-M,
-L- is (C1-4 alkylene)-phenyl,
M is
1) carbocyclic ring,
2) heterocyclic ring,
3) C1-4 alkyl substituted with 1 to 2 of substituent(s) selected from the group consisting of the following (i)-(ii):
   (i) carbocyclic ring,
   (ii) heterocyclic ring,
4) —O-(carbocyclic ring or heterocyclic ring),
5) —S-(carbocyclic ring or heterocyclic ring),
6) —$NR^{49}$-(carbocyclic ring or heterocyclic ring) (in which, $R^{49}$ is hydrogen or C1-4 alkyl which may be substituted with one phenyl),
7) —O—(C1-4 alkylene)-(carbocyclic ring or heterocyclic ring),
8) —S—(C1-4 alkylene)-(carbocyclic ring or heterocyclic ring),
9) —$NR^{50}$—(C1-4 alkylene)-(carbocyclic ring or heterocyclic ring) (in which, $R^{50}$ is hydrogen, C1-4 alkyl which may be substituted with one phenyl or C2-5 acyl which may be substituted with 1 to 3 of halogen) or
10) —CO-(carbocyclic ring or heterocyclic ring),
   or the said phenyl in L and carbocyclic ring and heterocyclic ring in M, which may be substituted with 1 to 3 substituent(s) selected from the group consisting of the following (i)-(xiv):
   (i) C1-4 alkyl,
   (ii) C2-4 alkenyl,
   (iii) hydroxy,
   (iv) C1-4 alkoxy,
   (v) —(C1-4 alkylene)-OH,
   (vi) —(C1-4 alkylene)-O—(C1-4 alkyl),
   (vii) halogen,
   (viii) $NR^{51}R^{52}$ (in which, $R^{51}$ and $R^{52}$ each, independently, is hydrogen, C1-4 alkyl or C1-4 alkoxycarbonyl, or $R^{51}$ and $R^{52}$ taken together with nitrogen atom to which is attached represents 5 to 7-membered saturated heterocyclic ring necessary containing one nitrogen atom and optionally further containing one nitrogen atom or one oxygen atom),
   (ix) $SR^{53}$ (in which, $R^{53}$ is hydrogen or C1-4 alkyl),
   (x) nitro,
   (xi) trifluoromethyl,
   (xii) C1-4 alkoxycarbonyl,
   (xiii) oxo,
   (xiv) C2-5 acyl),
   or a non-toxic salt thereof.

2. The compound according to claim 1 which is:
1) (2R)-N-(4-phenoxybenzyl)-3-cyclohexylmethylthio-2-((4R)-3-methoxymethylcarbonylthiazolidin-4-ylcarbonylamino)propanamide,
2) (2R)-N-(4-nitrobenzyl)-3-cyclohexylmethylthio-2-((4R)-3-(dimethylaminomethylcarbonyl)thiazolidin-4-ylcarbonylamino)propanamide,
3) (2R)-N-(4-methoxybenzyl)-3-cyclohexylmethylthio-2-((4R)-3-acetyloxymethylcarbonylthiazolidin-4-ylcarbonylamino)propanamide,
4) (2R)-N-(4-phenoxybenzyl)-3-cyclohexylmethylthio-2-((4R)-3-acetyloxymethylcarbonylthiazolidin-4-ylcarbonylamino)propanamide,
5) (2R)-N-(4-phenoxybenzyl)-3-cyclohexylmethylthio-2-((4R)-3-(2-methoxyethoxymethylcarbonyl)thiazolidin-4-ylcarbonylamino)propanamide,
6) (2R)-N-(4-phenoxybenzyl)-3-cyclohexylmethylthio-2-((4R)-3-(pyridin-3-ylcarbonyl)thiazolidin-4-ylcarbonylamino)propanamide,
7) (2R)-N-(4-methoxybenzyl)-3-cyclohexylmethylthio-2-((4R)-3-(2-methoxyacetyl)thiazolidin-4-ylcarbonylamino)propanamide,
8) (2R)-N-(4-phenoxybenzyl)-3-cyclohexylmethylthio-2-((4R)-3-allyloxycarbonylthiazolidin-4-ylcarbonylamino)propanamide,
9) (2R)-N-(4-methoxybenzyl)-3-cyclohexylmethylthio-2-((4R)-3-allyloxycarbonylthiazolidin-4-ylcarbonylamino)propanamide,
10) (2R)-N-(4-phenoxybenzyl)-3-cyclohexylmethylthio-2-((4R)-3-(3-hydroxy-3-methylbutyryl)thiazolidin-4-ylcarbonylamino)propanamide,
11) (2R)-N-(4-methoxybenzyl)-3-cyclohexylmethylthio-2-((4R)-3-(2-hydroxy-2-methylpropionyl)thiazolidin-4-ylcarbonylamino)propanamide,
12) (2R)-N-(4-phenoxybenzyl)-3-cyclohexylmethylthio-2-((4R)-3-(2-dimethylaminoacetyl)thiazolidin-4-ylcarbonylamino)propanamide,
13) (2R)-N-(4-phenoxybenzyl)-3-cyclohexylmethylthio-2-((4R)-3-(2-hydroxy-2-methylpropionyl)thiazolidin-4-ylcarbonylamino)propanamide,
14) (2R)-N-(4-phenoxybenzyl)-3-cyclohexylmethylthio-2-((4R)-3-(morpholin-4-ylmethylcarbonyl)thiazolidin-4-ylcarbonylamino)propanamide,
15) (2R)-N-(4-phenoxybenzyl)-3-cyclohexylmethylthio-2-((4R)-3-carboxymethylthiazolidin-4-ylcarbonylamino)propanamide,
16) (2R)-N-(4-nitrobenzyl)-3-cyclohexylmethylthio-2-((4R)-3-(3-methylbutyl)thiazolidin-4-ylcarbonylamino)propanamide,
17) (2R)-N-(4-methoxybenzyl)-3-cyclohexylmethylthio-2-((4R)-3-(2-hydroxyethyl)thiazolidin-4-ylcarbonylamino)propanamide,
18) (2R)-N-(4-methoxybenzyl)-3-cyclohexylmethylthio-2-((4R)-3-(3-hydroxy-3-methylbutyl)thiazolidin-4-ylcarbonylamino)propanamide,
19) (2R)-N-(4-phenoxybenzyl)-3-cyclohexylmethylthio-2-((4R)-3-(2-hydroxyethyl)thiazolidin-4-ylcarbonylamino)propanamide,
20) (2R)-N-(4-phenoxybenzyl)-3-cyclohexylmethylthio-2-((4R)-3-(2,3-dihydroxypropyl)thiazolidin-4-ylcarbonylamino)propanamide,
21) (2R)-N-(4-phenoxybenzyl)-3-cyclohexylmethylthio-2-((4R)-3-(2-methoxyethyl)thiazolidin-4-ylcarbonylamino)propanamide,
22) (2R)-N-(4-phenoxybenzyl)-3-cyclohexylmethylthio-2-((4R)-3-(2,3-dimethoxypropyl)thiazolidin-4-ylcarbonylamino)propanamide,
23) (2R)-N-(4-phenoxybenzyl)-3-cyclohexylmethylthio-2-((4R)-3-(3-hydroxy-3-methylbutyl)thiazolidin-4-ylcarbonylamino)propanamide,
24) (2R)-N-(4-phenoxybenzyl)-3-cyclohexylmethylthio-2-((4R)-3-(3-hydroxypropyl)thiazolidin-4-ylcarbonylamino)propanamide,
25) (2R)-N-((1R)-1-(4-nitrophenyl)ethyl)-3-cyclohexylmethylthio-2-((4R)-3-t-butylcarbamoylthiazolidin-4-ylcarbonylamino)propanamide,
26) (2R)-N-(4-methoxybenzyl)-3-cyclohexylmethylthio-2-((2RS)-3-t-butoxycarbonyl-1-oxothiazolidin-2-ylcarbonylamino)propanamide,
27) (2R)-N-(4-methoxybenzyl)-3-cyclohexylmethylthio-2-((2RS)-3-t-butoxycarbonyl-1,1-dioxothiazolidin-2-ylcarbonylamino)propanamide, 28) (2R)-N-(4-methoxybenzyl)-3-cyclohexylmethylthio-2-((4R)-3-t-butoxycarbonyl-1,1-dioxothiazolidin-4-ylcarbonylamino)propanamide,
29) (2R)-N-(4-methoxybenzyl)-3-cyclohexylmethylthio-2-((4R)-3-t-butoxycarbonyl-1-oxothiazolidin-4-ylcarbonylamino)propanamide,
30) (2R)-N-(4-methoxybenzyl)-3-cyclohexylmethylsulfinyl-2-((4R)-3-t-butoxycarbonyl-1-oxothiazolidin-4-ylcarbonylamino)propanamide,
31) (2R)-N-(4-methoxybenzyl)-3-cyclohexylmethylthio-2-((2RS,4R)-3-t-butoxycarbonyl-2-methoxymethylthiazolidin-4-ylcarbonylamino)propanamide,
32) (2R)-N-(4-methoxybenzyl)-3-cyclohexylmethylthio-2-((2RS,4R)-3-t-butoxycarbonyl-2-hydroxymethylthiazolidin-4-ylcarbonylamino)propanamide,
33) (2R)-N-(4-methoxybenzyl)-3-cyclohexylmethylthio-2-((2RS,4R)-3-t-butoxycarbonyl-2-(2-methylthioethyl)thiazolidin-4-ylcarbonylamino)propanamide,
34) (2R)-N-(4-methoxybenzyl)-3-cyclohexylmethylthio-2-((2RS,4R)-2-methoxymethylthiazolidin-4-ylcarbonylamino)propanamide,
35) (2R)-N-(4-methoxybenzyl)-3-cyclohexylmethylthio-2-((2RS,4R)-2-hydroxymethylthiazolidin-4-ylcarbonylamino)propanamide,
36) (2R)-N-(4-methoxybenzyl)-3-cyclohexylmethylthio-2-((2RS,4R)-2-(2-methylthioethyl)thiazolidin-4-ylcarbonylamino)propanamide,
37) (2R)-N-(4-phenoxybenzyl)-3-cyclohexylmethylthio-2-((4R)-3-hydroxymethylcarbonylthiazolidin-4-ylcarbonylamino)propanamide,
38) (2R)-N-(4-methoxybenzyl)-3-cyclohexylmethylthio-2-((4R)-3-hydroxymethylcarbonylthiazolidin-4-ylcarbonylamino)propanamide,
39) (2R)-N-(4-phenoxybenzyl)-3-cyclohexylmethylthio-2-((4R)-3-(morpholin-4-ylcarbonylmethyl)thiazolidin-4-ylcarbonylamino)propanamide,
40) (2R)-N-(4-phenoxybenzyl)-3-cyclohexylmethylthio-2-((4R)-3-(2-(tetrahydropyran-2-yloxy)ethyl)thiazolidin-4-ylcarbonylamino)propanamide,
41) (2R)-N-(4-phenoxybenzyl)-3-cyclohexylmethylthio-2-((4R)-3-(2-methoxyethyl)thiazolidin-4-ylcarbonylamino)propanamide,
42) (2R)-N-(4-nitrobenzyl)-3-cyclohexylmethylthio-2-((4R)-3-(3-methylbutyl)thiazolidin-4-ylcarbonylamino)propanamide, or
43) (2R)-N-(4-phenoxybenzyl)-3-cyclohexylmethylthio-2-((4R)-3-(morpholin-4-ylcarbonylmethyl)thiazolidin-4-ylcarbonylamino)propanamide, or
non-toxic salts thereof.

3. A pharmaceutical composition comprising a therapeutically effective amount of a compound of formula (I) depicted in claim 1, or a non-toxic salt thereof.

4. The pharmaceutical composition of claim 3 which is for treatment of cerebral infarct, transient ischemic attack, hypertension with stress, or epilepsy.

5. A pharmaceutical composition for treatment of pain comprising a therapeutically effective amount of a compound of formula (I) depicted in claim 1 or a non-toxic salt thereof.

6. The method for treating a disease selected from the group consisting of cerebral infarct, transient ischemic attack, hypertension with stress or epilepsy, comprising administering to a host in need of such treatment a therapeutically effective amount of a compound of formula (I) depicted in claim 1, or a non-toxic salt thereof.

7. The method for the treatment of pain induced by an excessive release of neurotransmitters from N-type calcium channels, comprising administering to a host in need of such treatment an effective amount of a compound of formula (I) depicted in claim 1, or a non-toxic salt thereof.

* * * * *